United States Patent
Mohan et al.

(10) Patent No.: US 11,603,375 B2
(45) Date of Patent: Mar. 14, 2023

(54) NLRP3 MODULATORS

(71) Applicant: Zomagen Biosciences Ltd, Encinitas, CA (US)

(72) Inventors: Raju Mohan, Encinitas, CA (US); John Nuss, Encinitas, CA (US); Jason Harris, Encinitas, CA (US); Shendong Yuan, Encinitas, CA (US)

(73) Assignee: ZOMAGEN BIOSCIENCES LTD, Encinitas, CA (US)

( * ) Notice: Subject to any disclaimer, the term of this patent is extended or adjusted under 35 U.S.C. 154(b) by 0 days.

(21) Appl. No.: 17/202,047

(22) Filed: Mar. 15, 2021

(65) Prior Publication Data

US 2021/0292336 A1 Sep. 23, 2021

Related U.S. Application Data

(60) Provisional application No. 62/990,363, filed on Mar. 16, 2020.

(51) Int. Cl.
| | |
|---|---|
| C07D 491/18 | (2006.01) |
| C07D 513/18 | (2006.01) |
| C07D 471/18 | (2006.01) |
| C07D 495/18 | (2006.01) |
| A61P 29/00 | (2006.01) |
| A61P 25/28 | (2006.01) |
| A61P 3/10 | (2006.01) |
| A61P 9/10 | (2006.01) |

(52) U.S. Cl.
CPC .............. *C07D 491/18* (2013.01); *A61P 3/10* (2018.01); *A61P 9/10* (2018.01); *A61P 25/28* (2018.01); *A61P 29/00* (2018.01); *C07D 471/18* (2013.01); *C07D 495/18* (2013.01); *C07D 513/18* (2013.01)

(58) Field of Classification Search
CPC .. C07D 471/18; C07D 491/18; C07D 495/18; C07D 513/18
See application file for complete search history.

(56) References Cited

U.S. PATENT DOCUMENTS

| | | | |
|---|---|---|---|
| 10,538,487 B2 | 1/2020 | O'Neill et al. | |
| 11,130,731 B2 | 9/2021 | O'Neill et al. | |

FOREIGN PATENT DOCUMENTS

| | | |
|---|---|---|
| WO | WO-2016131098 A1 | 8/2016 |
| WO | WO-2017140778 A1 | 8/2017 |
| WO | WO-2017184604 A1 | 10/2017 |
| WO | WO-2018136890 A1 | 7/2018 |
| WO | WO-2018215818 A1 | 11/2018 |
| WO | WO-2019008025 A1 | 1/2019 |
| WO | WO-2019034690 A1 | 2/2019 |
| WO | WO-2019034692 A1 | 2/2019 |
| WO | WO-2019079119 A1 | 4/2019 |
| WO | WO-2019121691 A1 | 6/2019 |
| WO | WO-2020018975 A1 | 1/2020 |
| WO | WO-2020086732 A1 | 4/2020 |
| WO | WO-2021009566 A1 | 1/2021 |
| WO | WO-2021009567 A1 | 1/2021 |
| WO | WO-2021188450 A1 | 9/2021 |

OTHER PUBLICATIONS

Berge et al. Pharmaceutical Salts. Journal of Pharmaceutical Sciences 66(1):1-19 (Jan. 1977).
PCT/IB2020/000634 International Search Report and Written Opinion dated Oct. 8, 2020.
PCT/IB2020/000668 International Search Report and Written Opinion dated Dec. 4, 2020.
PCT/US2021/022397 International Search Report and Written Opinion dated May 27, 2021.
Science IP Report 2019 (154 pgs).
Tran et al. Whole blood assay as a model for in vitro evaluation of inflammasome activation and subsequent caspase-mediated interleukin-1 beta release. PLoS ONE 14(4):e0214999 (2019).

*Primary Examiner* — Susanna Moore

(74) *Attorney, Agent, or Firm* — Wilson Sonsini Goodrich & Rosati

(57) ABSTRACT

Described herein are NLRP3 modulators and methods of utilizing NLRP3 modulators in the treatment of diseases, disorders or conditions. Also described herein are pharmaceutical compositions containing such compounds.

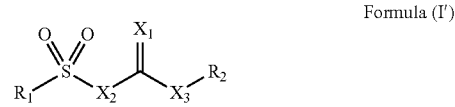

Formula (I')

20 Claims, No Drawings

NLRP3 MODULATORS

CROSS-REFERENCE

This application claims benefit of U.S. Provisional Application No. 62/990,363, filed on Mar. 16, 2020, which is herein incorporated by reference in its entirety.

BACKGROUND OF THE INVENTION

The NOD-like receptor (NLR) family, pyrin domain-containing protein 3 (NLRP3) inflammasome is a critical component of the innate immune response and inflammatory process, and its aberrant activity is pathogenic in inherited disorders such as cryopyrin-associated periodic syndromes (CAPS) and complex diseases such as multiple sclerosis, type 2 diabetes, Alzheimer's disease and atherosclerosis. Current treatments for NLRP3-related diseases include biologic agents that target IL-1. Small molecule inhibitors of NLRP3 provide an attractive alternative to these biologics, given their potential for improved safety and patient comfort and compliance.

SUMMARY OF THE INVENTION

In one aspect, provided herein are compounds of Formula (I'), or a pharmaceutically acceptable salt or solvate thereof:

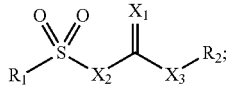

Formula (I')

wherein:
$X_1$ is O, S, or $N(R_3)$;
$X_2$ is $-N(R_4)-$ or $-C(R_4)_2-$;
$X_3$ is $-N(R_5)-$ or $-C(R_5)_2-$;
$Y_1$ is O, S, or $N(R_8)$;
$Y_2$ is N or $C(R_9)$;
$Z_1$ is O, S, $N(R_3)$, or $-C(R_{17})=C(R_{17})-$;
$Z_2$ is N or $C(R_{19})$;
$R_1$ is

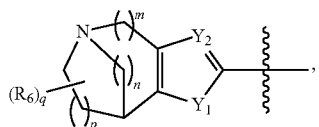

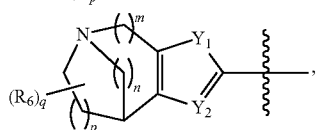

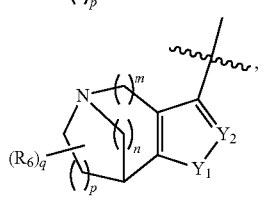

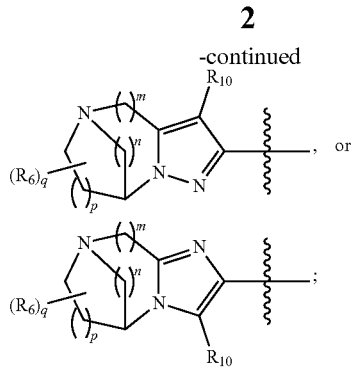

$R_2$ is

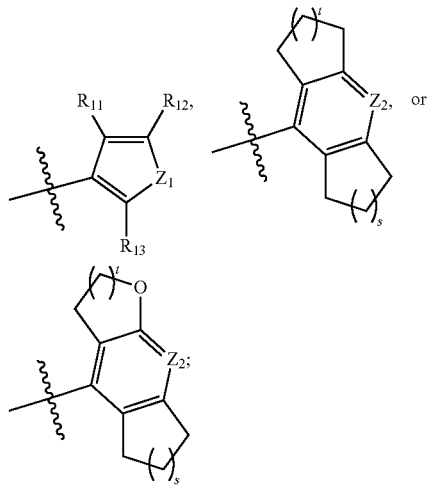

$R_3$ is hydrogen, $-OR_{14}$, $-CN$, $-NO_2$, or $-S(=O)_2 R_{15}$;
each $R_4$ is independently selected from hydrogen, $C_1-C_6$alkyl, $-C_1-C_6$alkyl-$OR_7$, and $-C_1-C_6$alkyl-$N(R_7)_2$;
each $R_5$ is independently selected from hydrogen, $C_1-C_6$alkyl, $-C_1-C_6$alkyl-$OR_7$, and $-C_1-C_6$alkyl-$N(R_7)_2$;
each $R_6$ is independently selected from $C_1-C_6$alkyl, $-C_1-C_6$alkyl-$CO_2R_{18}$, $C_1-C_6$haloalkyl, $-C_1-C_6$alkyl-$OR_7$, and $-C_1-C_6$alkyl-$N(R_7)_2$;
each $R_7$ is independently selected from hydrogen and $C_1-C_6$alkyl;
$R_8$ is hydrogen, $C_1-C_6$alkyl, $-C_1-C_6$alkyl-$OR_7$, $-C_1-C_6$alkyl-$N(R_7)_2$, or $C_3-C_6$cycloalkyl;
$R_9$ is hydrogen, halogen, $C_1-C_6$alkyl, $C_1-C_6$haloalkyl, or $C_3-C_6$cycloalkyl;
$R_{10}$ is hydrogen, halogen, $C_1-C_6$alkyl, $C_1-C_6$haloalkyl, $-C_1-C_6$alkyl-$OR_7$, or $-C_1-C_6$alkyl-$N(R_7)_2$;
$R_{11}$ and $R_{12}$ are independently selected from hydrogen, halogen, $C_1-C_6$alkyl, $C_1-C_6$haloalkyl, $-C_1-C_6$alkyl-$OR_7$, and $-C_1-C_6$alkyl-$N(R_7)_2$; or $R_{11}$ and $R_{12}$ are combined to form a 5- or 6-membered cycloalkyl ring;
$R_{13}$ is hydrogen, $C_1-C_6$alkyl, $C_1-C_6$haloalkyl, $C_2-C_6$alkenyl, $C_2-C_6$alkynyl, $C_3-C_5$cycloalkyl, $C_2-C_9$heterocycloalkyl, phenyl, or $C_2-C_9$heteroaryl, wherein $C_3-C_5$cycloalkyl, $C_2-C_9$heterocycloalkyl, phenyl, and $C_2-C_9$heteroaryl are optionally substituted by 1, 2, 3, or 4 $R_{16}$;
$R_{14}$ is hydrogen or $C_1-C_6$alkyl;

$R_{15}$ is $C_1$-$C_6$alkyl;

each $R_{16}$ is independently selected from halogen, $C_1$-$C_6$alkyl, $C_1$-$C_6$haloalkyl, $C_1$-$C_6$alkoxy, $C_1$-$C_6$haloalkoxy, $C_3$-$C_6$cycloalkyl, $C_2$-$C_9$heterocycloalkyl, $C_6$-$C_{10}$aryl, $C_2$-$C_9$heteroaryl, wherein $C_3$-$C_6$ cycloalkyl, $C_2$-$C_9$heterocycloalkyl, $C_6$-$C_{10}$aryl, $C_2$-$C_9$ heteroaryl are optionally substituted with 1, 2, or 3 groups selected from halogen, $C_1$-$C_6$alkyl, $C_1$-$C_6$haloalkyl, $C_1$-$C_6$alkoxy, and $C_1$-$C_6$haloalkoxy;

each $R_{17}$ is independently selected from hydrogen, halogen, $C_1$-$C_6$alkyl, $C_1$-$C_6$haloalkyl, —$C_1$-$C_6$alkyl-$OR_7$, and —$C_1$-$C_6$alkyl-$N(R_7)_2$;

$R_{18}$ is hydrogen or $C_1$-$C_6$alkyl;

$R_{19}$ is hydrogen, halogen, —CN, $C_1$-$C_6$alkyl, $C_1$-$C_6$haloalkyl, —$C_1$-$C_6$alkyl-$OR_7$, or —$C_1$-$C_6$alkyl-$N(R_7)_2$;

m is 0, 1, or 2;
n is 1, 2, or 3;
p is 0, 1, or 2;
q is 0, 1, 2, 3, or 4;
s is 1, 2, or 3; and
t is 1, 2, or 3.

In another aspect, provided herein are compounds of Formula (I), or a pharmaceutically acceptable salt or solvate thereof:

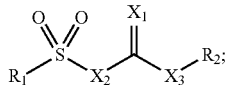

Formula (I)

wherein:
$X_1$ is O, S, or $N(R_3)$;
$X_2$ is —$N(R_4)$— or —$C(R_4)_2$—;
$X_3$ is —$N(R_5)$— or —$C(R_5)_2$—;
$Y_1$ is O, S, or $N(R_8)$;
$Y_2$ is N or $C(R_9)$;
$Z_1$ is O, S, $N(R_3)$, or —$C(R_{17})$=$C(R_{17})$—;
$Z_2$ is N or $C(R_{19})$;
$R_1$ is

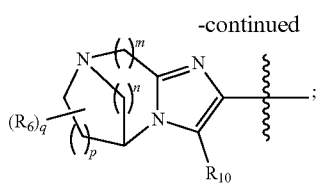

$R_2$ is

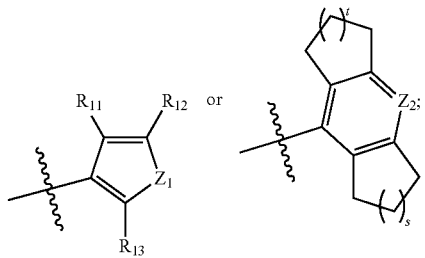

$R_3$ is hydrogen, —$OR_{14}$, —CN, —$NO_2$, or —$S(=O)_2R_{15}$;

each $R_4$ is independently selected from hydrogen, $C_1$-$C_6$alkyl, —$C_1$-$C_6$alkyl-$OR_7$, and —$C_1$-$C_6$alkyl-$N(R_7)_2$;

each $R_5$ is independently selected from hydrogen, $C_1$-$C_6$alkyl, —$C_1$-$C_6$alkyl-$OR_7$, and —$C_1$-$C_6$alkyl-$N(R_7)_2$;

each $R_6$ is independently selected from $C_1$-$C_6$alkyl, —$C_1$-$C_6$alkyl-$CO_2R_{18}$, $C_1$-$C_6$haloalkyl, —$C_1$-$C_6$alkyl-$OR_7$, and —$C_1$-$C_6$alkyl-$N(R_7)_2$;

each $R_7$ is independently selected from hydrogen and $C_1$-$C_6$alkyl;

$R_8$ is hydrogen, $C_1$-$C_6$alkyl, —$C_1$-$C_6$alkyl-$OR_7$, —$C_1$-$C_6$alkyl-$N(R_7)_2$, or $C_3$-$C_6$cycloalkyl;

$R_9$ is hydrogen, halogen, $C_1$-$C_6$alkyl, $C_1$-$C_6$haloalkyl, or $C_3$-$C_6$cycloalkyl;

$R_{10}$ is hydrogen, halogen, $C_1$-$C_6$alkyl, $C_1$-$C_6$haloalkyl, —$C_1$-$C_6$alkyl-$OR_7$, or —$C_1$-$C_6$alkyl-$N(R_7)_2$;

$R_{11}$ and $R_{12}$ are independently selected from halogen, $C_1$-$C_6$alkyl, $C_1$-$C_6$haloalkyl, —$C_1$-$C_6$alkyl-$OR_7$, and —$C_1$-$C_6$alkyl-$N(R_7)_2$; or $R_{11}$ and $R_{12}$ are combined to form a 5- or 6-membered cycloalkyl ring;

$R_{13}$ is phenyl or $C_2$-$C_9$heteroaryl, wherein phenyl and $C_2$-$C_9$heteroaryl are optionally substituted by 1, 2, 3, or 4 $R_{16}$;

$R_{14}$ is hydrogen or $C_1$-$C_6$alkyl;

$R_{15}$ is $C_1$-$C_6$alkyl;

each $R_{16}$ is independently selected from halogen, $C_1$-$C_6$alkyl, $C_1$-$C_6$haloalkyl, $C_1$-$C_6$alkoxy, $C_1$-$C_6$haloalkoxy, $C_3$-$C_6$cycloalkyl, $C_2$-$C_9$heterocycloalkyl, $C_6$-$C_{10}$aryl, $C_2$-$C_9$heteroaryl, wherein $C_3$-$C_6$cycloalkyl, $C_2$-$C_9$heterocycloalkyl, $C_6$-$C_{10}$aryl, $C_2$-$C_9$heteroaryl are optionally substituted with 1, 2, or 3 groups selected from halogen, $C_1$-$C_6$alkyl, $C_1$-$C_6$haloalkyl, $C_1$-$C_6$alkoxy, and $C_1$-$C_6$haloalkoxy;

each $R_{17}$ is independently selected from hydrogen, halogen, $C_1$-$C_6$alkyl, $C_1$-$C_6$haloalkyl, —$C_1$-$C_6$alkyl-$OR_7$, and —$C_1$-$C_6$alkyl-$N(R_7)_2$;

$R_{18}$ is hydrogen or $C_1$-$C_6$alkyl;

$R_{19}$ is hydrogen, halogen, —CN, $C_1$-$C_6$alkyl, $C_1$-$C_6$haloalkyl, —$C_1$-$C_6$alkyl-$OR_7$, or —$C_1$-$C_6$alkyl-$N(R_7)_2$;

m is 0, 1, or 2;

n is 1, 2, or 3;

p is 0, 1, or 2;

q is 0, 1, 2, 3, or 4;

s is 1, 2, or 3; and t is 1, 2, or 3.

In some embodiments is a compound of Formula (I') or (I), or a pharmaceutically acceptable salt or solvate thereof, wherein $R_1$ is

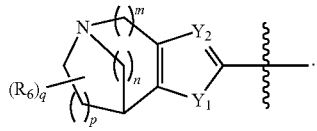

In some embodiments is a compound of Formula (I') or (I), or a pharmaceutically acceptable salt or solvate thereof, wherein $R_1$ is

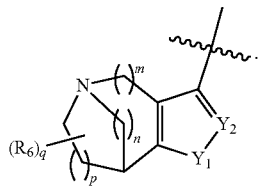

In some embodiments is a compound of Formula (I') or (I), or a pharmaceutically acceptable salt or solvate thereof, wherein $Y_2$ is $C(R_9)$. In some embodiments is a compound of Formula (I') or (I), or a pharmaceutically acceptable salt or solvate thereof, wherein $R_9$ is hydrogen or $C_1$-$C_6$alkyl. In some embodiments is a compound of Formula (I') or (I), or a pharmaceutically acceptable salt or solvate thereof, wherein $R_9$ is hydrogen. In some embodiments is a compound of Formula (I') or (I), or a pharmaceutically acceptable salt or solvate thereof, wherein $Y_2$ is N. In some embodiments is a compound of Formula (I') or (I), or a pharmaceutically acceptable salt or solvate thereof, wherein $Y_1$ is O. In some embodiments is a compound of Formula (I') or (I), or a pharmaceutically acceptable salt or solvate thereof, wherein $Y_1$ is S. In some embodiments is a compound of Formula (I') or (I), or a pharmaceutically acceptable salt or solvate thereof, wherein $Y_1$ is $N(R_8)$. In some embodiments is a compound of Formula (I') or (I), or a pharmaceutically acceptable salt or solvate thereof, wherein $R_8$ is hydrogen, $C_1$-$C_6$alkyl, or $C_3$-$C_6$cycloalkyl. In some embodiments is a compound of Formula (I') or (I), or a pharmaceutically acceptable salt or solvate thereof, wherein $R_8$ is hydrogen. In some embodiments is a compound of Formula (I') or (I), or a pharmaceutically acceptable salt or solvate thereof, wherein $R_8$ is $C_1$-$C_6$alkyl. In some embodiments is a compound of Formula (I') or (I), or a pharmaceutically acceptable salt or solvate thereof, wherein $R_8$ is $C_3$-$C_6$cycloalkyl. In some embodiments is a compound of Formula (I') or (I), or a pharmaceutically acceptable salt or solvate thereof, wherein $R_1$ is

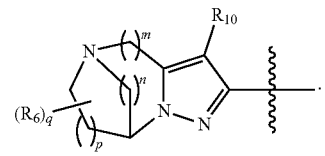

In some embodiments is a compound of Formula (I') or (I), or a pharmaceutically acceptable salt or solvate thereof, wherein $R_1$ is

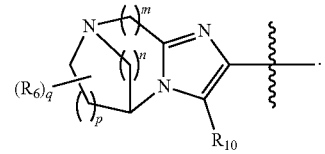

In some embodiments is a compound of Formula (I') or (I), or a pharmaceutically acceptable salt or solvate thereof, wherein $R_{10}$ is hydrogen. In some embodiments is a compound of Formula (I') or (I), or a pharmaceutically acceptable salt or solvate thereof, wherein each $R_6$ is independently selected from $C_1$-$C_6$alkyl. In some embodiments is a compound of Formula (I') or (I), or a pharmaceutically acceptable salt or solvate thereof, wherein each $R_6$ is —$CH_3$. In some embodiments is a compound of Formula (I') or (I), or a pharmaceutically acceptable salt or solvate thereof, wherein q is 1. In some embodiments is a compound of Formula (I') or (I), or a pharmaceutically acceptable salt or solvate thereof, wherein q is 2. In some embodiments is a compound of Formula (I') or (I), or a pharmaceutically acceptable salt or solvate thereof, wherein q is 3. In some embodiments is a compound of Formula (I') or (I), or a pharmaceutically acceptable salt or solvate thereof, wherein q is 0. In some embodiments is a compound of Formula (I') or (I), or a pharmaceutically acceptable salt or solvate thereof, wherein n is 2. In some embodiments is a compound of Formula (I') or (I), or a pharmaceutically acceptable salt or solvate thereof, wherein n is 1. In some embodiments is a compound of Formula (I') or (I), or a pharmaceutically acceptable salt or solvate thereof, wherein m is 1. In some embodiments is a compound of Formula (I') or (I), or a pharmaceutically acceptable salt or solvate thereof, wherein p is 1. In some embodiments is a compound of Formula (I') or (I), or a pharmaceutically acceptable salt or solvate thereof, wherein $R_1$ is

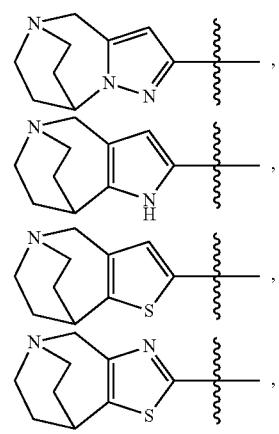

-continued

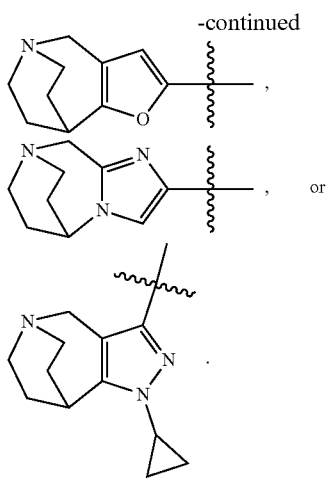

In some embodiments is a compound of Formula (I') or (I), or a pharmaceutically acceptable salt or solvate thereof, wherein $R_2$ is

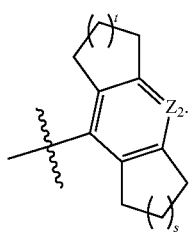

In some embodiments is a compound of Formula (I') or (I), or a pharmaceutically acceptable salt or solvate thereof, wherein s is 1. In some embodiments is a compound of Formula (I') or (I), or a pharmaceutically acceptable salt or solvate thereof, wherein t is 1. In some embodiments is a compound of Formula (I') or (I), or a pharmaceutically acceptable salt or solvate thereof, wherein $Z_2$ is $C(R_{19})$. In some embodiments is a compound of Formula (I') or (I), or a pharmaceutically acceptable salt or solvate thereof, wherein $R_{19}$ is hydrogen. In some embodiments is a compound of Formula (I') or (I), or a pharmaceutically acceptable salt or solvate thereof, wherein $Z_2$ is N. In some embodiments is a compound of Formula (I') or (I), or a pharmaceutically acceptable salt or solvate thereof, wherein $R_2$ is

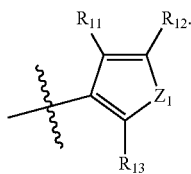

In some embodiments is a compound of Formula (I') or (I), or a pharmaceutically acceptable salt or solvate thereof, wherein $Z_1$ is S. In some embodiments is a compound of Formula (I') or (I), or a pharmaceutically acceptable salt or solvate thereof, wherein $Z_1$ is O. In some embodiments is a compound of Formula (I') or (I), or a pharmaceutically acceptable salt or solvate thereof, wherein $Z_1$ is —$C(R_{17})$=$C(R_{17})$—. In some embodiments is a compound of Formula (I') or (I), or a pharmaceutically acceptable salt or solvate thereof, wherein each $R_{17}$ is hydrogen. In some embodiments is a compound of Formula (I') or (I), or a pharmaceutically acceptable salt or solvate thereof, wherein $R_{11}$ and $R_{12}$ are combined to form a 5- or 6-membered cycloalkyl ring. In some embodiments is a compound of Formula (I') or (I), or a pharmaceutically acceptable salt or solvate thereof, wherein $R_{13}$ is phenyl optionally substituted by 1, 2, 3, or 4 $R_{16}$. In some embodiments is a compound of Formula (I') or (I), or a pharmaceutically acceptable salt or solvate thereof, wherein $R_{13}$ is $C_2$-$C_9$heteroaryl optionally substituted by 1, 2, 3, or 4 $R_{16}$. In some embodiments is a compound of Formula (I') or (I), or a pharmaceutically acceptable salt or solvate thereof, wherein $R_{13}$ is pyridyl optionally substituted by 1, 2, 3, or 4 $R_{16}$. In some embodiments is a compound of Formula (I') or (I), or a pharmaceutically acceptable salt or solvate thereof, wherein each $R_{16}$ is independently selected from halogen, $C_1$-$C_6$alkyl, $C_1$-$C_6$haloalkyl, and $C_1$-$C_6$alkoxy. In some embodiments is a compound of Formula (I') or (I), or a pharmaceutically acceptable salt or solvate thereof, wherein each $R_{16}$ is $C_1$-$C_6$alkoxy. In some embodiments is a compound of Formula (I') or (I), or a pharmaceutically acceptable salt or solvate thereof, wherein $R_2$ is

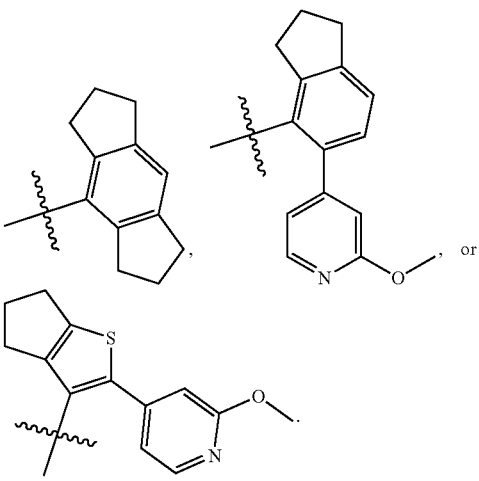

In some embodiments is a compound of Formula (I') or (I), or a pharmaceutically acceptable salt or solvate thereof, wherein $X_2$ is —$N(R_4)$—. In some embodiments is a compound of Formula (I') or (I), or a pharmaceutically acceptable salt or solvate thereof, wherein each $R_4$ is hydrogen. In some embodiments is a compound of Formula (I') or (I), or a pharmaceutically acceptable salt or solvate thereof, wherein $X_3$ is —$N(R_5)$—. In some embodiments is a compound of Formula (I') or (I), or a pharmaceutically acceptable salt or solvate thereof, wherein $X_3$ is —$C(R_5)_2$—. In some embodiments is a compound of Formula (I') or (I), or a pharmaceutically acceptable salt or solvate thereof, wherein each $R_5$ is hydrogen. In some embodiments is a compound of Formula (I') or (I), or a pharmaceutically acceptable salt or solvate thereof, wherein $X_1$ is O.

In another aspect described herein is a pharmaceutical composition comprising a compound of Formula (I') or (I), or a pharmaceutically acceptable salt or solvate thereof, and a pharmaceutically acceptable excipient.

In some embodiments described herein is a method of treating a metabolic disease in a patient in need thereof, comprising administering to the patient a therapeutically effective amount of a compound of Formula (I') or (I), or a pharmaceutically acceptable salt or solvate thereof. In some embodiments described herein is a method of treating a metabolic disease in a patient in need thereof, comprising administering to the patient a therapeutically effective amount of a compound of Formula (I') or (I), or a pharmaceutically acceptable salt or solvate thereof, wherein the metabolic disease is selected from type 2 diabetes, atherosclerosis, obesity, and gout.

In some embodiments described herein is a method of treating a liver disease in a patient in need thereof, comprising administering to the patient a therapeutically effective amount of a compound of Formula (I') or (I), or a pharmaceutically acceptable salt or solvate thereof. In some embodiments described herein is a method of treating a liver disease in a patient in need thereof, comprising administering to the patient a therapeutically effective amount of a compound of Formula (I') or (I), or a pharmaceutically acceptable salt or solvate thereof, wherein the liver disease is selected from non-alcoholic fatty liver disease (NAFLD), non-alcoholic steatohepatitis (NASH), alcoholic steatohepatitis (ASH), viral hepatitis, and cirrhosis.

In some embodiments described herein is a method of treating a lung disease in a patient in need thereof, comprising administering to the patient a therapeutically effective amount of a compound of Formula (I') or (I), or a pharmaceutically acceptable salt or solvate thereof. In some embodiments described herein is a method of treating a lung disease in a patient in need thereof, comprising administering to the patient a therapeutically effective amount of a compound of Formula (I') or (I), or a pharmaceutically acceptable salt or solvate thereof, wherein the lung disease is selected from asthma, chronic obstructive pulmonary disease (COPD), and pulmonary idiopathic fibrosis.

In some embodiments described herein is a method of treating a central nervous system disease in a patient in need thereof, comprising administering to the patient a therapeutically effective amount of a compound of Formula (I') or (I), or a pharmaceutically acceptable salt or solvate thereof. In some embodiments described herein is a method of treating a central nervous system disease in a patient in need thereof, comprising administering to the patient a therapeutically effective amount of a compound of Formula (I') or (I), or a pharmaceutically acceptable salt or solvate thereof, wherein the central nervous system disease is selected from Alzheimer's disease, multiple sclerosis, Amyotrophic Lateral Sclerosis, and Parkinson's disease.

In some embodiments described herein is a method of treating an inflammatory or autoimmune disease in a patient in need thereof, comprising administering to the patient a therapeutically effective amount of a compound of Formula (I') or (I), or a pharmaceutically acceptable salt or solvate thereof. In some embodiments described herein is a method of treating an inflammatory or autoimmune disease in a patient in need thereof, comprising administering to the patient a therapeutically effective amount of a compound of Formula (I') or (I), or a pharmaceutically acceptable salt or solvate thereof, wherein the inflammatory or autoimmune disease is selected from rheumatoid arthritis, multiple sclerosis, psoriasis, lupus, inflammatory bowel disease, Crohn's disease, and ulcerative colitis.

In some embodiments described herein is a method of treating a cardiovascular disease in a patient in need thereof, comprising administering to the patient a therapeutically effective amount of a compound of Formula (I') or (I), or a pharmaceutically acceptable salt or solvate thereof. In some embodiments described herein is a method of treating a cardiovascular disease in a patient in need thereof, comprising administering to the patient a therapeutically effective amount of a compound of Formula (I') or (I), or a pharmaceutically acceptable salt or solvate thereof, wherein the cardiovascular disease is atherosclerosis or stroke.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Definitions

In the context of this disclosure, a number of terms shall be utilized.

Unless defined otherwise, all technical and scientific terms used herein have the same meaning as is commonly understood to which the claimed subject matter belongs. In the event that there are a plurality of definitions for terms herein, those in this section prevail. All patents, patent applications, publications and published nucleotide and amino acid sequences (e.g., sequences available in GenBank or other databases) referred to herein are incorporated by reference. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The section headings used herein are for organizational purposes only and are not to be construed as limiting the subject matter described.

Definition of standard chemistry terms may be found in reference works, including but not limited to, Carey and Sundberg "Advanced Organic Chemistry $4^{th}$ Ed." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology were used.

Unless specific definitions are provided, the nomenclature employed in connection with, and the laboratory procedures and techniques of, analytical chemistry, synthetic organic chemistry, and medicinal and pharmaceutical chemistry described herein are those recognized in the field. Standard techniques can be used for chemical syntheses, chemical analyses, pharmaceutical preparation, formulation, and delivery, and treatment of patients. Standard techniques can be used for recombinant DNA, oligonucleotide synthesis, and tissue culture and transformation (e.g., electroporation, lipofection). Reactions and purification techniques can be performed e.g., using kits of manufacturer's specifications or as commonly accomplished in the art or as described herein. The foregoing techniques and procedures can be generally performed of conventional methods and as described in various general and more specific references that are cited and discussed throughout the present specification.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods, compounds, compositions described herein.

As used herein, $C_1$-$C_x$ includes $C_1$-$C_2$, $C_1$-$C_3$ ... $C_1$-$C_x$. $C_1$-$C_x$ refers to the number of carbon atoms that make up the moiety to which it designates (excluding optional substituents).

An "alkyl" group refers to a straight or branched hydrocarbon chain radical consisting solely of carbon and hydrogen atoms, containing no unsaturation. In some embodiments, the "alkyl" group may have 1 to 6 carbon atoms (whenever it appears herein, a numerical range such as "1 to 6" refers to each integer in the given range; e.g., "1 to 6 carbon atoms" means that the alkyl group may consist of 1 carbon atom, 2 carbon atoms, 3 carbon atoms, etc., up to and including 6 carbon atoms, although the present definition also covers the occurrence of the term "alkyl" where no numerical range is designated). The alkyl group of the compounds described herein may be designated as "$C_1$-$C_6$alkyl" or similar designations. By way of example only, "$C_1$-$C_6$alkyl" indicates that there are one to six carbon atoms in the alkyl chain, i.e., the alkyl chain is selected from the group consisting of methyl, ethyl, n-propyl, iso-propyl, n-butyl, iso-butyl, sec-butyl, t-butyl, n-pentyl, iso-pentyl, neo-pentyl, and hexyl. Alkyl groups can be substituted or unsubstituted. Depending on the structure, an alkyl group can be a monoradical or a diradical (i.e., an alkylene group).

An "alkoxy" refers to a "—O-alkyl" group, where alkyl is as defined herein.

The term "alkenyl" refers to a straight or branched hydrocarbon chain radical group consisting solely of carbon and hydrogen atoms, containing at least one carbon-carbon double bond. Non-limiting examples of an alkenyl group include —CH=CH$_2$, —C(CH$_3$)=CH$_2$, —CH=CHCH$_3$, —CH=C(CH$_3$)$_2$ and —C(CH$_3$)=CHCH$_3$. In some embodiments, an alkenyl groups may have 2 to 6 carbons. Alkenyl groups can be substituted or unsubstituted. Depending on the structure, an alkenyl group can be a monoradical or a diradical (i.e., an alkenylene group).

The term "alkynyl" refers to a straight or branched hydrocarbon chain radical group consisting solely of carbon and hydrogen atoms, containing at least one carbon-carbon triple bond. Non-limiting examples of an alkynyl group include —C≡CH, —C≡CCH$_3$, —C≡CCH$_2$CH$_3$ and —C≡CCH$_2$CH$_2$CH$_3$. In some embodiments, an alkynyl group can have 2 to 6 carbons. Alkynyl groups can be substituted or unsubstituted. Depending on the structure, an alkynyl group can be a monoradical or a diradical (i.e., an alkynylene group).

"Amino" refers to a —NH$_2$ group.

The term "alkylamine" or "alkylamino" refers to the —N(alkyl)$_x$H$_y$ group, where alkyl is as defined herein and x and y are selected from the group x=1, y=1 and x=2, y=0. When x=2, the alkyl groups, taken together with the nitrogen to which they are attached, can optionally form a cyclic ring system. "Dialkylamino" refers to a —N(alkyl)$_2$ group, where alkyl is as defined herein.

The term "aromatic" refers to a planar ring having a delocalized π-electron system containing 4n+2 π electrons, where n is an integer. Aromatic rings can be formed from five, six, seven, eight, nine, or more than nine atoms. Aromatics can be optionally substituted. The term "aromatic" includes both aryl groups (e.g., phenyl, naphthalenyl) and heteroaryl groups (e.g., pyridinyl, quinolinyl).

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, and naphthalenyl. Depending on the structure, an aryl group can be a monoradical or a diradical (i.e., an arylene group).

"Carboxy" refers to —CO$_2$H. In some embodiments, carboxy moieties may be replaced with a "carboxylic acid bioisostere", which refers to a functional group or moiety that exhibits similar physical and/or chemical properties as a carboxylic acid moiety. A carboxylic acid bioisostere has similar biological properties to that of a carboxylic acid group. A compound with a carboxylic acid moiety can have the carboxylic acid moiety exchanged with a carboxylic acid bioisostere and have similar physical and/or biological properties when compared to the carboxylic acid-containing compound. For example, in one embodiment, a carboxylic acid bioisostere would ionize at physiological pH to roughly the same extent as a carboxylic acid group. Examples of bioisosteres of a carboxylic acid include, but are not limited to,

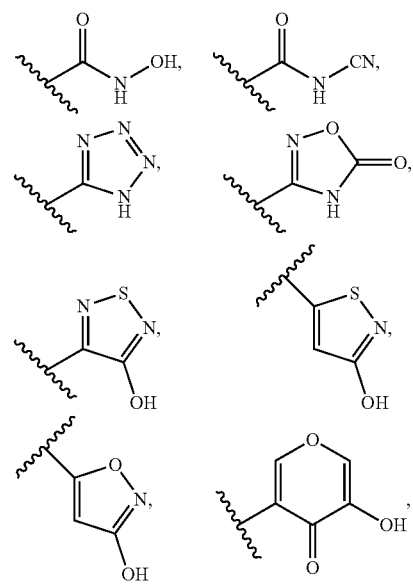

and the like.

The term "cycloalkyl" refers to a monocyclic or polycyclic non-aromatic radical, wherein each of the atoms forming the ring (i.e. skeletal atoms) is a carbon atom. Cycloalkyls may be saturated, or partially unsaturated. Cycloalkyls may be fused with an aromatic ring (in which case the cycloalkyl is bonded through a non-aromatic ring carbon atom). In some embodiments, cycloalkyl groups include groups having from 3 to 10 ring atoms.

The terms "heteroaryl" or, alternatively, "heteroaromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom.

A "heterocycloalkyl" group or "heteroalicyclic" group refers to a cycloalkyl group, wherein at least one skeletal ring atom is a heteroatom selected from nitrogen, oxygen and sulfur. The radicals may be fused with an aryl or heteroaryl. The term heteroalicyclic also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring).

The term "halo" or, alternatively, "halogen" means fluoro, chloro, bromo and iodo.

The term "haloalkyl" refers to an alkyl group that is substituted with one or more halogens. The halogens may the same or they may be different. Non-limiting examples of haloalkyls include —$CH_2Cl$, —$CF_3$, —$CHF_2$, —$CH_2CF_3$, —$CF_2CF_3$, and the like.

The terms "fluoroalkyl" and "fluoroalkoxy" include alkyl and alkoxy groups, respectively, that are substituted with one or more fluorine atoms. Non-limiting examples of fluoroalkyls include —$CF_3$, —$CHF_2$, —$CH_2F$, —$CH_2CF_3$, —$CF_2CF_3$, —$CF_2CF_2CF_3$, —$CF(CH_3)_3$, and the like. Non-limiting examples of fluoroalkoxy groups, include —$OCF_3$, —$OCHF_2$, —$OCH_2F$, —$OCH_2CF_3$, —$OCF_2CF_3$, —$OCF_2CF_2CF_3$, —$OCF(CH_3)_2$, and the like.

The term "heteroalkyl" refers to an alkyl radical where one or more skeletal chain atoms is selected from an atom other than carbon, e.g., oxygen, nitrogen, sulfur, phosphorus, silicon, or combinations thereof. The heteroatom(s) may be placed at any interior position of the heteroalkyl group. Examples include, but are not limited to, —$CH_2$—O—$CH_3$, —$CH_2$—$CH_2$—O—$CH_3$, —$CH_2$—NH—$CH_3$, —$CH_2$—$CH_2$—NH—$CH_3$, —$CH_2$—N($CH_3$)—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —$CH_2$—NH—$OCH_3$, —$CH_2$—O—Si($CH_3$)$_3$, —$CH_2$—CH=N—$OCH_3$, and —CH=CH—N($CH_3$)—$CH_3$. In addition, up to two heteroatoms may be consecutive, such as, by way of example, —$CH_2$—NH—$OCH_3$ and —$CH_2$—O—Si($CH_3$)$_3$. Excluding the number of heteroatoms, a "heteroalkyl" may have from 1 to 6 carbon atoms.

The term "bond" or "single bond" refers to a chemical bond between two atoms, or two moieties when the atoms joined by the bond are considered to be part of larger substructure.

The term "moiety" refers to a specific segment or functional group of a molecule. Chemical moieties are often recognized chemical entities embedded in or appended to a molecule.

As used herein, the substituent "R" appearing by itself and without a number designation refers to a substituent selected from among from alkyl, haloalkyl, heteroalkyl, alkenyl, cycloalkyl, aryl, heteroaryl (bonded through a ring carbon), and heterocycloalkyl.

"Optional" or "optionally" means that a subsequently described event or circumstance may or may not occur and that the description includes instances when the event or circumstance occurs and instances in which it does not.

The term "optionally substituted" or "substituted" means that the referenced group may be substituted with one or more additional group(s) individually and independently selected from alkyl, cycloalkyl, aryl, heteroaryl, heterocycloalkyl, —OH, alkoxy, aryloxy, alkylthio, arylthio, alkylsulfoxide, arylsulfoxide, alkylsulfone, arylsulfone, —CN, alkyne, $C_1$-$C_6$alkylalkyne, halo, acyl, acyloxy, —$CO_2H$, —$CO_2$-alkyl, nitro, haloalkyl, fluoroalkyl, and amino, including mono- and di-substituted amino groups (e.g. —$NH_2$, —NHR, —N(R)$_2$), and the protected derivatives thereof. By way of example, an optional substituents may be $L^sR^s$, wherein each $L^s$ is independently selected from a bond, —O—, —C(=O)—, —S—, —S(=O)—, —S(=O)$_2$—, —NH—, —NHC(O)—, —C(O)NH—, S(=O)$_2$NH—, —NHS(=O)$_2$, —OC(O)NH—, —NHC(O)O—, —($C_1$-$C_6$alkyl)-, or —($C_2$-$C_6$alkenyl)-; and each $R^s$ is independently selected from among H, ($C_1$-$C_6$alkyl), ($C_3$-$C_8$cycloalkyl), aryl, heteroaryl, heterocycloalkyl, and $C_1$-$C_6$heteroalkyl. The protecting groups that may form the protective derivatives of the above substituents are found in sources such as Greene and Wuts, above.

As used herein, the term "about" or "approximately" means within 20%, preferably within 10%, and more preferably within 5% of a given value or range.

The term a "therapeutically effective amount" as used herein refers to the amount of a NLRP3 inhibitor that, when administered to a mammal in need, is effective to at least partially ameliorate or to at least partially prevent conditions related to skin aging.

As used herein, the term "expression" includes the process by which polynucleotides are transcribed into mRNA and translated into peptides, polypeptides, or proteins.

The term "modulate" encompasses either a decrease or an increase in activity or expression depending on the target molecule.

The term "activator" is used in this specification to denote any molecular species that results in activation of the indicated receptor, regardless of whether the species itself binds to the receptor or a metabolite of the species binds to the receptor when the species is administered topically. Thus, the activator can be a ligand of the receptor or it can be an activator that is metabolized to the ligand of the receptor, i.e., a metabolite that is formed in tissue and is the actual ligand.

The term "patient" or "mammal" refers to a human, a non-human primate, canine, feline, bovine, ovine, porcine, murine, or other veterinary or laboratory mammal. Those skilled in the art recognize that a therapy which reduces the severity of a pathology in one species of mammal is predictive of the effect of the therapy on another species of mammal.

"Pharmaceutically acceptable salt" includes both acid and base addition salts. A pharmaceutically acceptable salt of any one of the compounds described herein is intended to encompass any and all pharmaceutically suitable salt forms. Preferred pharmaceutically acceptable salts of the compounds described herein are pharmaceutically acceptable acid addition salts, and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997)). Acid addition salts of basic compounds are prepared by contacting the free base forms with a sufficient amount of the desired acid to produce the salt.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts, and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins, and the like. See Berge et al., supra.

As used herein, "treatment" or "treating" or "palliating" or "ameliorating" are used interchangeably herein. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are administered to a patient at risk of developing a particular disease, or to a patient reporting one or more of the physiological symptoms of a disease, even though a diagnosis of this disease has not been made.

NLRP3 Modulators

NLRP3 is an intracellular signaling molecule that senses many pathogen-derived, environmental and host-derived factors. Upon activation, NLRP3 binds to apoptosis-associated speck-like protein containing a caspase activation and recruitment domain (ASC). ASC then polymerizes to form a large aggregate known as an ASC speck.

Polymerized ASC associates with the cysteine protease caspase-1 to form a complex termed the inflammasome. This results in the activation of active caspase-1, which cleaves the precursor forms of the proinflammatory cytokines IL-1β and IL-18 (termed pro-IL-ιβ and pro-IL-18 respectively) to thereby activate these cytokines. Caspase-1 also mediates a type of inflammatory cell death known as pyroptosis. The ASC speck aggregate can also recruit and activate caspase-8, which is able to process pro-IL-ιβ and pro-IL-18 and trigger apoptotic cell death.

Caspase-1 cleaves pro-IL-ιβ and pro-IL-18 to their active forms, which are secreted from the cell. Active caspase-1 also cleaves gasdermin-D to trigger pyroptosis. Through its control of the pyroptotic cell death pathway, caspase-1 also mediates the release of alarmin molecules such as IL-33 and high mobility group box 1 protein (HMGB1). Caspase-1 also cleaves intracellular IL-1R2 resulting in its degradation and allowing the release of IL-1α. In human cells caspase-1 may also control the processing and secretion of IL-37. A number of other caspase-i substrates such as components of the cytoskeleton and glycolysis pathway may contribute to caspase-I dependent inflammation.

NLRP3-dependent ASC specks are released into the extracellular environment where they can activate caspase-1, induce processing of caspase-1 substrates and propagate inflammation. Active cytokines derived from NLRP3 inflammasome activation are important drivers of inflammation and interact with other cytokine pathways to shape the immune response to infection and injury. For example, IL-ιβ signaling induces the secretion of the pro-inflammatory cytokines IL-6 and TNF. IL-1β and IL-18 synergize with IL-23 to induce IL-17 production by memory CD4 Th17 cells and by γδ T cells in the absence of T cell receptor engagement. IL-18 and IL-12 also synergize to induce IFN-γ production from memory T cells and NK cells driving a Th1 response.

The inherited CAPS diseases Muckle-Wells syndrome (MWS), familial cold autoinflammatory syndrome (FCAS) and neonatal-onset multisystem inflammatory disease (NOMID) are caused by gain-of-function mutations in NLRP3, thus defining NLRP3 as a critical component of the inflammatory process. NLRP3 has also been implicated in the pathogenesis of a number of complex diseases, notably including metabolic disorders such as type 2 diabetes, atherosclerosis, obesity and gout.

A role for NLRP3 in diseases of the central nervous system is emerging, and lung diseases have also been shown to be influenced by NLRP3. Furthermore, NLRP3 has a role in the development of liver disease, kidney disease and aging. Many of these associations were defined using NLRP3 KO mice, but there have also been insights into the specific activation of NLRP3 in these diseases. In Type 2 diabetes mellitus (T2D), the deposition of islet amyloid polypeptide in the pancreas activates NLRP3 and IL-ιβ signaling, resulting in cell death and inflammation.

Current treatments for NLRP3-related diseases include biologic agents that target IL-1. These are the recombinant IL-1 receptor antagonist anakinra, the neutralizing IL-1β antibody canakinumab and the soluble decoy IL1 receptor rilonacept. These approaches have proven successful in the treatment of CAPS, and these biologic agents have been used in clinical trials for other IL-1β associated diseases. Small molecule inhibitors of NLRP3 provide an attractive alternative to these biologics, given their potential for improved safety (minimal risk of infection and ease of withdrawal compared to biologics) and patient comfort and compliance.

The compounds of Formula (I'), (I), or (Ia) described herein are NLRP3 modulators. The compounds of Formula (I'), (I), or (Ia) described herein, and compositions comprising these compounds, are useful for the treatment of NLRP3 associated diseases including, but not limited to, type 2 diabetes, atherosclerosis, obesity and gout.

In some embodiments, provided herein is a compound of Formula (I'), or a pharmaceutically acceptable salt or solvate thereof:

Formula (I')

wherein:
- $X_1$ is O, S, or $N(R_3)$;
- $X_2$ is $-N(R_4)-$ or $-C(R_4)_2-$;
- $X_3$ is $-N(R_5)-$ or $-C(R_5)_2-$;
- $Y_1$ is O, S, or $N(R_8)$;
- $Y_2$ is N or $C(R_9)$;
- $Z_1$ is O, S, $N(R_3)$, or $-C(R_{17})=C(R_{17})-$;
- $Z_2$ is N or $C(R_{19})$;
- $R_1$ is $R_2$ is $R_3$ is hydrogen, $-OR_{14}$, $-CN$, $-NO_2$, or $-S(=O)_2R_{15}$;

each $R_4$ is independently selected from hydrogen, $C_1$-$C_6$alkyl, $-C_1$-$C_6$alkyl-$OR_7$, and $-C_1$-$C_6$alkyl-$N(R_7)_2$;

each $R_5$ is independently selected from hydrogen, $C_1$-$C_6$alkyl, $-C_1$-$C_6$alkyl-$OR_7$, and $-C_1$-$C_6$alkyl-$N(R_7)_2$;

each $R_6$ is independently selected from $C_1$-$C_6$alkyl, $-C_1$-$C_6$alkyl-$CO_2R_{18}$, $C_1$-$C_6$haloalkyl, $-C_1$-$C_6$alkyl-$OR_7$, and $-C_1$-$C_6$alkyl-$N(R_7)_2$;

each $R_7$ is independently selected from hydrogen and $C_1$-$C_6$alkyl;

$R_8$ is hydrogen, $C_1$-$C_6$alkyl, $-C_1$-$C_6$alkyl-$OR_7$, $-C_1$-$C_6$alkyl-$N(R_7)_2$, or $C_3$-$C_6$cycloalkyl;

$R_9$ is hydrogen, halogen, $C_1$-$C_6$alkyl, $C_1$-$C_6$haloalkyl, or $C_3$-$C_6$cycloalkyl;

$R_{10}$ is hydrogen, halogen, $C_1$-$C_6$alkyl, $C_1$-$C_6$haloalkyl, $-C_1$-$C_6$alkyl-$OR_7$, or $-C_1$-$C_6$alkyl-$N(R_7)_2$;

$R_{11}$ and $R_{12}$ are independently selected from hydrogen, halogen, $C_1$-$C_6$alkyl, $C_1$-$C_6$haloalkyl, $-C_1$-$C_6$alkyl-$OR_7$, and $-C_1$-$C_6$alkyl-$N(R_7)_2$; or $R_{11}$ and $R_{12}$ are combined to form a 5- or 6-membered cycloalkyl ring;

$R_{13}$ is hydrogen, $C_1$-$C_6$alkyl, $C_1$-$C_6$haloalkyl, $C_2$-$C_6$alkenyl, $C_2$-$C_6$alkynyl, $C_3$-$C_5$cycloalkyl, $C_2$-$C_9$heterocycloalkyl, phenyl, or $C_2$-$C_9$heteroaryl, wherein $C_3$-$C_5$cycloalkyl, $C_2$-$C_9$heterocycloalkyl, phenyl, and $C_2$-$C_9$heteroaryl are optionally substituted by 1, 2, 3, or 4 $R_{16}$;

$R_{14}$ is hydrogen or $C_1$-$C_6$alkyl;

$R_{15}$ is $C_1$-$C_6$alkyl;

each $R_{16}$ is independently selected from halogen, $C_1$-$C_6$alkyl, $C_1$-$C_6$haloalkyl, $C_1$-$C_6$alkoxy, $C_1$-$C_6$haloalkoxy, $C_3$-$C_6$cycloalkyl, $C_2$-$C_9$heterocycloalkyl, $C_6$-$C_{10}$aryl, $C_2$-$C_9$heteroaryl, wherein $C_3$-$C_6$cycloalkyl, $C_2$-$C_9$heterocycloalkyl, $C_6$-$C_{10}$aryl, $C_2$-$C_9$heteroaryl are optionally substituted with 1, 2, or 3 groups selected from halogen, $C_1$-$C_6$alkyl, $C_1$-$C_6$haloalkyl, $C_1$-$C_6$alkoxy, and $C_1$-$C_6$haloalkoxy;

each $R_{17}$ is independently selected from hydrogen, halogen, $C_1$-$C_6$alkyl, $C_1$-$C_6$haloalkyl, —$C_1$-$C_6$alkyl-O$R_7$, and —$C_1$-$C_6$alkyl-N($R_7$)$_2$;

$R_{18}$ is hydrogen or $C_1$-$C_6$alkyl;

$R_{19}$ is hydrogen, halogen, —CN, $C_1$-$C_6$alkyl, $C_1$-$C_6$haloalkyl, —$C_1$-$C_6$alkyl-O$R_7$, or —$C_1$-$C_6$alkyl-N($R_7$)$_2$;

m is 0, 1, or 2;
n is 1, 2, or 3;
p is 0, 1, or 2;
q is 0, 1, 2, 3, or 4;
s is 1, 2, or 3; and
t is 1, 2, or 3.

In some embodiments is a compound of Formula (I'), or a pharmaceutically acceptable salt or solvate thereof, wherein $R_1$ is

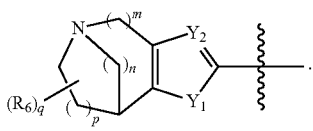

In some embodiments is a compound of Formula (I'), or a pharmaceutically acceptable salt or solvate thereof, wherein $R_1$ is

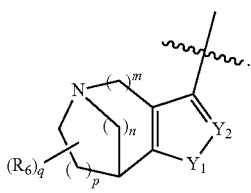

In some embodiments is a compound of Formula (I'), or a pharmaceutically acceptable salt or solvate thereof, wherein $R_1$ is

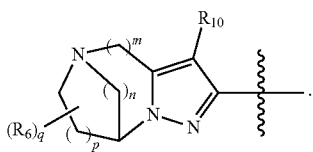

In some embodiments is a compound of Formula (F), or a pharmaceutically acceptable salt or solvate thereof, wherein $R_1$ is

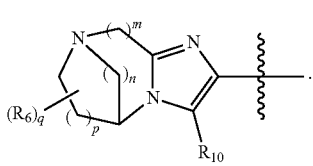

In some embodiments is a compound of Formula (I'), or a pharmaceutically acceptable salt or solvate thereof, wherein $R_1$ is

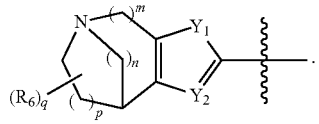

In some embodiments is a compound of Formula (I'), or a pharmaceutically acceptable salt or solvate thereof, wherein m is 1. In some embodiments is a compound of Formula (I'), or a pharmaceutically acceptable salt or solvate thereof, wherein m is 0. In some embodiments is a compound of Formula (I'), or a pharmaceutically acceptable salt or solvate thereof, wherein m is 2.

In some embodiments is a compound of Formula (I'), or a pharmaceutically acceptable salt or solvate thereof, wherein p is 1. In some embodiments is a compound of Formula (I'), or a pharmaceutically acceptable salt or solvate thereof, wherein p is 0. In some embodiments is a compound of Formula (I'), or a pharmaceutically acceptable salt or solvate thereof, wherein p is 2.

In some embodiments is a compound of Formula (I'), or a pharmaceutically acceptable salt or solvate thereof, wherein m is 1 and p is 1.

In some embodiments is a compound of Formula (I'), or a pharmaceutically acceptable salt or solvate thereof, wherein each $R_7$ is independently selected from $C_1$-$C_6$alkyl, —$C_1$-$C_6$alkyl-CO$_2$$R_{18}$, $C_1$-$C_6$haloalkyl, and $C_1$-$C_6$heteroalkyl. In some embodiments is a compound of Formula (I'), or a pharmaceutically acceptable salt or solvate thereof, wherein each $R_7$ is independently selected from $C_1$-$C_6$alkyl, —$C_1$-$C_6$alkyl-CO$_2$$R_{18}$, and $C_1$-$C_6$haloalkyl. In some embodiments is a compound of Formula (I'), or a pharmaceutically acceptable salt or solvate thereof, wherein each $R_7$ is independently selected from $C_1$-$C_6$alkyl. In some embodiments is a compound of Formula (I'), or a pharmaceutically acceptable salt or solvate thereof, wherein each $R_7$ is —CH$_3$.

In some embodiments, provided herein is a compound of Formula (I'), or a pharmaceutically acceptable salt or solvate thereof, wherein q is 0, 1, 2, or 3. In some embodiments, provided herein is a compound of Formula (I'), or a pharmaceutically acceptable salt or solvate thereof, wherein q is 0. In some embodiments, provided herein is a compound of Formula (I'), or a pharmaceutically acceptable salt or solvate thereof, wherein q is 1. In some embodiments, provided herein is a compound of Formula (I'), or a pharmaceutically acceptable salt or solvate thereof, wherein q is 2. In some embodiments, provided herein is a compound of Formula (I'), or a pharmaceutically acceptable salt or solvate thereof, wherein q is 3. In some embodiments, provided herein is a compound of Formula (I'), or a pharmaceutically acceptable salt or solvate thereof, wherein q is 4.

In some embodiments is a compound of Formula (I'), or a pharmaceutically acceptable salt or solvate thereof, wherein $R_1$ is

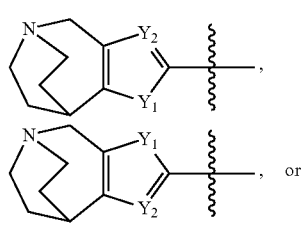

-continued

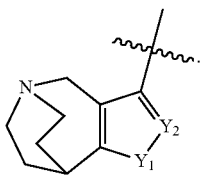

In some embodiments, provided herein is a compound of Formula (I'), or a pharmaceutically acceptable salt or solvate thereof, wherein $Y_1$ is O. In some embodiments, provided herein is a compound of Formula (I'), or a pharmaceutically acceptable salt or solvate thereof, wherein $Y_1$ is S. In some embodiments, provided herein is a compound of Formula (I'), or a pharmaceutically acceptable salt or solvate thereof, wherein $Y_1$ is $N(R_8)$. In some embodiments, provided herein is a compound of Formula (I'), or a pharmaceutically acceptable salt or solvate thereof, wherein $Y_1$ is $N(R_8)$ and $R_8$ is hydrogen or $C_1$-$C_6$alkyl.

In some embodiments, provided herein is a compound of Formula (I'), or a pharmaceutically acceptable salt or solvate thereof, wherein $Y_2$ is N. In some embodiments, provided herein is a compound of Formula (I'), or a pharmaceutically acceptable salt or solvate thereof, wherein $Y_2$ is $C(R_9)$. In some embodiments, provided herein is a compound of Formula (I'), or a pharmaceutically acceptable salt or solvate thereof, wherein $Y_2$ is $C(R_9)$ and $R_9$ is selected from hydrogen and $C_1$-$C_6$alkyl. In some embodiments, provided herein is a compound of Formula (I'), or a pharmaceutically acceptable salt or solvate thereof, wherein $Y_2$ is $C(R_9)$ and $R_9$ is hydrogen. In some embodiments, provided herein is a compound of Formula (I'), or a pharmaceutically acceptable salt or solvate thereof, wherein $Y_2$ is $C(R_9)$ and $R_9$ is $C_1$-$C_6$alkyl.

In some embodiments, provided herein is a compound of Formula (I'), or a pharmaceutically acceptable salt or solvate thereof, wherein $R_1$ is

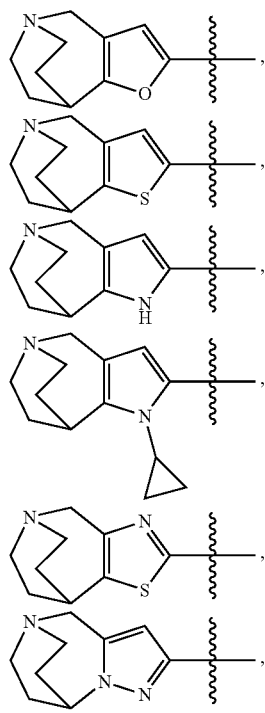

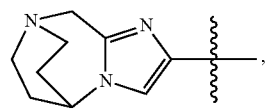

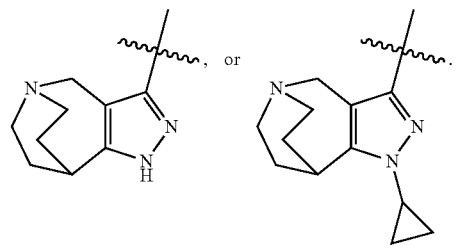

In some embodiments, provided herein is a compound of Formula (I'), or a pharmaceutically acceptable salt or solvate thereof, wherein $R_1$ is

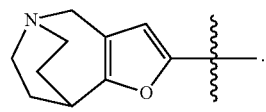 [SMILES: *c1cc2c(o1)C1CCN(CC1)C2]

In some embodiments, provided herein is a compound of Formula (I'), or a pharmaceutically acceptable salt or solvate thereof, wherein $R_1$ is

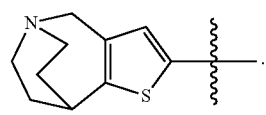 [SMILES: *c1cc2c(s1)C1CCN(CC1)C2]

In some embodiments, provided herein is a compound of Formula (I'), or a pharmaceutically acceptable salt or solvate thereof, wherein $R_1$ is

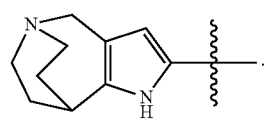 [SMILES: *c1cc2c([nH]1)C1CCN(CC1)C2]

In some embodiments, provided herein is a compound of Formula (I'), or a pharmaceutically acceptable salt or solvate thereof, wherein $R_1$ is

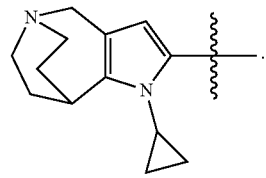 [SMILES: *c1cc2c(n1C1CC1)C1CCN(CC1)C2]

In some embodiments, provided herein is a compound of Formula (I'), or a pharmaceutically acceptable salt or solvate thereof, wherein $R_1$ is

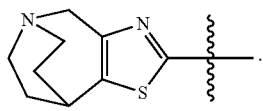 [SMILES: *c1nc2c(s1)C1CCN(CC1)C2]

In some embodiments, provided herein is a compound of Formula (I'), or a pharmaceutically acceptable salt or solvate thereof, wherein $R_1$ is

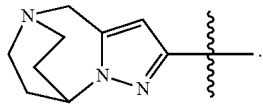 [SMILES: *c1cc2n(n1)C1CCN(CC1)C2]

In some embodiments, provided herein is a compound of Formula (I'), or a pharmaceutically acceptable salt or solvate thereof, wherein $R_1$ is

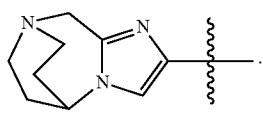 [SMILES: *c1cn2c(n1)CN1CCC2CC1]

In some embodiments, provided herein is a compound of Formula (I'), or a pharmaceutically acceptable salt or solvate thereof, wherein $R_1$ is

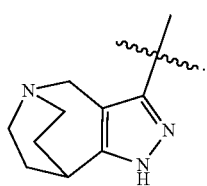 [SMILES: *c1n[nH]c2c1CN1CCC2CC1]

In some embodiments, provided herein is a compound of Formula (I'), or a pharmaceutically acceptable salt or solvate thereof, wherein $R_1$ is

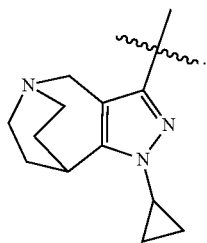 [SMILES: *c1nn(C2CC2)c2c1CN1CCC2CC1]

In some embodiments, provided herein is a compound of Formula (I'), or a pharmaceutically acceptable salt or solvate thereof, wherein $R_2$ is

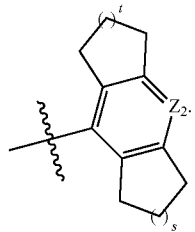

In some embodiments, provided herein is a compound of Formula (I'), or a pharmaceutically acceptable salt or solvate thereof, wherein $R_2$ is

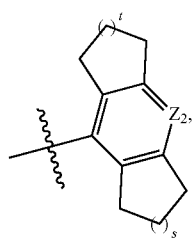

$s$ is 1, and $t$ is 1. In some embodiments, provided herein is a compound of Formula (I'), or a pharmaceutically acceptable salt or solvate thereof, wherein $R_2$ is

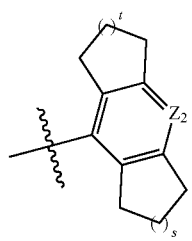

$s$ is 1, $t$ is 1, and $Z_2$ is $C(R_{19})$. In some embodiments, provided herein is a compound of Formula (I'), or a pharmaceutically acceptable salt or solvate thereof, wherein $R_2$ is

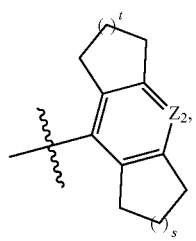

$s$ is 1, $t$ is 1, and $Z_2$ is $C(H)$. In some embodiments, provided herein is a compound of Formula (I'), or a pharmaceutically acceptable salt or solvate thereof, wherein $R_2$ is

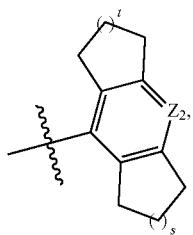

s is 1, t is 1, and $Z_2$ is N.

In some embodiments, provided herein is a compound of Formula (I'), or a pharmaceutically acceptable salt or solvate thereof, wherein $R_2$ is

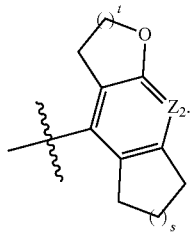

In some embodiments, provided herein is a compound of Formula (I'), or a pharmaceutically acceptable salt or solvate thereof, wherein $R_2$ is

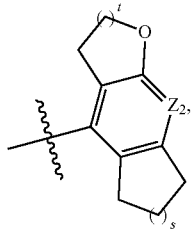

s is 1, and t is 1. In some embodiments, provided herein is a compound of Formula (I'), or a pharmaceutically acceptable salt or solvate thereof, wherein $R_2$ is

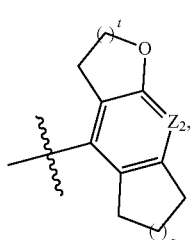

s is 1, t is 1, and $Z_2$ is $C(R_{19})$. In some embodiments, provided herein is a compound of Formula (I'), or a pharmaceutically acceptable salt or solvate thereof, wherein $R_2$ is

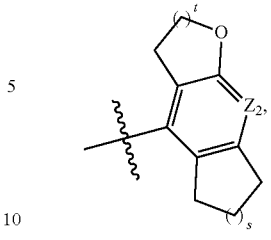

s is 1, t is 1, and $Z_2$ is C(H). In some embodiments, provided herein is a compound of Formula (I'), or a pharmaceutically acceptable salt or solvate thereof, wherein $R_2$ is

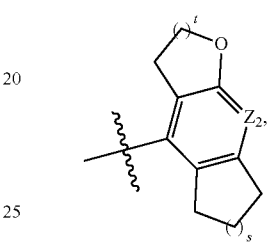

s is 1, t is 1, and $Z_2$ is N.

In some embodiments, provided herein is a compound of Formula (I'), or a pharmaceutically acceptable salt or solvate thereof, wherein $R_2$ is

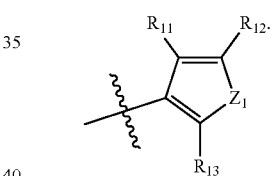

In some embodiments, provided herein is a compound of Formula (I'), or a pharmaceutically acceptable salt or solvate thereof, wherein $R_2$ is

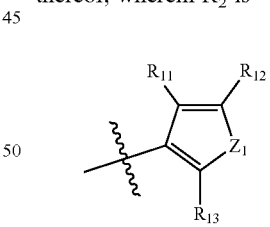

and $Z_1$ is S. In some embodiments, provided herein is a compound of Formula (I'), or a pharmaceutically acceptable salt or solvate thereof, wherein $R_2$ is

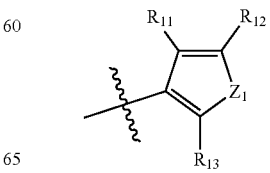

and $Z_1$ is —C($R_{17}$)=C($R_{17}$)—. In some embodiments, provided herein is a compound of Formula (I'), or a pharmaceutically acceptable salt or solvate thereof, wherein $R_2$ is

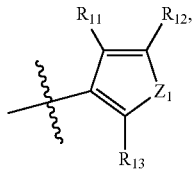

$Z_1$ is —C($R_{17}$)=C($R_{17}$)—, and each $R_{17}$ is independently selected from hydrogen and halogen. In some embodiments, provided herein is a compound of Formula (I'), or a pharmaceutically acceptable salt or solvate thereof, wherein $R_2$ is

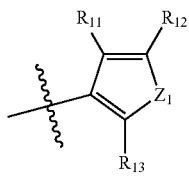

and $Z_1$ is —C(H)=C(H)—. In some embodiments, provided herein is a compound of Formula (I'), or a pharmaceutically acceptable salt or solvate thereof, wherein $R_2$ is

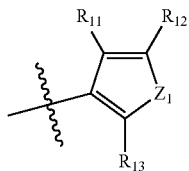

and $R_{11}$ and $R_{12}$ are combined to form a 5- or 6-membered cycloalkyl ring. In some embodiments, provided herein is a compound of Formula (I'), or a pharmaceutically acceptable salt or solvate thereof, wherein $R_2$ is

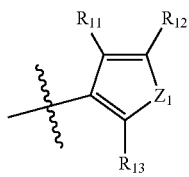

and $R_{11}$ and $R_{12}$ are combined to form a 5-membered cycloalkyl ring. In some embodiments, provided herein is a compound of Formula (I'), or a pharmaceutically acceptable salt or solvate thereof, wherein $R_2$ is

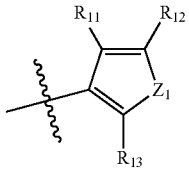

and $R_{11}$ and $R_{12}$ are independently selected from hydrogen, halogen, and $C_1$-$C_6$alkyl. In some embodiments, provided herein is a compound of Formula (I'), or a pharmaceutically acceptable salt or solvate thereof, wherein $R_2$ is

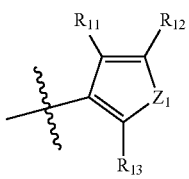

and $R_{13}$ is $C_2$-$C_9$heteroaryl optionally substituted by 1, 2, or 3 $R_{16}$. In some embodiments, provided herein is a compound of Formula (I'), or a pharmaceutically acceptable salt or solvate thereof, wherein $R_2$ is

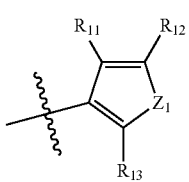

and $R_{13}$ is pyridyl optionally substituted by 1 or 2 $R_{16}$. In some embodiments, provided herein is a compound of Formula (I'), or a pharmaceutically acceptable salt or solvate thereof, wherein $R_2$ is

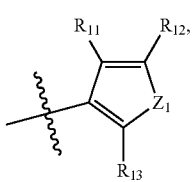

$R_{13}$ is pyridyl optionally substituted by 1 or 2 $R_{16}$, and each $R_{16}$ is independently selected from halogen, $C_1$-$C_6$alkyl, $C_1$-$C_6$haloalkyl, and $C_1$-$C_6$alkoxy. In some embodiments, provided herein is a compound of Formula (I'), or a pharmaceutically acceptable salt or solvate thereof, wherein $R_2$ is

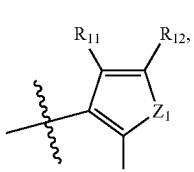

$R_{13}$ is pyridyl optionally substituted by 1 $R_{16}$, and $R_{16}$ is selected from halogen, $C_1$-$C_6$alkyl, $C_1$-$C_6$haloalkyl, and $C_1$-$C_6$alkoxy. In some embodiments, provided herein is a compound of Formula (I'), or a pharmaceutically acceptable salt or solvate thereof, wherein $R_2$ is

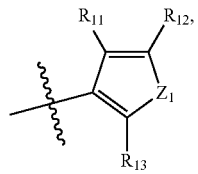

$R_{13}$ is pyridyl optionally substituted by 1 $R_{16}$, and $R_{16}$ is $C_1$-$C_6$alkoxy. In some embodiments, provided herein is a compound of Formula (I'), or a pharmaceutically acceptable salt or solvate thereof, wherein $R_2$ is

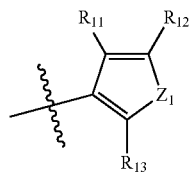

and $R_{13}$ is hydrogen, $C_1$-$C_6$alkyl, $C_1$-$C_6$haloalkyl, $C_3$-$C_5$cycloalkyl, or $C_2$-$C_9$heterocycloalkyl. In some embodiments, provided herein is a compound of Formula (I'), or a pharmaceutically acceptable salt or solvate thereof, wherein $R_2$ is

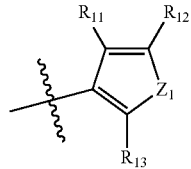

and $R_{13}$ is $C_1$-$C_6$alkyl. In some embodiments, provided herein is a compound of Formula (I'), or a pharmaceutically acceptable salt or solvate thereof, wherein $R_2$ is

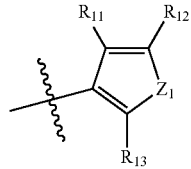

and $R_{13}$ is $C_1$-$C_6$haloalkyl. In some embodiments, provided herein is a compound of Formula (I'), or a pharmaceutically acceptable salt or solvate thereof, wherein $R_2$ is

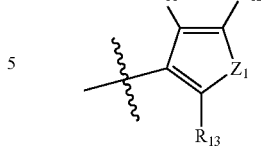

and $R_{13}$ is $C_3$-$C_5$cycloalkyl.

In some embodiments, provided herein is a compound of Formula (I'), or a pharmaceutically acceptable salt or solvate thereof, wherein $R_2$ is

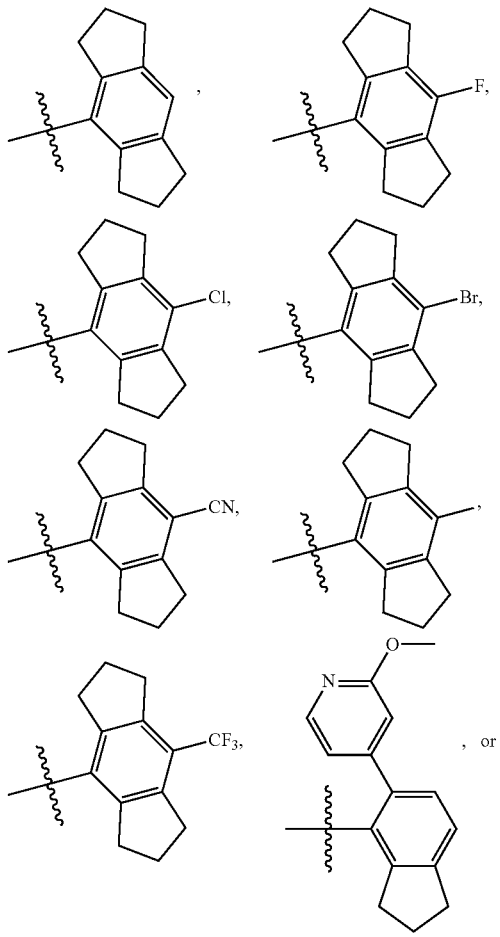

In some embodiments, provided herein is a compound of Formula (I'), or a pharmaceutically acceptable salt or solvate thereof, wherein $R_2$ is

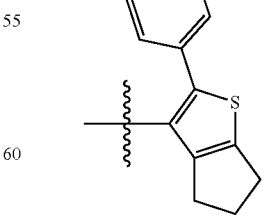

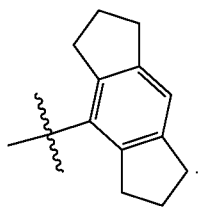 [SMILES: *c1c2c(cc3c1CCC3)CCC2]

In some embodiments, provided herein is a compound of Formula (I'), or a pharmaceutically acceptable salt or solvate thereof, wherein $R_2$ is

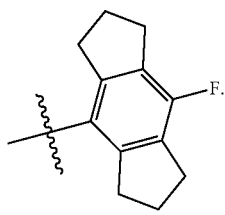 [SMILES: *c1c2c(c(F)c3c1CCC3)CCC2]

In some embodiments, provided herein is a compound of Formula (I'), or a pharmaceutically acceptable salt or solvate thereof, wherein $R_2$ is

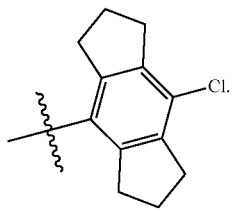 [SMILES: *c1c2c(c(Cl)c3c1CCC3)CCC2]

In some embodiments, provided herein is a compound of Formula (I'), or a pharmaceutically acceptable salt or solvate thereof, wherein $R_2$ is

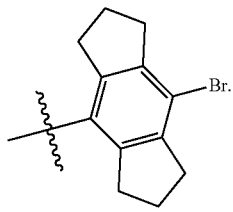 [SMILES: *c1c2c(c(Br)c3c1CCC3)CCC2]

In some embodiments, provided herein is a compound of Formula (I'), or a pharmaceutically acceptable salt or solvate thereof, wherein $R_2$ is

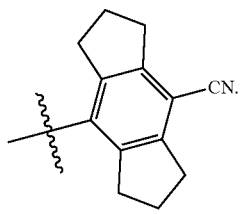 [SMILES: *c1c2c(c(C#N)c3c1CCC3)CCC2]

In some embodiments, provided herein is a compound of Formula (I'), or a pharmaceutically acceptable salt or solvate thereof, wherein $R_2$ is

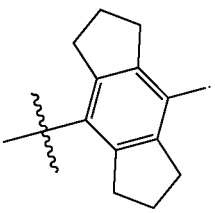

In some embodiments, provided herein is a compound of Formula (I'), or a pharmaceutically acceptable salt or solvate thereof, wherein $R_2$ is

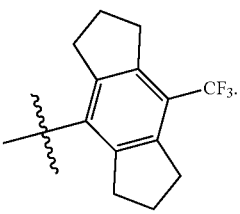 [SMILES: *c1c2c(c(C(F)(F)F)c3c1CCC3)CCC2]

In some embodiments, provided herein is a compound of Formula (I'), or a pharmaceutically acceptable salt or solvate thereof, wherein $R_2$ is

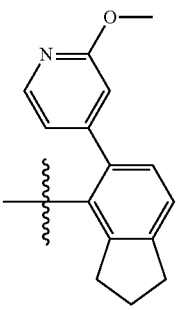

In some embodiments, provided herein is a compound of Formula (I'), or a pharmaceutically acceptable salt or solvate thereof, wherein $R_2$ is

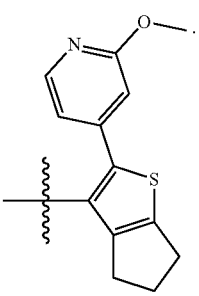 [SMILES: *c1c(-c2ccnc(OC)c2)sc2c1CCC2]

In some embodiments, provided herein is a compound of Formula (I'), or a pharmaceutically acceptable salt or solvate thereof, wherein $R_2$ is

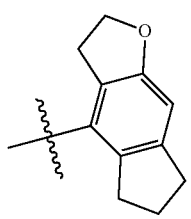

In some embodiments, provided herein is a compound of Formula (I'), or a pharmaceutically acceptable salt or solvate thereof, wherein $R_2$ is

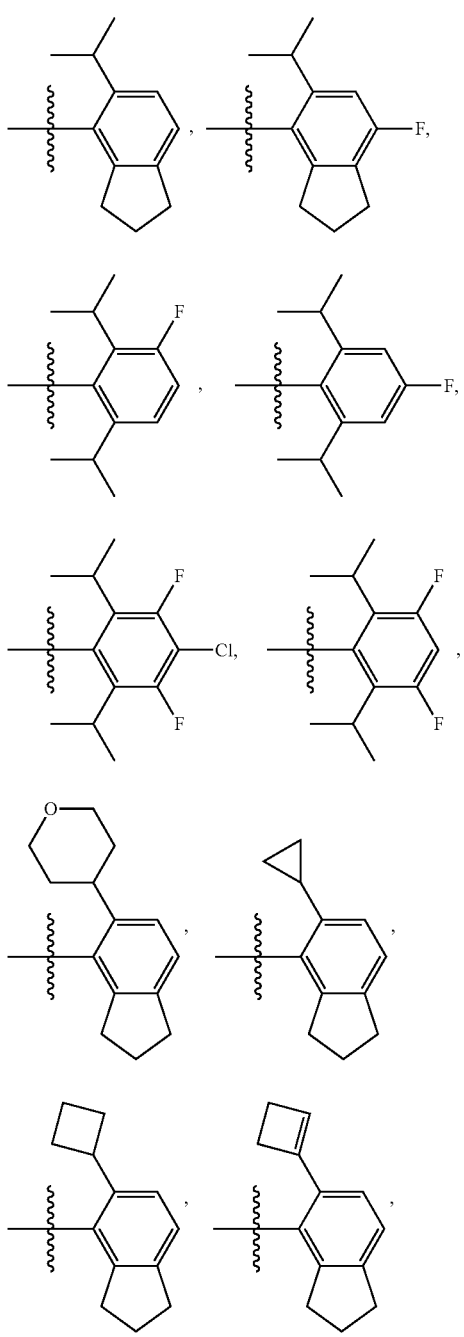

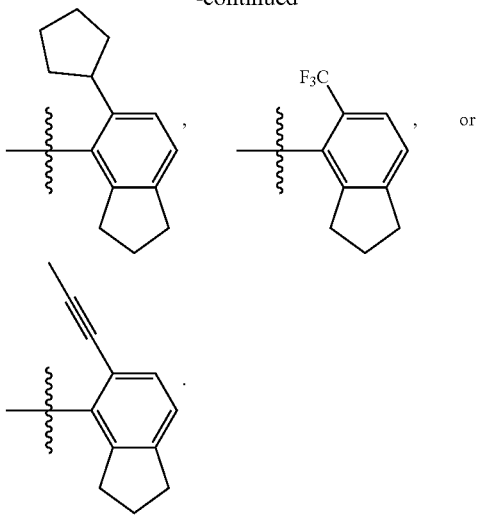

In some embodiments, provided herein is a compound of Formula (I'), or a pharmaceutically acceptable salt or solvate thereof, wherein $X_2$ is —N($R_5$)—. In some embodiments, provided herein is a compound of Formula (I'), or a pharmaceutically acceptable salt or solvate thereof, wherein $X_2$ is —N($R_5$)— and $R_5$ is hydrogen. In some embodiments, provided herein is a compound of Formula (I'), or a pharmaceutically acceptable salt or solvate thereof, wherein $X_2$ is —N($R_5$)— and $R_5$ is $C_1$-$C_6$alkyl. In some embodiments, provided herein is a compound of Formula (I'), or a pharmaceutically acceptable salt or solvate thereof, wherein $X_2$ is —C($R_5$)$_2$—. In some embodiments, provided herein is a compound of Formula (I'), or a pharmaceutically acceptable salt or solvate thereof, wherein $X_2$ is —C($R_5$)$_2$— and each $R_5$ is hydrogen.

In some embodiments, provided herein is a compound of Formula (I'), or a pharmaceutically acceptable salt or solvate thereof, wherein $X_3$ is —N($R_5$)—. In some embodiments, provided herein is a compound of Formula (I'), or a pharmaceutically acceptable salt or solvate thereof, wherein $X_3$ is —N($R_5$)— and $R_5$ is hydrogen. In some embodiments, provided herein is a compound of Formula (I'), or a pharmaceutically acceptable salt or solvate thereof, wherein $X_3$ is —N($R_5$)— and $R_5$ is $C_1$-$C_6$alkyl. In some embodiments, provided herein is a compound of Formula (I'), or a pharmaceutically acceptable salt or solvate thereof, wherein $X_3$ is —C($R_5$)$_2$—. In some embodiments, provided herein is a compound of Formula (I'), or a pharmaceutically acceptable salt or solvate thereof, wherein $X_3$ is —C($R_5$)$_2$— and each $R_5$ is hydrogen.

In some embodiments, provided herein is a compound of Formula (I'), or a pharmaceutically acceptable salt or solvate thereof, wherein $X_1$ is O. In some embodiments, provided herein is a compound of Formula (I'), or a pharmaceutically acceptable salt or solvate thereof, wherein $X_1$ is S. In some embodiments, provided herein is a compound of Formula (I'), or a pharmaceutically acceptable salt or solvate thereof, wherein $X_1$ is N($R_3$). In some embodiments, provided herein is a compound of Formula (I'), or a pharmaceutically acceptable salt or solvate thereof, wherein $X_1$ is C(NO$_2$)($R_4$).

In some embodiments, provided herein is a compound of Formula (I), or a pharmaceutically acceptable salt or solvate thereof:

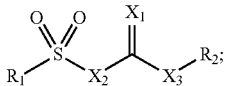 Formula (I)

wherein:
X$_1$ is O, S, or N(R$_3$);
X$_2$ is —N(R$_4$)— or —C(R$_4$)$_2$—;
X$_3$ is —N(R$_5$)— or —C(R$_5$)$_2$—;
Y$_1$ is O, S, or N(R$_8$);
Y$_2$ is N or C(R$_9$);
Z$_1$ is O, S, N(R$_3$), or —C(R$_{17}$)=C(R$_{17}$)—;
Z$_2$ is N or C(R$_{19}$);
R$_1$ is

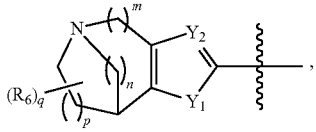,

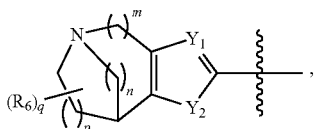,

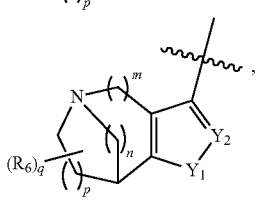,

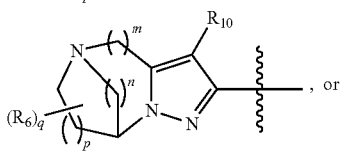, or

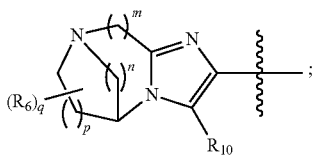;

R$_2$ is

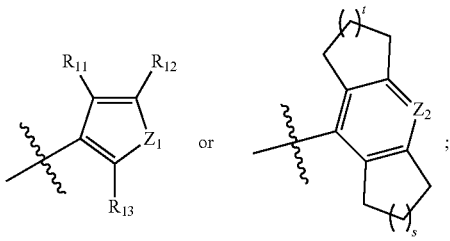 or 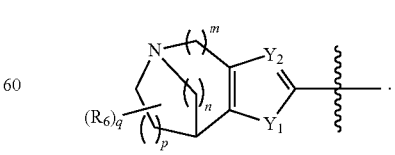;

R$_3$ is hydrogen, —OR$_{14}$, —CN, —NO$_2$, or —S(=O)$_2$R$_{15}$;

each R$_4$ is independently selected from hydrogen, C$_1$-C$_6$alkyl, —C$_1$-C$_6$alkyl-OR$_7$, and —C$_1$-C$_6$alkyl-N(R$_7$)$_2$;

each R$_5$ is independently selected from hydrogen, C$_1$-C$_6$alkyl, —C$_1$-C$_6$alkyl-OR$_7$, and —C$_1$-C$_6$alkyl-N(R$_7$)$_2$;

each R$_6$ is independently selected from C$_1$-C$_6$alkyl, —C$_1$-C$_6$alkyl-CO$_2$R$_{18}$, C$_1$-C$_6$haloalkyl, —C$_1$-C$_6$alkyl-OR$_7$, and —C$_1$-C$_6$alkyl-N(R$_7$)$_2$;

each R$_7$ is independently selected from hydrogen and C$_1$-C$_6$alkyl;

R$_8$ is hydrogen, C$_1$-C$_6$alkyl, —C$_1$-C$_6$alkyl-OR$_7$, —C$_1$-C$_6$alkyl-N(R$_7$)$_2$, or C$_3$-C$_6$cycloalkyl;

R$_9$ is hydrogen, halogen, C$_1$-C$_6$alkyl, C$_1$-C$_6$haloalkyl, or C$_3$-C$_6$cycloalkyl;

R$_{10}$ is hydrogen, halogen, C$_1$-C$_6$alkyl, C$_1$-C$_6$haloalkyl, —C$_1$-C$_6$alkyl-OR$_7$, or —C$_1$-C$_6$alkyl-N(R$_7$)$_2$;

R$_{11}$ and R$_{12}$ are independently selected from halogen, C$_1$-C$_6$alkyl, C$_1$-C$_6$haloalkyl, —C$_1$-C$_6$alkyl-OR$_7$, and —C$_1$-C$_6$alkyl-N(R$_7$)$_2$; or R$_{11}$ and R$_{12}$ are combined to form a 5- or 6-membered cycloalkyl ring;

R$_{13}$ is phenyl or C$_2$-C$_9$heteroaryl, wherein phenyl and C$_2$-C$_9$heteroaryl are optionally substituted by 1, 2, 3, or 4 R$_{16}$;

R$_{14}$ is hydrogen or C$_1$-C$_6$alkyl;

R$_{15}$ is C$_1$-C$_6$alkyl;

each R$_{16}$ is independently selected from halogen, C$_1$-C$_6$alkyl, C$_1$-C$_6$haloalkyl, C$_1$-C$_6$alkoxy, C$_1$-C$_6$haloalkoxy, C$_3$-C$_6$cycloalkyl, C$_2$-C$_9$heterocycloalkyl, C$_6$-C$_{10}$aryl, C$_2$-C$_9$heteroaryl, wherein C$_3$-C$_6$cycloalkyl, C$_2$-C$_9$heterocycloalkyl, C$_6$-C$_{10}$aryl, C$_2$-C$_9$heteroaryl are optionally substituted with 1, 2, or 3 groups selected from halogen, C$_1$-C$_6$alkyl, C$_1$-C$_6$haloalkyl, C$_1$-C$_6$alkoxy, and C$_1$-C$_6$haloalkoxy;

each R$_{17}$ is independently selected from hydrogen, halogen, C$_1$-C$_6$alkyl, C$_1$-C$_6$haloalkyl, —C$_1$-C$_6$alkyl-OR$_7$, and —C$_1$-C$_6$alkyl-N(R$_7$)$_2$;

R$_{18}$ is hydrogen or C$_1$-C$_6$alkyl;

R$_{19}$ is hydrogen, halogen, —CN, C$_1$-C$_6$alkyl, C$_1$-C$_6$haloalkyl, —C$_1$-C$_6$alkyl-OR$_7$, or —C$_1$-C$_6$alkyl-N(R$_7$)$_2$;

m is 0, 1, or 2;
n is 1, 2, or 3;
p is 0, 1, or 2;
q is 0, 1, 2, 3, or 4;
s is 1, 2, or 3; and
t is 1, 2, or 3.

In some embodiments is a compound of Formula (I), or a pharmaceutically acceptable salt or solvate thereof, wherein R$_1$ is

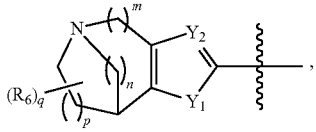.

In some embodiments is a compound of Formula (I), or a pharmaceutically acceptable salt or solvate thereof, wherein R$_1$ is

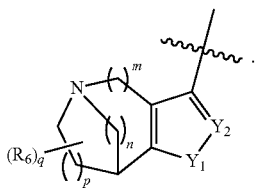

In some embodiments is a compound of Formula (I), or a pharmaceutically acceptable salt or solvate thereof, wherein $R_1$ is

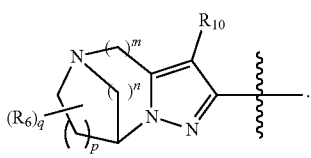

In some embodiments is a compound of Formula (I), or a pharmaceutically acceptable salt or solvate thereof, wherein $R_1$ is

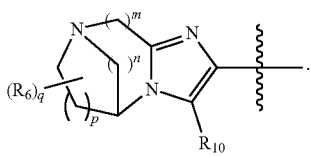

In some embodiments is a compound of Formula (I), or a pharmaceutically acceptable salt or solvate thereof, wherein $R_1$ is

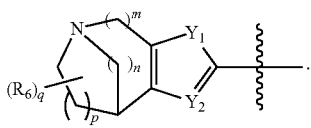

In some embodiments is a compound of Formula (I), or a pharmaceutically acceptable salt or solvate thereof, wherein m is 1. In some embodiments is a compound of Formula (I), or a pharmaceutically acceptable salt or solvate thereof, wherein m is 0. In some embodiments is a compound of Formula (I), or a pharmaceutically acceptable salt or solvate thereof, wherein m is 2.

In some embodiments is a compound of Formula (I), or a pharmaceutically acceptable salt or solvate thereof, wherein p is 1. In some embodiments is a compound of Formula (I), or a pharmaceutically acceptable salt or solvate thereof, wherein p is 0. In some embodiments is a compound of Formula (I), or a pharmaceutically acceptable salt or solvate thereof, wherein p is 2.

In some embodiments is a compound of Formula (I), or a pharmaceutically acceptable salt or solvate thereof, wherein m is 1 and p is 1.

In some embodiments is a compound of Formula (I), or a pharmaceutically acceptable salt or solvate thereof, wherein each $R_7$ is independently selected from $C_1$-$C_6$alkyl, —$C_1$-$C_6$alkyl-$CO_2R_{18}$, $C_1$-$C_6$haloalkyl, and $C_1$-$C_6$heteroalkyl. In some embodiments is a compound of Formula (I), or a pharmaceutically acceptable salt or solvate thereof, wherein each $R_7$ is independently selected from $C_1$-$C_6$alkyl, —$C_1$-$C_6$alkyl-$CO_2R_{18}$, and $C_1$-$C_6$haloalkyl. In some embodiments is a compound of Formula (I), or a pharmaceutically acceptable salt or solvate thereof, wherein each $R_7$ is independently selected from $C_1$-$C_6$alkyl. In some embodiments is a compound of Formula (I), or a pharmaceutically acceptable salt or solvate thereof, wherein each $R_7$ is —$CH_3$.

In some embodiments, provided herein is a compound of Formula (I), or a pharmaceutically acceptable salt or solvate thereof, wherein q is 0, 1, 2, or 3. In some embodiments, provided herein is a compound of Formula (I), or a pharmaceutically acceptable salt or solvate thereof, wherein q is 0. In some embodiments, provided herein is a compound of Formula (I), or a pharmaceutically acceptable salt or solvate thereof, wherein q is 1. In some embodiments, provided herein is a compound of Formula (I), or a pharmaceutically acceptable salt or solvate thereof, wherein q is 2. In some embodiments, provided herein is a compound of Formula (I), or a pharmaceutically acceptable salt or solvate thereof, wherein q is 3. In some embodiments, provided herein is a compound of Formula (I), or a pharmaceutically acceptable salt or solvate thereof, wherein q is 4.

In some embodiments is a compound of Formula (I), or a pharmaceutically acceptable salt or solvate thereof, wherein $R_1$ is

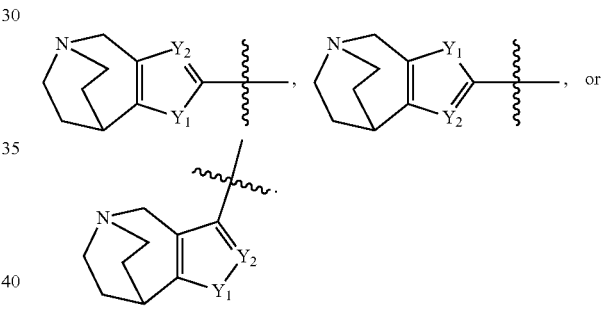

In some embodiments, provided herein is a compound of Formula (I), or a pharmaceutically acceptable salt or solvate thereof, wherein $Y_1$ is O. In some embodiments, provided herein is a compound of Formula (I), or a pharmaceutically acceptable salt or solvate thereof, wherein $Y_1$ is S. In some embodiments, provided herein is a compound of Formula (I), or a pharmaceutically acceptable salt or solvate thereof, wherein $Y_1$ is $N(R_8)$. In some embodiments, provided herein is a compound of Formula (I), or a pharmaceutically acceptable salt or solvate thereof, wherein $Y_1$ is $N(R_8)$ and $R_8$ is hydrogen or $C_1$-$C_6$alkyl.

In some embodiments, provided herein is a compound of Formula (I), or a pharmaceutically acceptable salt or solvate thereof, wherein $Y_2$ is N. In some embodiments, provided herein is a compound of Formula (I), or a pharmaceutically acceptable salt or solvate thereof, wherein $Y_2$ is $C(R_9)$. In some embodiments, provided herein is a compound of Formula (I), or a pharmaceutically acceptable salt or solvate thereof, wherein $Y_2$ is $C(R_9)$ and $R_9$ is selected from hydrogen and $C_1$-$C_6$alkyl. In some embodiments, provided herein is a compound of Formula (I), or a pharmaceutically acceptable salt or solvate thereof, wherein $Y_2$ is $C(R_9)$ and $R_9$ is hydrogen. In some embodiments, provided herein is a compound of Formula (I), or a pharmaceutically acceptable salt or solvate thereof, wherein $Y_2$ is $C(R_9)$ and $R_9$ is $C_1$-$C_6$alkyl.

In some embodiments, provided herein is a compound of Formula (I), or a pharmaceutically acceptable salt or solvate thereof, wherein $R_1$ is

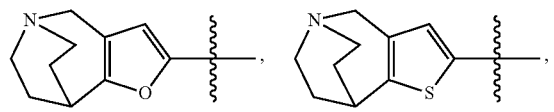

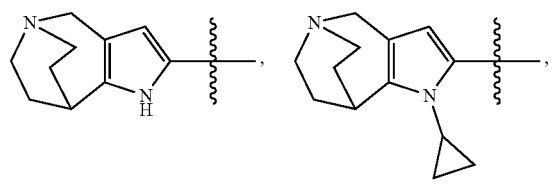

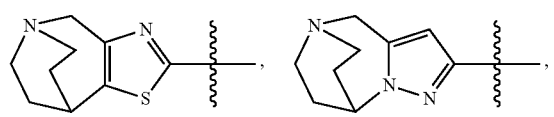

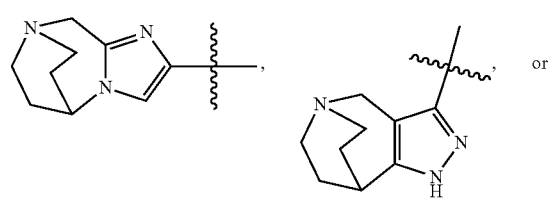 or

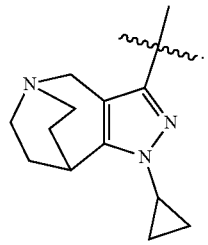

In some embodiments, provided herein is a compound of Formula (I), or a pharmaceutically acceptable salt or solvate thereof, wherein $R_1$ is

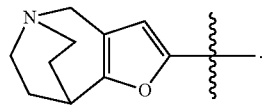 [SMILES: *c1cc2c(o1)C1CCN(CC1)C2]

In some embodiments, provided herein is a compound of Formula (I), or a pharmaceutically acceptable salt or solvate thereof, wherein $R_1$ is

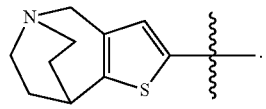 [SMILES: *c1cc2c(s1)C1CCN(CC1)C2]

In some embodiments, provided herein is a compound of Formula (I), or a pharmaceutically acceptable salt or solvate thereof, wherein $R_1$ is

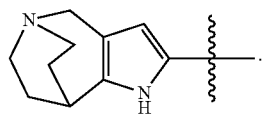 [SMILES: *c1cc2c([nH]1)C1CCN(CC1)C2]

In some embodiments, provided herein is a compound of Formula (I), or a pharmaceutically acceptable salt or solvate thereof, wherein $R_1$ is

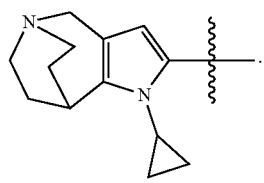 [SMILES: *c1cc2c(n1C1CC1)C1CCN(CC1)C2]

In some embodiments, provided herein is a compound of Formula (I), or a pharmaceutically acceptable salt or solvate thereof, wherein $R_1$ is

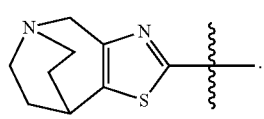 [SMILES: *c1nc2c(s1)C1CCN(CC1)C2]

In some embodiments, provided herein is a compound of Formula (I), or a pharmaceutically acceptable salt or solvate thereof, wherein $R_1$ is

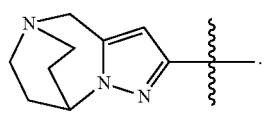 [SMILES: *c1cc2n(n1)C1CCN(CC1)C2]

In some embodiments, provided herein is a compound of Formula (I), or a pharmaceutically acceptable salt or solvate thereof, wherein $R_1$ is

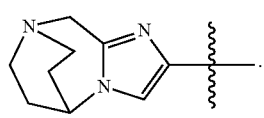 [SMILES: *c1cn2c(n1)CN1CCC2CC1]

In some embodiments, provided herein is a compound of Formula (I), or a pharmaceutically acceptable salt or solvate thereof, wherein $R_1$ is

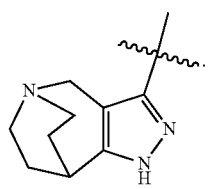 [SMILES: *c1n[nH]c2c1CN1CCC2CC1]

In some embodiments, provided herein is a compound of Formula (I), or a pharmaceutically acceptable salt or solvate thereof, wherein $R_1$ is

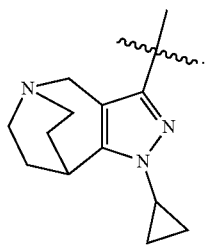 [SMILES: *c1nn(C2CC2)c2c1CN1CCC2CC1]

In some embodiments, provided herein is a compound of Formula (I), or a pharmaceutically acceptable salt or solvate thereof, wherein $R_2$ is

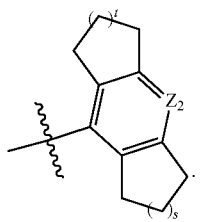

In some embodiments, provided herein is a compound of Formula (I), or a pharmaceutically acceptable salt or solvate thereof, wherein $R_2$ is

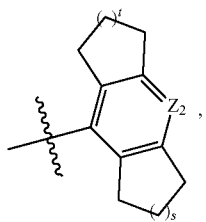

s is 1, and t is 1. In some embodiments, provided herein is a compound of Formula (I), or a pharmaceutically acceptable salt or solvate thereof, wherein $R_2$ is

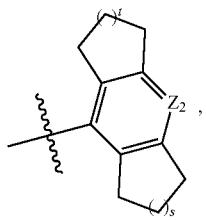

s is 1, t is 1, and $Z_2$ is $C(R_{19})$. In some embodiments, provided herein is a compound of Formula (I), or a pharmaceutically acceptable salt or solvate thereof, wherein $R_2$ is

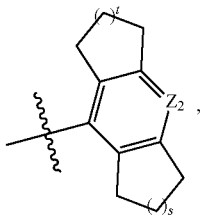

s is 1, t is 1, and $Z_2$ is C(H). In some embodiments, provided herein is a compound of Formula (I), or a pharmaceutically acceptable salt or solvate thereof, wherein $R_2$ is

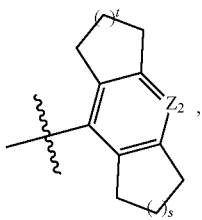

s is 1, t is 1, and $Z_2$ is N.

In some embodiments, provided herein is a compound of Formula (I), or a pharmaceutically acceptable salt or solvate thereof, wherein $R_2$ is

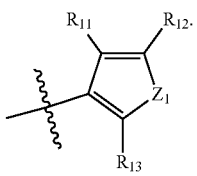

In some embodiments, provided herein is a compound of Formula (I), or a pharmaceutically acceptable salt or solvate thereof, wherein $R_2$ is

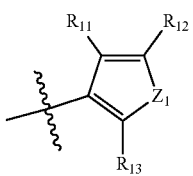

and $Z_1$ is S. In some embodiments, provided herein is a compound of Formula (I), or a pharmaceutically acceptable salt or solvate thereof, wherein $R_2$ is

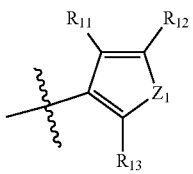

and $Z_1$ is —C($R_{17}$)=C($R_{17}$)—. In some embodiments, provided herein is a compound of Formula (I), or a pharmaceutically acceptable salt or solvate thereof, wherein $R_2$ is

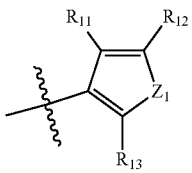

nd $Z_1$ is —C(H)=C(H)—. In some embodiments, provided herein is a compound of Formula (I), or a pharmaceutically acceptable salt or solvate thereof, wherein $R_2$ is

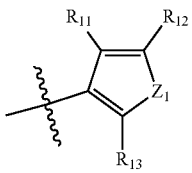

and $R_{11}$ and $R_{12}$ are combined to form a 5- or 6-membered cycloalkyl ring. In some embodiments, provided herein is a compound of Formula (I), or a pharmaceutically acceptable salt or solvate thereof, wherein $R_2$ is

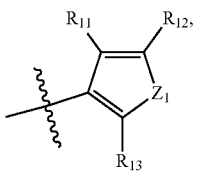

q is 1, and $R_{13}$ is $C_2$-$C_9$heteroaryl optionally substituted by 1, 2, or 3 $R_{16}$. In some embodiments, provided herein is a compound of Formula (I), or a pharmaceutically acceptable salt or solvate thereof, wherein $R_2$ is

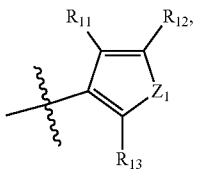

q is 1, and $R_{13}$ is pyridyl optionally substituted by 1 or 2 $R_{16}$. In some embodiments, provided herein is a compound of Formula (I), or a pharmaceutically acceptable salt or solvate thereof, wherein $R_2$ is

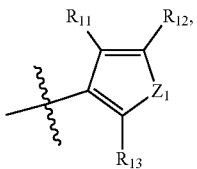

q is 1, $R_{13}$ is pyridyl optionally substituted by 1 or 2 $R_{16}$, and each $R_{16}$ is independently selected from halogen, $C_1$-$C_6$alkyl, $C_1$-$C_6$haloalkyl, and $C_1$-$C_6$alkoxy. In some embodiments, provided herein is a compound of Formula (I), or a pharmaceutically acceptable salt or solvate thereof, wherein $R_2$ is

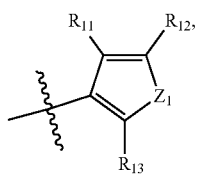

q is 1, $R_{13}$ is pyridyl optionally substituted by 1 $R_{16}$, and $R_{16}$ is selected from halogen, $C_1$-$C_6$alkyl, $C_1$-$C_6$haloalkyl, and $C_1$-$C_6$alkoxy. In some embodiments, provided herein is a compound of Formula (I), or a pharmaceutically acceptable salt or solvate thereof, wherein $R_2$ is

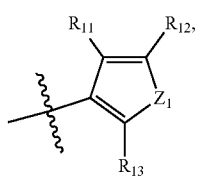

q is 1, $R_{13}$ is pyridyl optionally substituted by 1 $R_{16}$, and $R_{16}$ is $C_1$-$C_6$alkoxy.

In some embodiments, provided herein is a compound of Formula (I), or a pharmaceutically acceptable salt or solvate thereof, wherein $R_2$ is

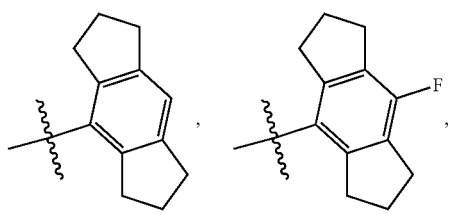

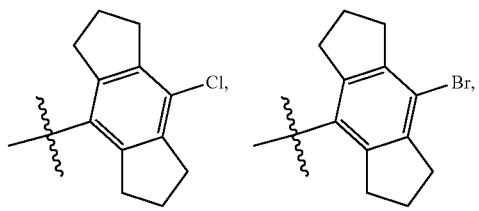

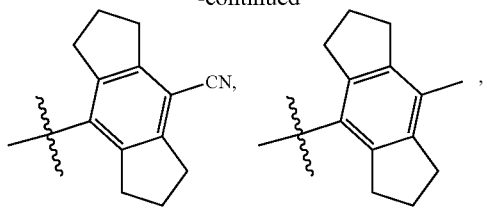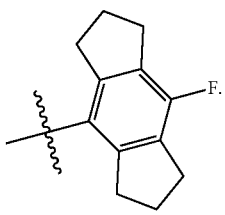 [SMILES: *c1c2c(c(F)c3c1CCC3)CCC2]

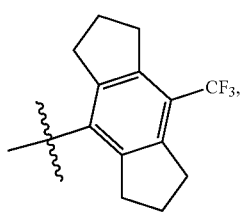

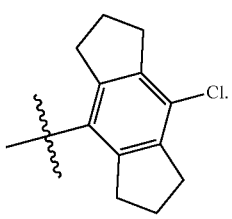

In some embodiments, provided herein is a compound of Formula (I), or a pharmaceutically acceptable salt or solvate thereof, wherein $R_2$ is

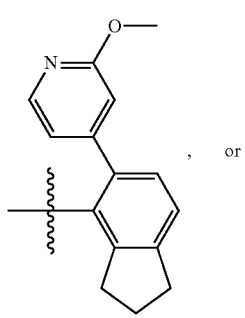

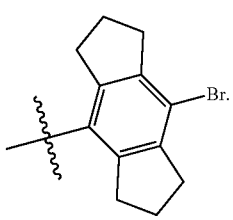 [SMILES: *c1c2c(c(Br)c3c1CCC3)CCC2]

In some embodiments, provided herein is a compound of Formula (I), or a pharmaceutically acceptable salt or solvate thereof, wherein $R_2$ is , or

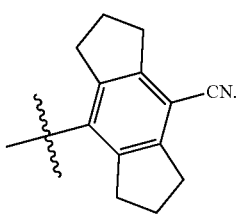 [SMILES: *c1c2c(c(C#N)c3c1CCC3)CCC2]

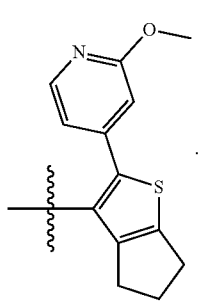

In some embodiments, provided herein is a compound of Formula (I), or a pharmaceutically acceptable salt or solvate thereof, wherein $R_2$ is

.

In some embodiments, provided herein is a compound of Formula (I), or a pharmaceutically acceptable salt or solvate thereof, wherein $R_2$ is

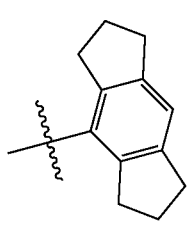

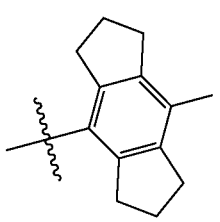

In some embodiments, provided herein is a compound of Formula (I), or a pharmaceutically acceptable salt or solvate thereof, wherein $R_2$ is In some embodiments, provided herein is a compound of Formula (I), or a pharmaceutically acceptable salt or solvate thereof, wherein R₂ is

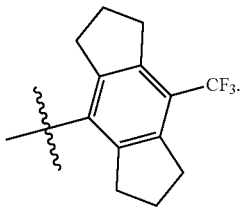 [SMILES: *c1c2c(c(C(F)(F)F)c3c1CCC3)CCC2]

In some embodiments, provided herein is a compound of Formula (I), or a pharmaceutically acceptable salt or solvate thereof, wherein R₂ is

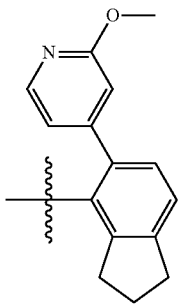

In some embodiments, provided herein is a compound of Formula (I), or a pharmaceutically acceptable salt or solvate thereof, wherein R₂ is

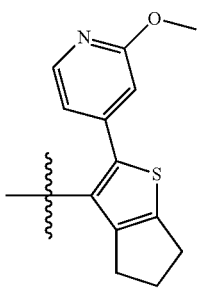

In some embodiments, provided herein is a compound of Formula (I), or a pharmaceutically acceptable salt or solvate thereof, wherein X₂ is —N(R₅)—. In some embodiments, provided herein is a compound of Formula (I), or a pharmaceutically acceptable salt or solvate thereof, wherein X₂ is —N(R₅)— and R₅ is hydrogen. In some embodiments, provided herein is a compound of Formula (I), or a pharmaceutically acceptable salt or solvate thereof, wherein X₂ is —N(R₅)— and R₅ is C₁-C₆alkyl. In some embodiments, provided herein is a compound of Formula (I), or a pharmaceutically acceptable salt or solvate thereof, wherein X₂ is —C(R₅)₂—. In some embodiments, provided herein is a compound of Formula (I), or a pharmaceutically acceptable salt or solvate thereof, wherein X₂ is —C(R₅)₂— and each R₅ is hydrogen.

In some embodiments, provided herein is a compound of Formula (I), or a pharmaceutically acceptable salt or solvate thereof, wherein X₃ is —N(R₅)—. In some embodiments, provided herein is a compound of Formula (I), or a pharmaceutically acceptable salt or solvate thereof, wherein X₃ is —N(R₅)— and R₅ is hydrogen. In some embodiments, provided herein is a compound of Formula (I), or a pharmaceutically acceptable salt or solvate thereof, wherein X₃ is —N(R₅)— and R₅ is C₁-C₆alkyl. In some embodiments, provided herein is a compound of Formula (I), or a pharmaceutically acceptable salt or solvate thereof, wherein X₃ is —C(R₅)₂—. In some embodiments, provided herein is a compound of Formula (I), or a pharmaceutically acceptable salt or solvate thereof, wherein X₃ is —C(R₅)₂— and each R₅ is hydrogen.

In some embodiments, provided herein is a compound of Formula (I), or a pharmaceutically acceptable salt or solvate thereof, wherein X₁ is O. In some embodiments, provided herein is a compound of Formula (I), or a pharmaceutically acceptable salt or solvate thereof, wherein X₁ is S. In some embodiments, provided herein is a compound of Formula (I), or a pharmaceutically acceptable salt or solvate thereof, wherein X₁ is N(R₃). In some embodiments, provided herein is a compound of Formula (I), or a pharmaceutically acceptable salt or solvate thereof, wherein X₁ is C(NO₂)(R₄).

In some embodiments, provided herein is a compound of Formula (Ia), or a pharmaceutically acceptable salt or solvate thereof:

Formula (Ia)

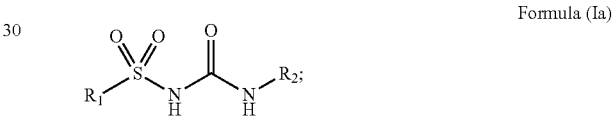

wherein:

Y₁ is O, S, or N(R₈);

Y₂ is N or C(R₉);

Z₁ is O, S, N(R₃), or —C(R₁₇)=C(R₁₇)—;

Z₂ is N or C(R₁₉);

R₁ is

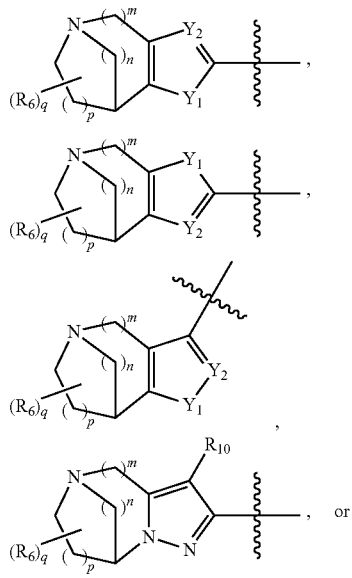

-continued

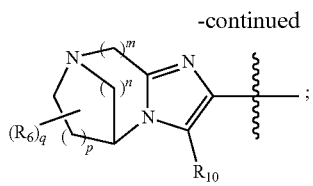

R₂ is

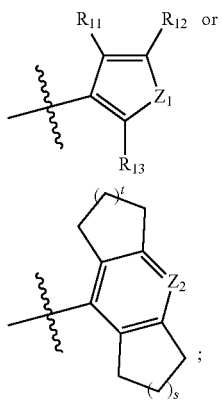

each R₆ is independently selected from C₁-C₆alkyl, —C₁-C₆alkyl-CO₂R₁₈, C₁-C₆haloalkyl, —C₁-C₆alkyl-OR₇, and —C₁-C₆alkyl-N(R₇)₂;
each R₇ is independently selected from hydrogen and C₁-C₆alkyl;
R₈ is hydrogen, C₁-C₆alkyl, —C₁-C₆alkyl-OR₇, —C₁-C₆alkyl-N(R₇)₂, or C₃-C₆cycloalkyl;
R₉ is hydrogen, halogen, C₁-C₆alkyl, C₁-C₆haloalkyl, or C₃-C₆cycloalkyl;
R₁₀ is hydrogen, halogen, C₁-C₆alkyl, C₁-C₆haloalkyl, —C₁-C₆alkyl-OR₇, or —C₁-C₆alkyl-N(R₇)₂;
R₁₁ and R₁₂ are independently selected from halogen, C₁-C₆alkyl, C₁-C₆haloalkyl, —C₁-C₆alkyl-OR₇, and —C₁-C₆alkyl-N(R₇)₂; or R₁₁ and R₁₂ are combined to form a 5- or 6-membered cycloalkyl ring;
R₁₃ is phenyl or C₂-C₉heteroaryl, wherein phenyl and C₂-C₉heteroaryl are optionally substituted by 1, 2, 3, or 4 R₁₆;
each R₁₆ is independently selected from halogen, C₁-C₆alkyl, C₁-C₆haloalkyl, C₁-C₆alkoxy, C₁-C₆haloalkoxy, C₃-C₆cycloalkyl, C₂-C₉heterocycloalkyl, C₆-C₁₀aryl, C₂-C₉heteroaryl, wherein C₃-C₆ cycloalkyl, C₂-C₉heterocycloalkyl, C₆-C₁₀aryl, C₂-C₉heteroaryl are optionally substituted with 1, 2, or 3 groups selected from halogen, C₁-C₆alkyl, C₁-C₆haloalkyl, C₁-C₆alkoxy, and C₁-C₆haloalkoxy;
each R₁₇ is independently selected from hydrogen, halogen, C₁-C₆alkyl, C₁-C₆haloalkyl, —C₁-C₆alkyl-OR₇, and —C₁-C₆alkyl-N(R₇)₂;
R₁₈ is hydrogen or C₁-C₆alkyl;
R₁₉ is hydrogen, halogen, —CN, C₁-C₆alkyl, C₁-C₆haloalkyl, —C₁-C₆alkyl-OR₇, or —C₁-C₆alkyl-N(R₇)₂;
m is 0, 1, or 2;
n is 1, 2, or 3;
p is 0, 1, or 2;
q is 0, 1, 2, 3, or 4;
s is 1, 2, or 3; and
t is 1, 2, or 3.

In some embodiments is a compound of Formula (Ia), or a pharmaceutically acceptable salt or solvate thereof, wherein R₁ is

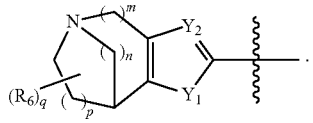

In some embodiments is a compound of Formula (Ia), or a pharmaceutically acceptable salt or solvate thereof, wherein R₁ is

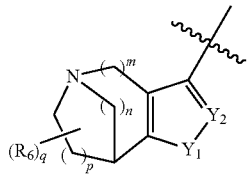

In some embodiments is a compound of Formula (Ia), or a pharmaceutically acceptable salt or solvate thereof, wherein R₁ is

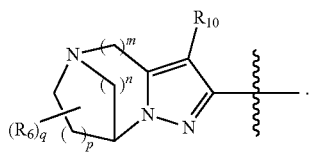

In some embodiments is a compound of Formula (Ia), or a pharmaceutically acceptable salt or solvate thereof, wherein R₁ is

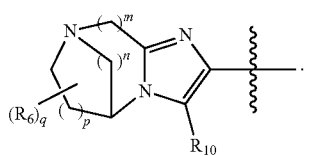

In some embodiments is a compound of Formula (Ia), or a pharmaceutically acceptable salt or solvate thereof, wherein R₁ is

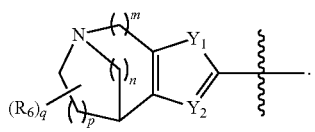

In some embodiments is a compound of Formula (Ia), or a pharmaceutically acceptable salt or solvate thereof, wherein m is 1. In some embodiments is a compound of Formula (Ia), or a pharmaceutically acceptable salt or solvate thereof, wherein m is 0. In some embodiments is a compound of Formula (Ia), or a pharmaceutically acceptable salt or solvate thereof, wherein m is 2.

In some embodiments is a compound of Formula (Ia), or a pharmaceutically acceptable salt or solvate thereof, wherein p is 1. In some embodiments is a compound of Formula (Ia), or a pharmaceutically acceptable salt or solvate thereof, wherein p is 0. In some embodiments is a compound of Formula (Ia), or a pharmaceutically acceptable salt or solvate thereof, wherein p is 2.

In some embodiments is a compound of Formula (Ia), or a pharmaceutically acceptable salt or solvate thereof, wherein m is 1 and p is 1.

In some embodiments is a compound of Formula (Ia), or a pharmaceutically acceptable salt or solvate thereof, wherein each $R_7$ is independently selected from $C_1$-$C_6$alkyl, —$C_1$-$C_6$alkyl-$CO_2R_{18}$, $C_1$-$C_6$haloalkyl, and $C_1$-$C_6$ heteroalkyl. In some embodiments is a compound of Formula (Ia), or a pharmaceutically acceptable salt or solvate thereof, wherein each $R_7$ is independently selected from $C_1$-$C_6$alkyl, —$C_1$-$C_6$alkyl-$CO_2R_{18}$, and $C_1$-$C_6$haloalkyl. In some embodiments is a compound of Formula (Ia), or a pharmaceutically acceptable salt or solvate thereof, wherein each $R_7$ is independently selected from $C_1$-$C_6$alkyl. In some embodiments is a compound of Formula (Ia), or a pharmaceutically acceptable salt or solvate thereof, wherein each $R_7$ is —$CH_3$.

In some embodiments, provided herein is a compound of Formula (Ia), or a pharmaceutically acceptable salt or solvate thereof, wherein q is 0, 1, 2, or 3. In some embodiments, provided herein is a compound of Formula (Ia), or a pharmaceutically acceptable salt or solvate thereof, wherein q is 0. In some embodiments, provided herein is a compound of Formula (Ia), or a pharmaceutically acceptable salt or solvate thereof, wherein q is 1. In some embodiments, provided herein is a compound of Formula (Ia), or a pharmaceutically acceptable salt or solvate thereof, wherein q is 2. In some embodiments, provided herein is a compound of Formula (Ia), or a pharmaceutically acceptable salt or solvate thereof, wherein q is 3. In some embodiments, provided herein is a compound of Formula (Ia), or a pharmaceutically acceptable salt or solvate thereof, wherein q is 4.

In some embodiments is a compound of Formula (Ia), or a pharmaceutically acceptable salt or solvate thereof, wherein $R_1$ is

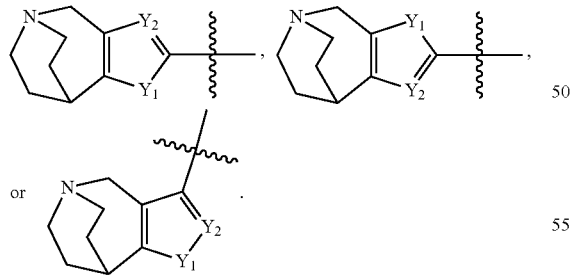

In some embodiments, provided herein is a compound of Formula (Ia), or a pharmaceutically acceptable salt or solvate thereof, wherein $Y_1$ is O. In some embodiments, provided herein is a compound of Formula (Ia), or a pharmaceutically acceptable salt or solvate thereof, wherein $Y_1$ is S. In some embodiments, provided herein is a compound of Formula (Ia), or a pharmaceutically acceptable salt or solvate thereof, wherein $Y_1$ is $N(R_8)$. In some embodiments, provided herein is a compound of Formula (Ia), or a pharmaceutically acceptable salt or solvate thereof, wherein $Y_1$ is $N(R_8)$ and $R_8$ is hydrogen or $C_1$-$C_6$alkyl.

In some embodiments, provided herein is a compound of Formula (Ia), or a pharmaceutically acceptable salt or solvate thereof, wherein $Y_2$ is N. In some embodiments, provided herein is a compound of Formula (Ia), or a pharmaceutically acceptable salt or solvate thereof, wherein $Y_2$ is $C(R_9)$. In some embodiments, provided herein is a compound of Formula (Ia), or a pharmaceutically acceptable salt or solvate thereof, wherein $Y_2$ is $C(R_9)$ and $R_9$ is selected from hydrogen and $C_1$-$C_6$alkyl. In some embodiments, provided herein is a compound of Formula (Ia), or a pharmaceutically acceptable salt or solvate thereof, wherein $Y_2$ is $C(R_9)$ and $R_9$ is hydrogen. In some embodiments, provided herein is a compound of Formula (Ia), or a pharmaceutically acceptable salt or solvate thereof, wherein $Y_2$ is $C(R_9)$ and $R_9$ is $C_1$-$C_6$alkyl.

In some embodiments, provided herein is a compound of Formula (Ia), or a pharmaceutically acceptable salt or solvate thereof, wherein $R_1$ is

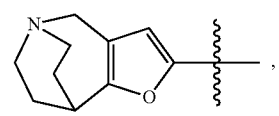

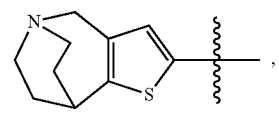

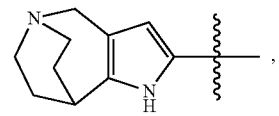

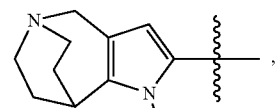

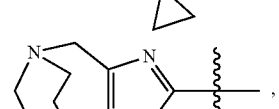

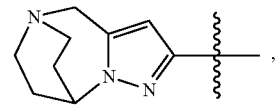

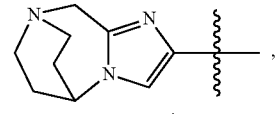

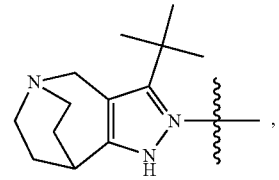, or

-continued

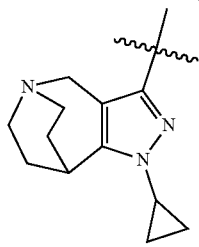

In some embodiments, provided herein is a compound of Formula (Ia), or a pharmaceutically acceptable salt or solvate thereof, wherein R₁ is

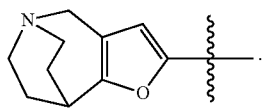

In some embodiments, provided herein is a compound of Formula (Ia), or a pharmaceutically acceptable salt or solvate thereof, wherein R₁ is

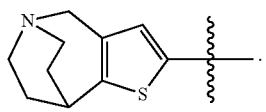 [SMILES: *c1cc2c(s1)C1CCN(CC1)C2]

In some embodiments, provided herein is a compound of Formula (Ia), or a pharmaceutically acceptable salt or solvate thereof, wherein R₁ is

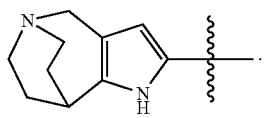 [SMILES: *c1cc2c([nH]1)C1CCN(CC1)C2]

In some embodiments, provided herein is a compound of Formula (Ia), or a pharmaceutically acceptable salt or solvate thereof, wherein R₁ is

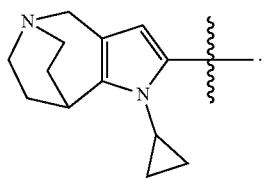 [SMILES: *c1cc2c(n1C1CC1)C1CCN(CC1)C2]

In some embodiments, provided herein is a compound of Formula (Ia), or a pharmaceutically acceptable salt or solvate thereof, wherein R₁ is

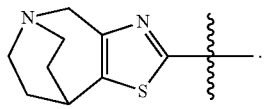 [SMILES: *c1nc2c(s1)C1CCN(CC1)C2]

In some embodiments, provided herein is a compound of Formula (Ia), or a pharmaceutically acceptable salt or solvate thereof, wherein R₁ is

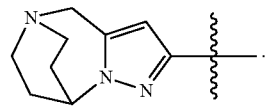 [SMILES: *c1cc2n(n1)C1CCN(CC1)C2]

In some embodiments, provided herein is a compound of Formula (Ia), or a pharmaceutically acceptable salt or solvate thereof, wherein R₁ is

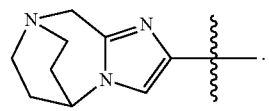 [SMILES: *c1cn2c(n1)CN1CCC2CC1]

In some embodiments, provided herein is a compound of Formula (Ia), or a pharmaceutically acceptable salt or solvate thereof, wherein R₁ is

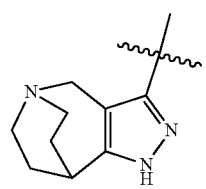

In some embodiments, provided herein is a compound of Formula (Ia), or a pharmaceutically acceptable salt or solvate thereof, wherein R₁ is.

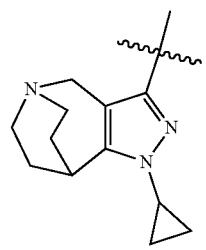

In some embodiments, provided herein is a compound of Formula (Ia), or a pharmaceutically acceptable salt or solvate thereof, wherein R₂ is

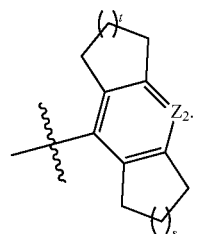

In some embodiments, provided herein is a compound of Formula (Ia), or a pharmaceutically acceptable salt or solvate thereof, wherein R₂ is

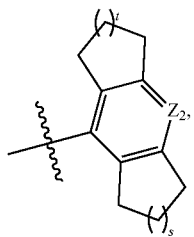

s is 1, and t is 1. In some embodiments, provided herein is a compound of Formula (Ia), or a pharmaceutically acceptable salt or solvate thereof, wherein $R_2$ is

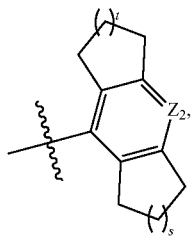

s is 1, t is 1, and $Z_2$ is $C(R_{19})$. In some embodiments, provided herein is a compound of Formula (Ia), or a pharmaceutically acceptable salt or solvate thereof, wherein $R_2$ is

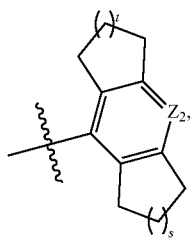

s is 1, t is 1, and $Z_2$ is C(H). In some embodiments, provided herein is a compound of Formula (Ia), or a pharmaceutically acceptable salt or solvate thereof, wherein $R_2$ is

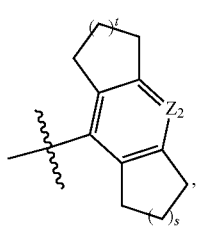

s is 1, t is 1, and $Z_2$ is N.

In some embodiments, provided herein is a compound of Formula (Ia), or a pharmaceutically acceptable salt or solvate thereof, wherein $R_2$ is

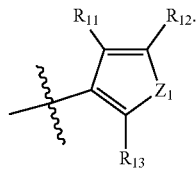

In some embodiments, provided herein is a compound of Formula (Ia), or a pharmaceutically acceptable salt or solvate thereof, wherein $R_2$ is

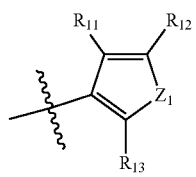

and $Z_1$ is S. In some embodiments, provided herein is a compound of Formula (Ia), or a pharmaceutically acceptable salt or solvate thereof, wherein $R_2$ is

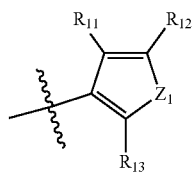

and $Z_1$ is —$C(R_{17})$=$C(R_{17})$—. In some embodiments, provided herein is a compound of Formula (Ia), or a pharmaceutically acceptable salt or solvate thereof, wherein $R_2$ is

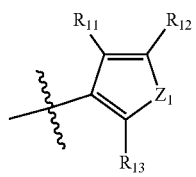

and $Z_1$ is —C(H)=C(H)—. In some embodiments, provided herein is a compound of Formula (Ia), or a pharmaceutically acceptable salt or solvate thereof, wherein $R_2$ is

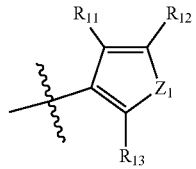

and $R_{11}$ and $R_{12}$ are combined to form a 5- or 6-membered cycloalkyl ring. In some embodiments, provided herein is a compound of Formula (Ia), or a pharmaceutically acceptable salt or solvate thereof, wherein $R_2$ is

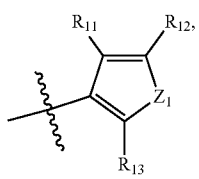

and R$_{13}$ is C$_2$-C$_9$heteroaryl optionally substituted by 1, 2, or 3 R$_{16}$. In some embodiments, provided herein is a compound of Formula (Ia), or a pharmaceutically acceptable salt or solvate thereof, wherein R$_2$ is

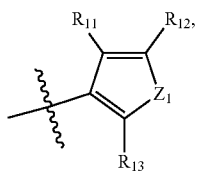

q is 1, and R$_{13}$ is pyridyl optionally substituted by 1 or 2 R$_{16}$. In some embodiments, provided herein is a compound of Formula (Ia), or a pharmaceutically acceptable salt or solvate thereof, wherein R$_2$ is

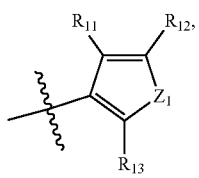

q is 1, R$_{13}$ is pyridyl optionally substituted by 1 or 2 R$_{16}$, and each R$_{16}$ is independently selected from halogen, C$_1$-C$_6$alkyl, C$_1$-C$_6$haloalkyl, and C$_1$-C$_6$alkoxy. In some embodiments, provided herein is a compound of Formula (Ia), or a pharmaceutically acceptable salt or solvate thereof, wherein R$_2$

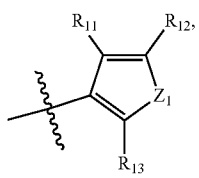

q is 1, R$_{13}$ is pyridyl optionally substituted by 1 R$_{16}$, and R$_{16}$ is selected from halogen, C$_1$-C$_6$alkyl, C$_1$-C$_6$haloalkyl, and C$_1$-C$_6$alkoxy. In some embodiments, provided herein is a compound of Formula (Ia), or a pharmaceutically acceptable salt or solvate thereof, wherein R$_2$ is

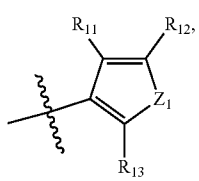

q is 1, R$_{13}$ is pyridyl optionally substituted by 1 R$_{16}$, and R$_{16}$ is C$_1$-C$_6$alkoxy.

In some embodiments, provided herein is a compound of Formula (Ia), or a pharmaceutically acceptable salt or solvate thereof, wherein R$_2$ is

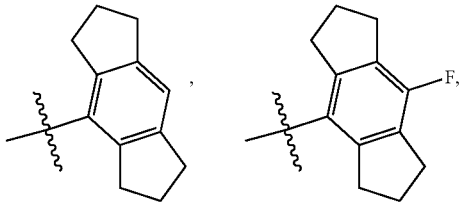

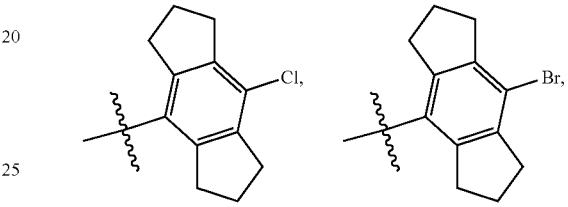

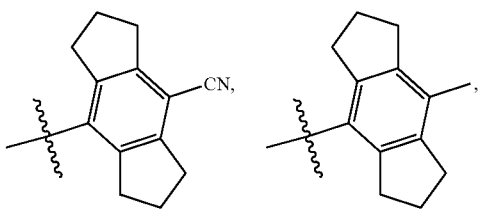

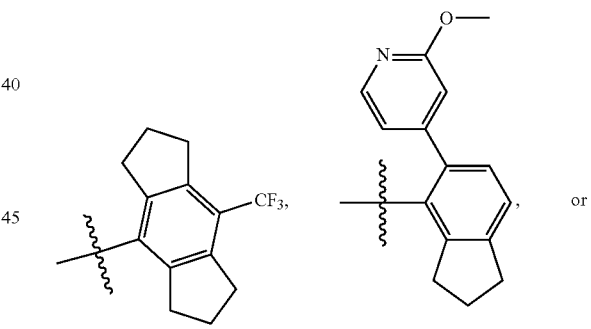

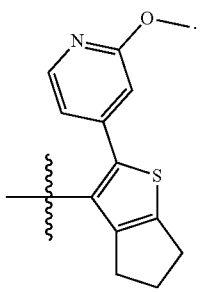

In some embodiments, provided herein is a compound of Formula (Ia), or a pharmaceutically acceptable salt or solvate thereof, wherein R$_2$ is

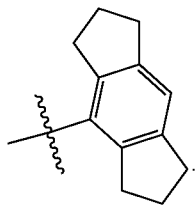 [SMILES: *c1c2c(cc3c1CCC3)CCC2]

In some embodiments, provided herein is a compound of Formula (Ia), or a pharmaceutically acceptable salt or solvate thereof, wherein $R_2$ is

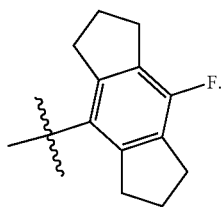 [SMILES: *c1c2c(c(F)c3c1CCC3)CCC2]

In some embodiments, provided herein is a compound of Formula (Ia), or a pharmaceutically acceptable salt or solvate thereof, wherein $R_2$ is

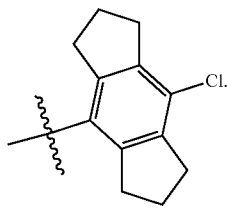 [SMILES: *c1c2c(c(Cl)c3c1CCC3)CCC2]

In some embodiments, provided herein is a compound of Formula (Ia), or a pharmaceutically acceptable salt or solvate thereof, wherein $R_2$ is

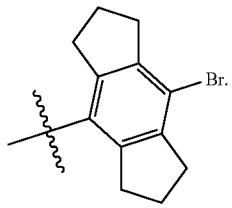 [SMILES: *c1c2c(c(Br)c3c1CCC3)CCC2]

In some embodiments, provided herein is a compound of Formula (Ia), or a pharmaceutically acceptable salt or solvate thereof, wherein $R_2$ is

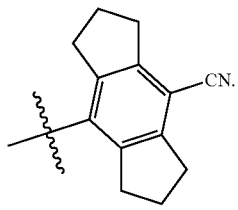 [SMILES: *c1c2c(c(C#N)c3c1CCC3)CCC2]

In some embodiments, provided herein is a compound of Formula (Ia), or a pharmaceutically acceptable salt or solvate thereof, wherein $R_2$ is

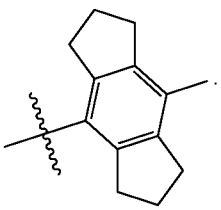 [SMILES: *c1c2c(c(C)c3c1CCC3)CCC2]

In some embodiments, provided herein is a compound of Formula (Ia), or a pharmaceutically acceptable salt or solvate thereof, wherein $R_2$ is

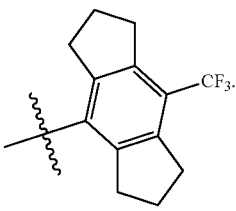 [SMILES: *c1c2c(c(C(F)(F)F)c3c1CCC3)CCC2]

In some embodiments, provided herein is a compound of Formula (Ia), or a pharmaceutically acceptable salt or solvate thereof, wherein $R_2$ is

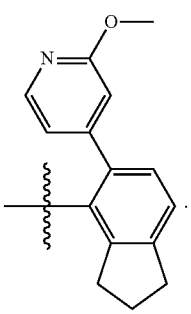 [SMILES: *c1c(-c2ccnc(OC)c2)ccc2c1CCC2]

In some embodiments, provided herein is a compound of Formula (Ia), or a pharmaceutically acceptable salt or solvate thereof, wherein $R_2$ is

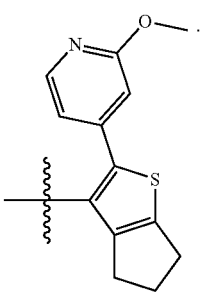 [SMILES: *c1c(-c2ccnc(OC)c2)sc2c1CCC2]

In some embodiments, provided herein is a compound selected from:

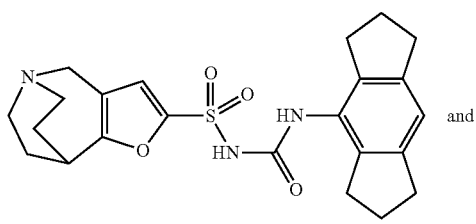 [SMILES: O=C(Nc1c2c(c(F)c3c1CCC3)CCC2)NS(=O)(=O)c1cc2c(o1)C1CCN(CC1)C2] and
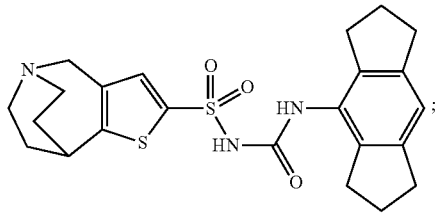
or a pharmaceutically acceptable salt or solvate thereof.
In some embodiments, provided herein is a compound selected from:
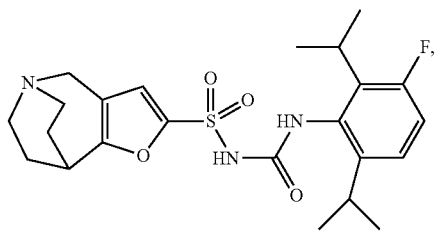
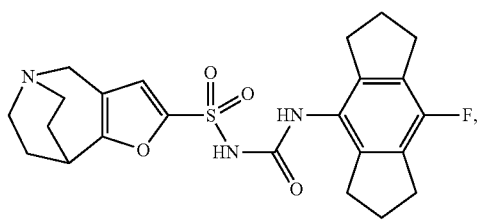
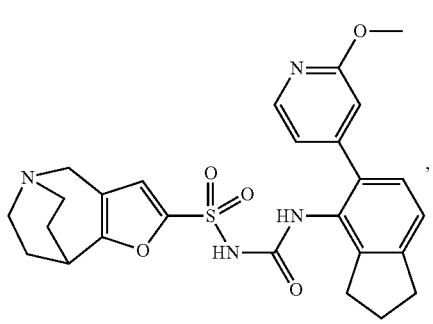
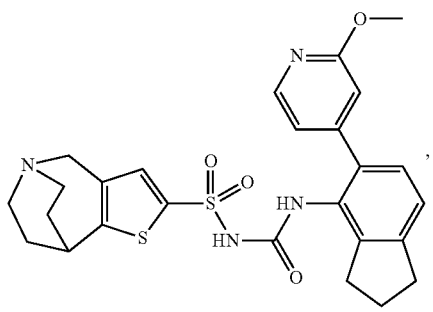
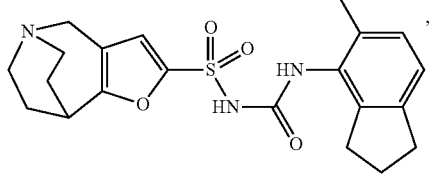
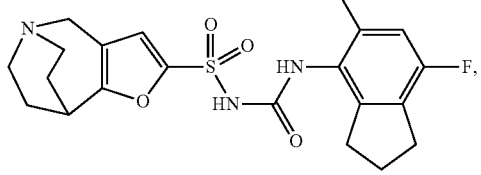
-continued
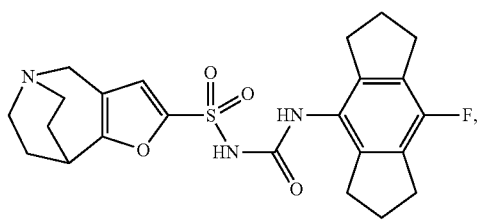
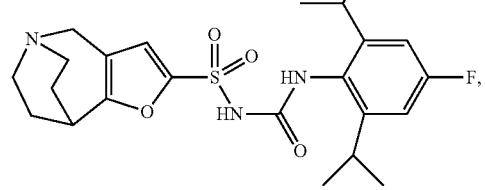
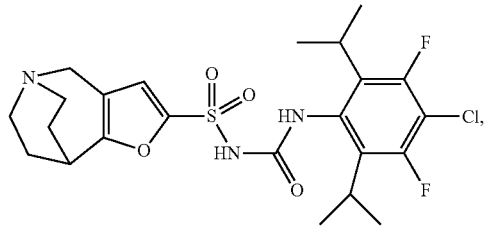
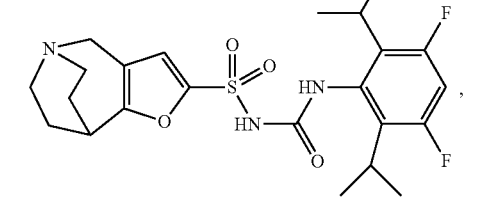
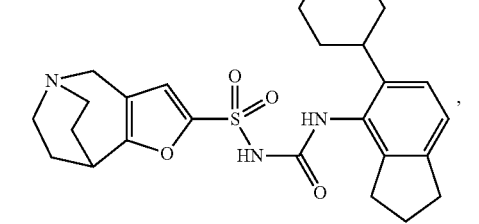

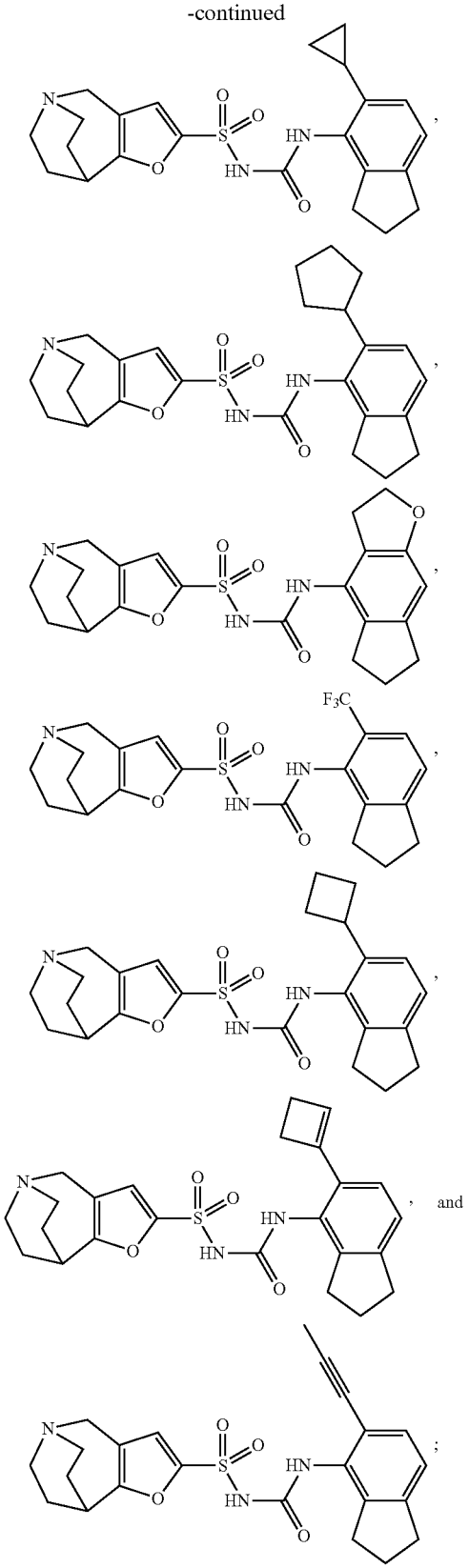
or a pharmaceutically acceptable salt or solvate thereof.
In some embodiments, provided herein is a compound selected from:
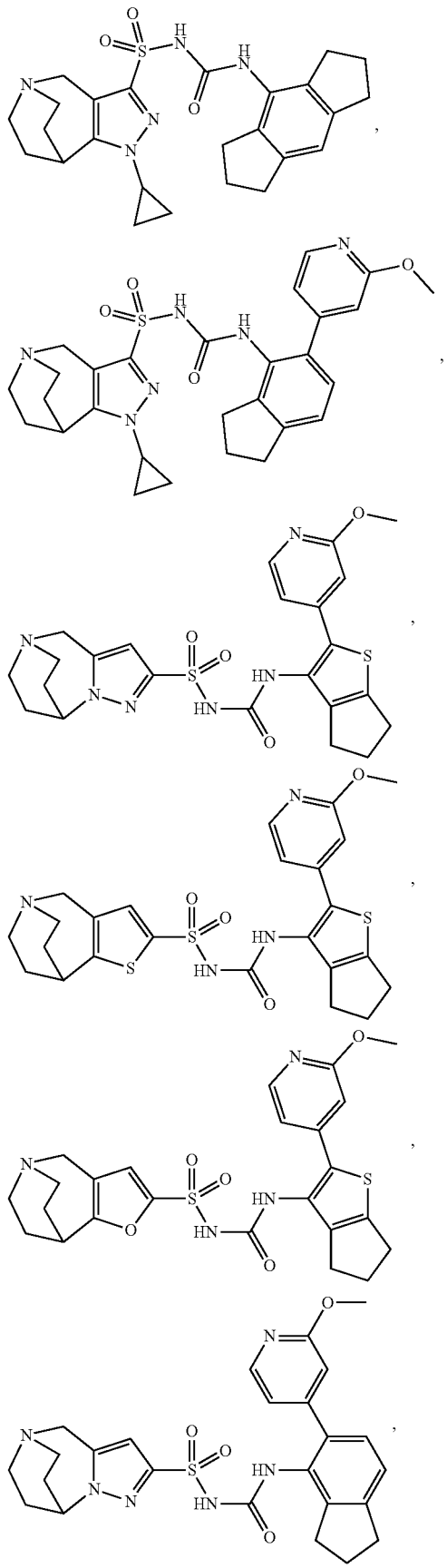

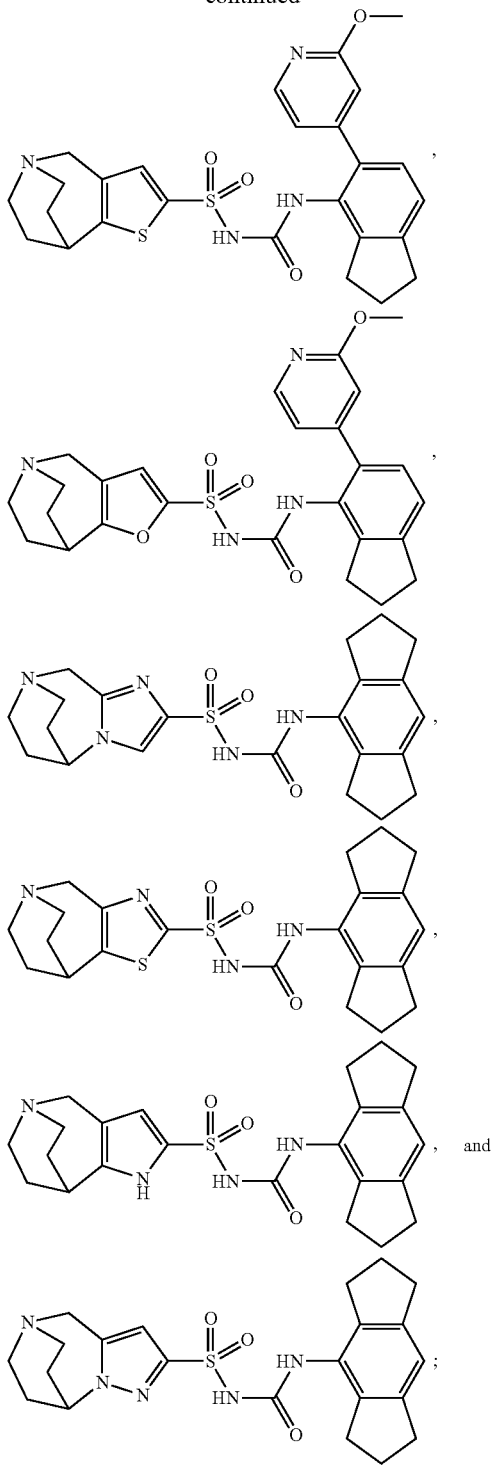

pharmaceutically acceptable salt or solvate thereof.

Any combination of the groups described above for the various variables is contemplated herein. Throughout the specification, groups and substituents thereof can be chosen by one skilled in the field to provide stable moieties and compounds.

In some embodiments, the therapeutic agent(s) (e.g. compound of Formula (I'), (I), or (Ia)) is present in the pharmaceutical composition as a pharmaceutically acceptable salt.

In some embodiments, any compound described above is suitable for any method or composition described herein.

Further Forms of Compounds Disclosed Herein

Isomers

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion, are useful for the applications described herein. In some embodiments, the compounds described herein are prepared as optically pure enantiomers by chiral chromatographic resolution of the racemic mixture. In some embodiments, the compounds described herein are prepared as their individual stereoisomers by reacting a racemic mixture of the compound with an optically active resolving agent to form a pair of diastereoisomeric compounds, separating the diastereomers, and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that does not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that are incorporated into compounds described herein include isotopes of hydrogen, carbon, nitrogen, oxygen, phosphorous, sulfur, fluorine, and chloride, such as $^{2}H$, $^{3}H$, $^{13}C$, $^{14}C$, $^{15}N$, $^{17}O$, $^{18}O$, $^{31}P$, $^{32}P$, $^{35}S$, $^{18}F$, and $^{36}Cl$, respectively. Compounds described herein, and pharmaceutically acceptable salts, esters, solvate, hydrates, or derivatives thereof which contain the aforementioned isotopes and/or other isotopes of other atoms are within the scope of this invention. Certain isotopically-labeled compounds, for example those into which radioactive isotopes such as $^{3}H$ and $^{14}C$ are incorporated, are useful in drug and/or substrate tissue distribution assays. Tritiated, i. e., $^{3}H$ and carbon-14, i.e., $^{14}C$, isotopes are particularly preferred for their ease of preparation and detectability. Further, substitution with heavy isotopes such as deuterium, i.e., $^{2}H$, produces certain therapeutic advantages resulting from greater metabolic stability, for example increased in vivo half-life or reduced dosage requirements. In some embodiments, the isotopically labeled compounds, pharmaceutically acceptable salt, ester, solvate, hydrate, or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds described herein, or by separately reacting a purified compound in its free form with a suitable acid or base, and isolating the salt thus formed.

Solvates

In some embodiments, the compounds described herein exist as solvates. In some embodiments are methods of treating diseases by administering such solvates. Further described herein are methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran, or MeOH. In addition, the compounds provided herein exist in unsolvated as well as solvated forms. In general, the solvated forms are considered equivalent to the unsolvated forms for the purposes of the compounds and methods provided herein.

Synthesis of Compounds

In some embodiments, the synthesis of compounds described herein are accomplished using means described in the chemical literature, using the methods described herein, or by a combination thereof. In addition, solvents, temperatures and other reaction conditions presented herein may vary.

In other embodiments, the starting materials and reagents used for the synthesis of the compounds described herein are synthesized or are obtained from commercial sources, such as, but not limited to, Sigma-Aldrich, FischerScientific (Fischer Chemicals), and AcrosOrganics.

In further embodiments, the compounds described herein, and other related compounds having different substituents are synthesized using techniques and materials described herein as well as those that are recognized in the field, such as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry $4^{th}$ Ed., (Wiley 1992); Carey and Sundberg, Advanced Organic Chemistry $4^{th}$ Ed., Vols. A and B (Plenum 2000, 2001), and Green and Wuts, Protective Groups in Organic Synthesis $3^{rd}$ Ed., (Wiley 1999) (all of which are incorporated by reference for such disclosure). General methods for the preparation of compound as disclosed herein may be derived from reactions and the reactions may be modified by the use of appropriate reagents and conditions, for the introduction of the various moieties found in the formulae as provided herein. As a guide the following synthetic methods may be utilized.

Use of Protecting Groups

In the reactions described, it may be necessary to protect reactive functional groups, for example hydroxy, amino, imino, thio or carboxy groups, where these are desired in the final product, in order to avoid their unwanted participation in reactions. Protecting groups are used to block some or all of the reactive moieties and prevent such groups from participating in chemical reactions until the protective group is removed. It is preferred that each protective group be removable by a different means. Protective groups that are cleaved under totally disparate reaction conditions fulfill the requirement of differential removal.

Protective groups can be removed by acid, base, reducing conditions (such as, for example, hydrogenolysis), and/or oxidative conditions. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, but not limited to, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be protected by conversion to simple ester compounds as exemplified herein, which include conversion to alkyl esters, or they may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a $Pd^{0}$-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typically blocking/protecting groups may be selected from:

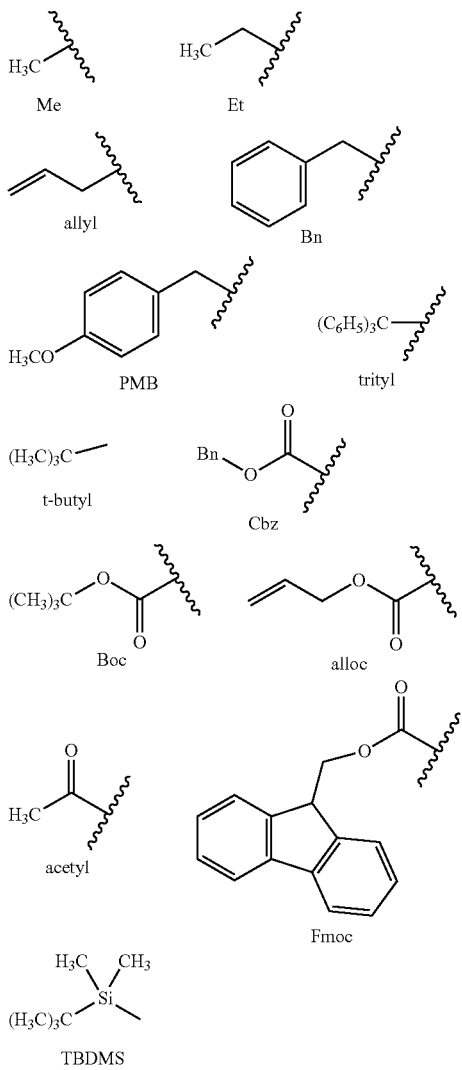

Other protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure).

Methods of Treatment and Prevention

In some embodiments is a method of treating a metabolic disease in a patient in need thereof, comprising administering to the patient a therapeutically effective amount of a compound Formula (I'), (I), or (Ia), or a pharmaceutically acceptable salt or solvate thereof. In some embodiments is a method of treating a metabolic disease in a patient in need thereof, comprising administering to the patient a therapeutically effective amount of a compound Formula (I'), (I), or (Ia), or a pharmaceutically acceptable salt or solvate thereof, wherein the metabolic disease is selected from type 2 diabetes, atherosclerosis, obesity and gout. In some embodiments is a method of treating type 2 diabetes in a patient in need thereof, comprising administering to the patient a therapeutically effective amount of a compound Formula (I'), (I), or (Ia), or a pharmaceutically acceptable salt or solvate thereof. In some embodiments is a method of treating atherosclerosis in a patient in need thereof, comprising administering to the patient a therapeutically effective amount of a compound Formula (I'), (I), or (Ia), or a pharmaceutically acceptable salt or solvate thereof. In some embodiments is a method of treating obesity in a patient in need thereof, comprising administering to the patient a therapeutically effective amount of a compound Formula (I'), (I), or (Ia), or a pharmaceutically acceptable salt or solvate thereof. In some embodiments is a method of treating gout in a patient in need thereof, comprising administering to the patient a therapeutically effective amount of a compound Formula (I'), (I), or (Ia), or a pharmaceutically acceptable salt or solvate thereof.

In some embodiments is a method of treating a liver disease in a patient in need thereof, comprising administering to the patient a therapeutically effective amount of a compound Formula (I'), (I), or (Ia), or a pharmaceutically acceptable salt or solvate thereof. In some embodiments is a method of treating a liver disease in a patient in need thereof, comprising administering to the patient a therapeutically effective amount of a compound Formula (I'), (I), or (Ia), or a pharmaceutically acceptable salt or solvate thereof, wherein the liver disease is selected from non-alcoholic fatty liver disease (NAFLD), non-alcoholic steatohepatitis (NASH), alcoholic steatohepatitis (ASH), viral hepatitis, or cirrhosis.

In some embodiments is a method of treating a lung disease in a patient in need thereof, comprising administering to the patient a therapeutically effective amount of a compound Formula (I'), (I), or (Ia), or a pharmaceutically acceptable salt or solvate thereof, wherein the lung disease is selected from asthma, COPD, and pulmonary idiopathic fibrosis.

In some embodiments is a method of treating a central nervous system disease in a patient in need thereof, comprising administering to the patient a therapeutically effective amount of a compound Formula (I'), (I), or (Ia), or a pharmaceutically acceptable salt or solvate thereof, wherein the central nervous system disease is selected Alzheimer's disease, multiple sclerosis, Amyotrophic Lateral Sclerosis, and Parkinson's disease.

In some embodiments is a method of treating an inflammatory or autoimmune disease in a patient in need thereof, comprising administering to the patient a therapeutically effective amount of a compound Formula (I'), (I), or (Ia), or a pharmaceutically acceptable salt or solvate thereof. In some embodiments is a method of treating an inflammatory or autoimmune disease in a patient in need thereof, comprising administering to the patient a therapeutically effective amount of a compound Formula (I'), (I), or (Ia), or a pharmaceutically acceptable salt or solvate thereof, wherein the disease is rheumatoid arthritis. In some embodiments is a method of treating an inflammatory or autoimmune disease in a patient in need thereof, comprising administering to the patient a therapeutically effective amount of a compound Formula (I'), (I), or (Ia), or a pharmaceutically acceptable salt or solvate thereof, wherein the disease is multiple sclerosis. In some embodiments is a method of treating an inflammatory or autoimmune disease in a patient in need thereof, comprising administering to the patient a therapeutically effective amount of a compound Formula (I'), (I), or (Ia), or a pharmaceutically acceptable salt or solvate thereof, wherein the disease is psoriasis. In some embodiments is a method of treating an inflammatory or autoimmune disease in a patient in need thereof, comprising administering to the patient a therapeutically effective amount of a compound Formula (I'), (I), or (Ia), or a pharmaceutically acceptable salt or solvate thereof, wherein the disease is lupus. In some embodiments is a method of treating an inflammatory or autoimmune disease in a patient in need thereof, comprising administering to the patient a therapeutically effective amount of a compound Formula (I'), (I), or (Ia), or a pharmaceutically acceptable salt or solvate thereof, wherein the disease is intestinal bowel disease. In some embodiments is a method of treating an inflammatory or autoimmune disease in a patient in need thereof, comprising administering to the patient a therapeutically effective amount of a compound Formula (I'), (I), or (Ia), or a pharmaceutically acceptable salt or solvate thereof, wherein the disease is Crohn's disease. In some embodiments is a method of treating an inflammatory or autoimmune disease in a patient in need thereof, comprising administering to the patient a therapeutically effective amount of a compound Formula (I'), (I), or (Ia), or a pharmaceutically acceptable salt or solvate thereof, wherein the disease is ulcerative colitis.

In some embodiments is a method of treating a cardiovascular disease in a patient in need thereof, comprising administering to the patient a therapeutically effective amount of a compound Formula (I'), (I), or (Ia), or a pharmaceutically acceptable salt or solvate thereof. In some embodiments is a method of treating a cardiovascular disease in a patient in need thereof, comprising administering to the patient a therapeutically effective amount of a compound Formula (I'), (I), or (Ia), or a pharmaceutically acceptable salt or solvate thereof, wherein the cardiovascular disease is atherosclerosis or stroke. In some embodiments is a method of treating atherosclerosis in a patient in need thereof, comprising administering to the patient a therapeutically effective amount of a compound Formula (I'), (I), or (Ia), or a pharmaceutically acceptable salt or solvate thereof. In some embodiments is a method of treating stroke in a patient in need thereof, comprising administering to the patient a therapeutically effective amount of a compound Formula (I'), (I), or (Ia), or a pharmaceutically acceptable salt or solvate thereof.

Pharmaceutical Compositions and Methods of Administration

NLRP3 inhibitors described herein are administered to subjects in a biologically compatible form suitable for administration to treat or prevent diseases, disorders or conditions. Administration of NLRP3 inhibitors as described herein can be in any pharmacological form including a therapeutically effective amount of a NLRP3 inhibitor alone or in combination with a pharmaceutically acceptable carrier.

In certain embodiments, the compounds described herein are administered as a pure chemical. In other embodiments, the compounds described herein are combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: The Science and Practice of Pharmacy (Gennaro, 21st Ed. Mack Pub. Co., Easton, Pa. (2005)).

Accordingly, provided herein is a pharmaceutical composition comprising at least one compound described herein, or a pharmaceutically acceptable salt, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

In some embodiments is a pharmaceutical composition comprising a pharmaceutically acceptable carrier and a compound of Formula (I'), (I), or (Ia), or a pharmaceutically acceptable salt or solvate thereof. In some embodiments is a pharmaceutical composition comprising a pharmaceutically acceptable carrier and a compound of Formula (I'), or a pharmaceutically acceptable salt or solvate thereof. In some embodiments is a pharmaceutical composition comprising a pharmaceutically acceptable carrier and a compound of Formula (I), or a pharmaceutically acceptable salt or solvate thereof. In some embodiments is a pharmaceutical composition comprising a pharmaceutically acceptable carrier and a compound of Formula (Ia), or a pharmaceutically acceptable salt or solvate thereof.

Another embodiment provides a pharmaceutical composition consisting essentially of a pharmaceutically acceptable carrier and a compound of Formula (I'), (I), or (Ia), or a pharmaceutically acceptable salt or solvate thereof. In some embodiments is a pharmaceutical composition consisting essentially of a pharmaceutically acceptable carrier and a compound of Formula (I'), or a pharmaceutically acceptable salt or solvate thereof. In some embodiments is a pharmaceutical composition consisting essentially of a pharmaceutically acceptable carrier and a compound of Formula (I), or a pharmaceutically acceptable salt or solvate thereof. In some embodiments is a pharmaceutical composition consisting essentially of a pharmaceutically acceptable carrier and a compound of Formula (Ia), or a pharmaceutically acceptable salt or solvate thereof.

In certain embodiments, the compound as described herein is substantially pure, in that it contains less than about 5%, or less than about 1%, or less than about 0.1%, of other organic small molecules, such as contaminating intermediates or by-products that are created, for example, in one or more of the steps of a synthesis method.

These formulations include those suitable for oral, topical, buccal, parenteral (e.g., subcutaneous, intramuscular, intradermal, or intravenous), or aerosol administration.

Exemplary pharmaceutical compositions are used in the form of a pharmaceutical preparation, for example, in solid, semisolid or liquid form, which includes one or more of a disclosed compound, as an active ingredient, in a mixture with an organic or inorganic carrier or excipient suitable for external, enteral or parenteral applications. In some embodiments, the active ingredient is compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

In some embodiments, NLRP3 inhibitors described herein are administered to subjects in a biologically compatible form suitable for topical administration to treat or prevent dermal diseases, disorders, or conditions. By "biologically compatible form suitable for topical administration" is meant a form of the NLRP3 inhibitor to be administered in which any toxic effects are outweighed by the therapeutic effects of the inhibitor. Administration of NLRP3 inhibitors as described herein can be in any pharmacological form including a therapeutically effective amount of a NLRP3 inhibitor alone or in combination with a pharmaceutically acceptable carrier.

Topical administration of a NLRP3 inhibitor may be presented in the form of an aerosol, a semi-solid pharmaceutical composition, a powder, or a solution. By the term "a semi-solid composition" is meant an ointment, cream, salve, jelly, or other pharmaceutical composition of substantially similar consistency suitable for application to the skin. Examples of semi-solid compositions are given in Chapter 17 of The Theory and Practice of Industrial Pharmacy, Lachman, Lieberman and Kanig, published by Lea and Febiger (1970) and in Chapter 67 of Remington's Pharmaceutical Sciences, 15th Edition (1975) published by Mack Publishing Company.

Dermal or skin patches are another method for transdermal delivery of the therapeutic or pharmaceutical compositions described herein. Patches can provide an absorption enhancer such as DMSO to increase the absorption of the compounds. Patches can include those that control the rate of drug delivery to the skin. Patches may provide a variety of dosing systems including a reservoir system or a monolithic system, respectively. The reservoir design may, for example, have four layers: the adhesive layer that directly contacts the skin, the control membrane, which controls the diffusion of drug molecules, the reservoir of drug molecules, and a water-resistant backing. Such a design delivers uniform amounts of the drug over a specified time period, the rate of delivery has to be less than the saturation limit of different types of skin. The monolithic design, for example, typically has only three layers: the adhesive layer, a polymer matrix containing the compound, and a water-proof backing. This design brings a saturating amount of drug to the skin. Thereby, delivery is controlled by the skin. As the drug amount decreases in the patch to below the saturating level, the delivery rate falls.

In one embodiment, the topical composition may, for example, take the form of hydrogel based on polyacrylic acid or polyacrylamide; as an ointment, for example with polyethyleneglycol (PEG) as the carrier, like the standard ointment DAB 8 (50% PEG 300, 50% PEG 1500); or as an emulsion, especially a microemulsion based on water-in-oil or oil-in-water, optionally with added liposomes. Suitable permeation accelerators (entraining agents) include sulphoxide derivatives such as dimethylsulphoxide (DMSO) or decylmethylsulphoxide (decyl-MSO) and transcutol (diethyleneglycolmonoethylether) or cyclodextrin; as well as pyrrolidones, for example 2-pyrrolidone, N-methyl-2-pyrrolidone, 2-pyrrolidone-5-carboxylic acid, or the biodegradable N-(2-hydroxyethyl)-2-pyrrolidone and the fatty acid esters thereof; urea derivatives such as dodecylurea, 1,3-didodecylurea, and 1,3-diphenylurea; and terpenes, for example D-limonene, menthone, a-terpinol, carvol, limonene oxide, or 1,8-cineol.

Ointments, pastes, creams and gels also can contain excipients, such as starch, tragacanth, cellulose derivatives, polyethylene glycols, silicones, bentonites, silicic acid, and talc, or mixtures thereof. Powders and sprays also can contain excipients such as lactose, talc, silicic acid, aluminum hydroxide, calcium silicates and polyamide powder, or mixtures of these substances. Solutions of nanocrystalline antimicrobial metals can be converted into aerosols or sprays by any of the known means routinely used for making aerosol pharmaceuticals. In general, such methods comprise pressurizing or providing a means for pressurizing a container of the solution, usually with an inert carrier gas, and passing the pressurized gas through a small orifice. Sprays can additionally contain customary propellants, such a chlorofluorohydrocarbons and volatile unsubstituted hydrocarbons, such as butane and propane.

The carrier can also contain other pharmaceutically-acceptable excipients for modifying or maintaining the pH, osmolarity, viscosity, clarity, color, sterility, stability, rate of dissolution, or odor of the formulation. The anti-skin aging compositions can also further comprise antioxidants, sunscreens, natural retinoids (e.g., retinol), and other additives commonly found in skin treatment compositions.

In some embodiments for preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a disclosed compound or a non-toxic pharmaceutically acceptable salt thereof. When referring to these preformulation compositions as homogeneous, it is meant that the active ingredient is dispersed evenly throughout the composition so that the composition is readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, cellulose, microcrystalline cellulose, silicified microcrystalline cellulose, lactose, sucrose, glucose, mannitol, and/or silicic acid; (2) binders, such as, for example, carboxymethylcellulose, hypromellose, alginates, gelatin, polyvinyl pyrrolidone, sucrose and/or acacia; (3) humectants, such as glycerol; (4) disintegrating agents, such as crospovidone, croscarmellose sodium, sodium starch glycolate, agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, docusate sodium, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, in some embodiments, the compositions comprise buffering agents. In some embodiments, solid compositions of a similar type are also employed as fillers in soft and hard-filled gelatin capsules using such excipients as lactose or milk sugars, as well as high molecular weight polyethylene glycols and the like.

In some embodiments, a tablet is made by compression or molding, optionally with one or more accessory ingredients. In some embodiments, compressed tablets are prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. In some embodiments, molded tablets are made by molding in a suitable machine a mixture of the subject composition moistened with an inert liquid diluent. In some embodiments, tablets, and other solid dosage forms, such as dragees, capsules, pills and granules, are scored or prepared with coatings and shells, such as enteric coatings and other coatings.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, in some embodiments, the liquid dosage forms contain inert diluents, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

In some embodiments, suspensions, in addition to the subject composition, contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

In some embodiments, powders and sprays contain, in addition to a subject composition, excipients such as lactose, talc, silicic acid, aluminum hydroxide, calcium silicates, and polyamide powder, or mixtures of these substances. In some embodiments, sprays additionally contain customary propellants, such as chlorofluorohydrocarbons and volatile unsubstituted hydrocarbons, such as butane and propane.

Compositions and compounds disclosed herein alternatively are administered by aerosol. This is accomplished by preparing an aqueous aerosol, liposomal preparation, or solid particles containing the compound. In some embodiments, a non-aqueous (e.g., fluorocarbon propellant) suspension is used. In some embodiments, sonic nebulizers are used because they minimize exposing the agent to shear, which results in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars, or sugar alcohols. Aerosols generally are prepared from isotonic solutions.

Pharmaceutical compositions suitable for parenteral administration comprise a subject composition in combination with one or more pharmaceutically-acceptable sterile isotonic aqueous or non-aqueous solutions, dispersions, suspensions or emulsions, or sterile powders which are reconstituted into sterile injectable solutions or dispersions just prior to use, which, in some embodiments, contain antioxidants, buffers, bacteriostats, solutes which render the formulation isotonic with the blood of the intended recipient, or suspending or thickening agents.

Examples of suitable aqueous and non-aqueous carriers which are employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity is maintained, for example, by the use of coating materials, such as lecithin, by the maintenance of the required particle size in the case of dispersions, and by the use of surfactants The dose of the composition comprising at least one compound described herein differs, depending upon the patient's (e.g., human) condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity). Optimal doses are generally determined using experimental models and/or clinical trials. In some embodiments, the optimal dose depends upon the body mass, weight, or blood volume of the patient.

Oral doses typically range from about 1.0 mg to about 1000 mg, one to four times, or more, per day.

Dose administration can be repeated depending upon the pharmacokinetic parameters of the dosage formulation and the route of administration used.

It is especially advantageous to formulate compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms are dictated by and directly dependent on (a) the unique characteristics of the NLRP3 inhibitor and the particular therapeutic effect to be achieved and (b) the limitations inherent in the art of compounding such an active compound for the treatment of sensitivity in individuals. The specific dose can be readily calculated by one of ordinary skill in the art, e.g., according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art in light of the NLRP3 inhibitor activities disclosed herein in assay preparations of target cells. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration.

Toxicity and therapeutic efficacy of such NLRP3 inhibitors can be determined by standard pharmaceutical procedures in cell cultures or experimental animals, for example, for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. NLRP3inhibitors that exhibit large therapeutic indices are preferred. While NLRP3inhibitors that exhibit toxic side effects may be used, care should be taken to design a delivery system that targets such inhibitors to the site of affected tissue in order to minimize potential damage to uninfected cells and, thereby, reduce side effects.

The data obtained from the cell culture assays and animal studies can be used in formulating a range of dosage for use in humans. The dosage of such NLRP3 inhibitors lies preferably within a range of circulating concentrations that include the $ED_{50}$ with little or no toxicity. The dosage may vary within this range depending upon the dosage form employed and the route of administration utilized. For any NLRP3 inhibitor used in a method described herein, the therapeutically effective dose can be estimated initially from cell culture assays. A dose may be formulated in animal models to achieve a circulating plasma concentration range that includes the $IC_{50}$ (i.e., the concentration of NLRP3 inhibitor that achieves a half-maximal inhibition of symptoms) as determined in cell culture. Such information can be used to more accurately determine useful doses in humans. Levels in plasma may be measured, for example, by high performance liquid chromatography.

EXAMPLES

The following examples are offered for purposes of illustration and are not intended to limit the scope of the claims provided herein. All literature citations in these examples and throughout this specification are incorporated herein by references for all legal purposes to be served thereby. The starting materials and reagents used for the synthesis of the compounds described herein may be synthesized or can be obtained from commercial sources, such as, but not limited to, Sigma-Aldrich, Acros Organics, Fluka, and Fischer Scientific.

Standard abbreviations and acronyms as defined in *J. Org. Chem.* 2007 72(1): 23A-24A are used herein. Other abbreviations and acronyms used herein are as follows:

| | |
|---|---|
| THF | tetrahydrofuran |
| ACN | acetonitrile |
| DMF | N, N-dimethylformamide |
| EtOH | ethanol |
| MeOH | methanol |
| DCM | dichloromethane |
| EtOAc | ethyl acetate |
| HATU | O-(7-Azabenzotriazol-1-yl)-N,N,N',N'-tetramethyluronium hexafluorophosphate |
| DIEA | N, N-diisopropylethylamine |
| $P_2O_5$ | phosphorus pentoxide |
| MsOH | methanesulfonic acid |
| NaH | sodium hydride |
| Mg | magnesium |
| $LiAlH_4$ | lithium aluminum hydride |
| $PPH_3$ | triphenylphosphine |
| DIAD | diisopropyl azodicarboxylate |
| $SO_3\cdot DMF$ | N,N-dimethylformamide sulfur trioxide Complex |
| SOCl2 | thionyl chloride |
| $NH_4OH$ | ammonium hydroxide |
| t-BuONa | sodium tert-butoxide |
| NaOH | sodium hydroxide |
| Mw | microwave |
| OVN | overnight |
| rt | room temperature |
| SM | starting material |

Example 1: Synthesis of Sodium ((1,2,3,5,6,7-hexa-hydro-s-indacen-4-yl)carbamoyl)((4,6,7,8-tetra-hydro-5,8-ethanofuro[3,2-c]azepin-2-yl)sulfonyl) amide (13)

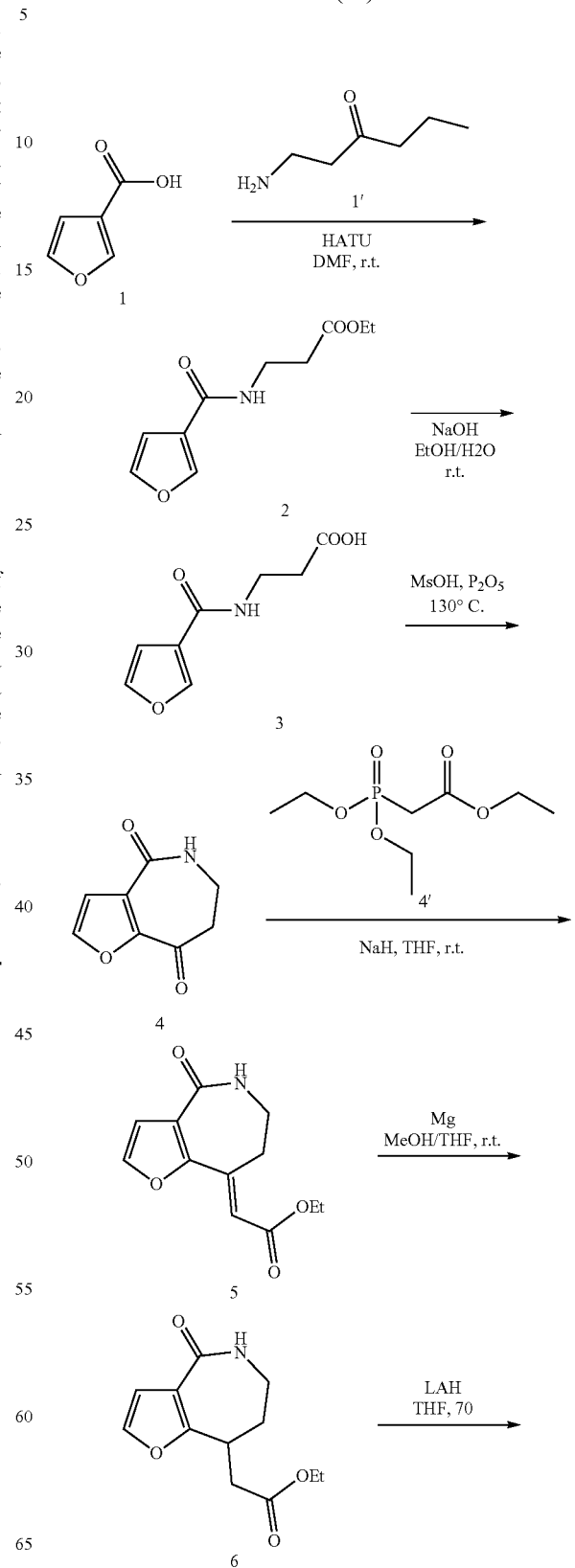

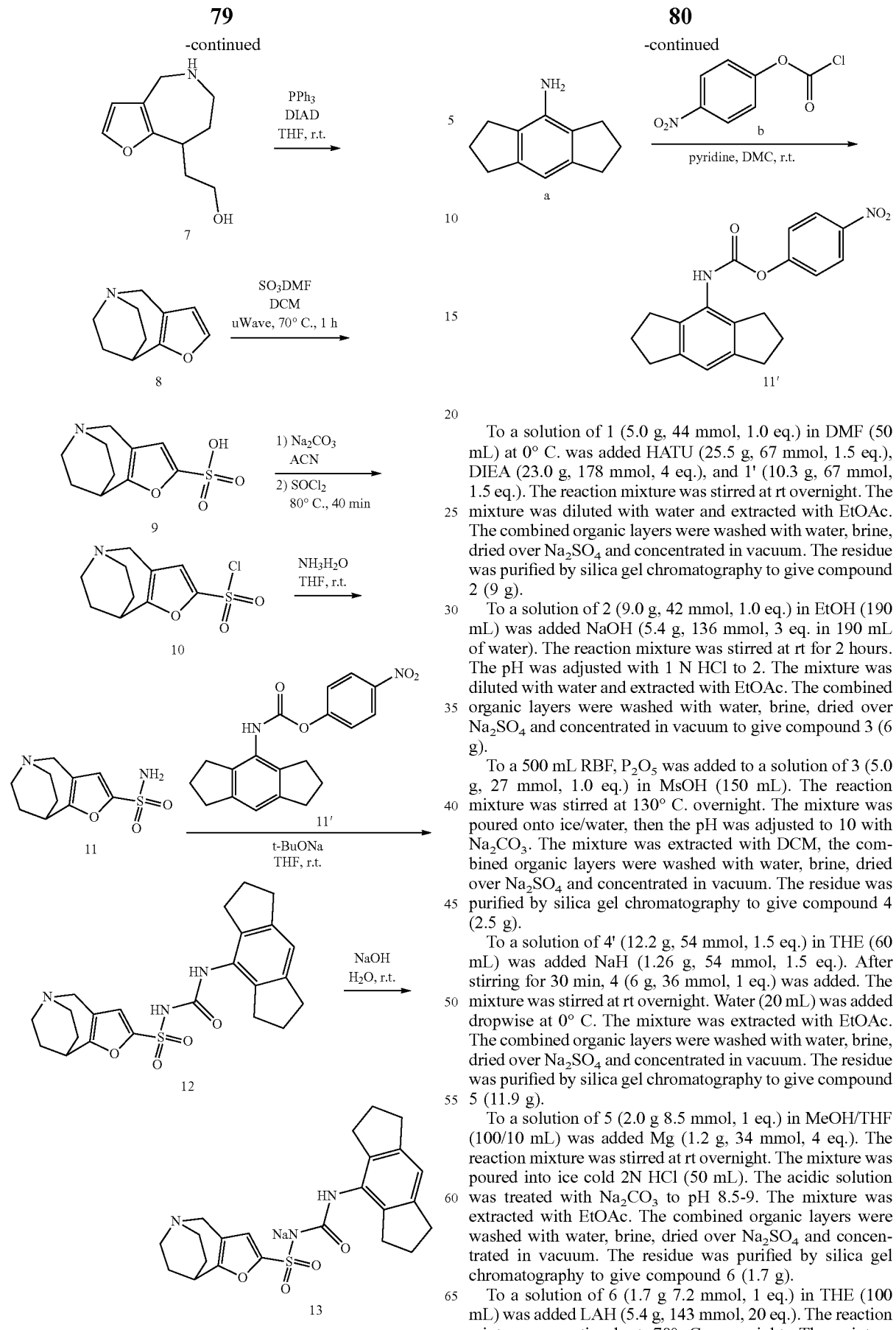

To a solution of 1 (5.0 g, 44 mmol, 1.0 eq.) in DMF (50 mL) at 0° C. was added HATU (25.5 g, 67 mmol, 1.5 eq.), DIEA (23.0 g, 178 mmol, 4 eq.), and 1' (10.3 g, 67 mmol, 1.5 eq.). The reaction mixture was stirred at rt overnight. The mixture was diluted with water and extracted with EtOAc. The combined organic layers were washed with water, brine, dried over $Na_2SO_4$ and concentrated in vacuum. The residue was purified by silica gel chromatography to give compound 2 (9 g).

To a solution of 2 (9.0 g, 42 mmol, 1.0 eq.) in EtOH (190 mL) was added NaOH (5.4 g, 136 mmol, 3 eq. in 190 mL of water). The reaction mixture was stirred at rt for 2 hours. The pH was adjusted with 1 N HCl to 2. The mixture was diluted with water and extracted with EtOAc. The combined organic layers were washed with water, brine, dried over $Na_2SO_4$ and concentrated in vacuum to give compound 3 (6 g).

To a 500 mL RBF, $P_2O_5$ was added to a solution of 3 (5.0 g, 27 mmol, 1.0 eq.) in MsOH (150 mL). The reaction mixture was stirred at 130° C. overnight. The mixture was poured onto ice/water, then the pH was adjusted to 10 with $Na_2CO_3$. The mixture was extracted with DCM, the combined organic layers were washed with water, brine, dried over $Na_2SO_4$ and concentrated in vacuum. The residue was purified by silica gel chromatography to give compound 4 (2.5 g).

To a solution of 4' (12.2 g, 54 mmol, 1.5 eq.) in THF (60 mL) was added NaH (1.26 g, 54 mmol, 1.5 eq.). After stirring for 30 min, 4 (6 g, 36 mmol, 1 eq.) was added. The mixture was stirred at rt overnight. Water (20 mL) was added dropwise at 0° C. The mixture was extracted with EtOAc. The combined organic layers were washed with water, brine, dried over $Na_2SO_4$ and concentrated in vacuum. The residue was purified by silica gel chromatography to give compound 5 (11.9 g).

To a solution of 5 (2.0 g 8.5 mmol, 1 eq.) in MeOH/THF (100/10 mL) was added Mg (1.2 g, 34 mmol, 4 eq.). The reaction mixture was stirred at rt overnight. The mixture was poured into ice cold 2N HCl (50 mL). The acidic solution was treated with $Na_2CO_3$ to pH 8.5-9. The mixture was extracted with EtOAc. The combined organic layers were washed with water, brine, dried over $Na_2SO_4$ and concentrated in vacuum. The residue was purified by silica gel chromatography to give compound 6 (1.7 g).

To a solution of 6 (1.7 g 7.2 mmol, 1 eq.) in THF (100 mL) was added LAH (5.4 g, 143 mmol, 20 eq.). The reaction mixture was stirred at 70° C. overnight. The mixture quenched with water and NaOH aq. The mixture was filtered and the solid was washed with MeOH. The solution was concentrated in vacuum and the residue was purified by silica gel chromatography to give compound 7 (700 mg).

To a solution of PPh₃ (2.2 g, 8.3 mmol, 3 eq.) and DIAD (1.7 g 8.3 mmol, 3 eq.) in THF (100 mL) at 0° C. was added 7 (500 mg, 2.7 mmol, 1 eq.). The reaction mixture was stirred at rt overnight. The solution was concentrated in vacuum and the residue was purified by silica gel chromatography to give compound 8 (330 mg).

To a solution of 8 (326 mg, 2.0 mmol, 1 eq.) in DCM (10 mL) was added SO₃DMF (918 mg, 6.0 mmol, 3 eq.) in a microwave tube. The mixture was heated in microwave at 70° C. for 1 hour. When the reaction completed, a dark solid was participated out. The solvent was decanted and the solid was dissolved in water (20 mL) and lyophilized to afford a crude mixture of compound 9 (400 mg) which was used directly without further purification.

To a solution of 9 (670 mg, 2.76 mmol, 1 eq.) in ACN (5 mL) was added Na₂CO₃ (584 mg, 5.51 mmol, 2 eq.). The mixture was stirred at rt for 30 min, then evaporated to dryness under reduced pressure. SOCl₂ (10 mL) was then added. The mixture was heated to 80° C. for 40 min, then evaporated to dryness to afford 10 which was used directly to the next step.

To a solution of 10 in THF (5 mL) was added NH₄OH (5 mL) slowly at 0° C. The reaction mixture was stirred at rt overnight. The reaction mixture was concentrated in vacuum. the residue was purified by silica gel chromatography to give 11 (270 mg).

To a solution of 11 (120 mg, 0.50 mmol, 1.0 eq.) in dry THF (15 mL) was added a solution of t-BuONa (240 mg, 2.5 mmol, 5.0 eq.) at 0° C. under N2. The mixture was stirred at rt for 15 mins. Then a solution of 11' (250 mg, 0.75 mmol, 1.5 eq.) was added to the reaction mixture at 0° C. and stirred at rt for 3 h. The reaction mixture was concentrated in vacuum. The residue was purified by silica gel chromatography to give 12 (200 mg). LCMS: [M+1]⁺=442.

To an aqueous NaOH solution (22.7 mL, 0.02 N NaOH) at 0° C. was added 12 (200 mg, 0.454 mmol, 1.0 eq.). The reaction was stirred at rt for 30 mins. The mixture was then lyophilized to afford the compound 13 as a light yellow solid. LCMS: [M-Na+1]⁺=442.15. ¹HNMR (400 MHz, CD₃OD) δ 6.85 (s, 1H), 6.67 (s, 1H), 3.87 (s, 2H), 3.22-3.10 (m, 2H), 3.04-2.95 (m, 3H), 2.81 (t, J=7.2 Hz, 4H), 2.06-1.91 (m, 8H).

To a solution of a (3.8 g, 21.97 mmol, 1.0 eq.) in dry DCM (50 mL) was added pyridine (10.97 mL, 136.24 mmol, 6.0 eq.) and b (3.99 g, 19.77 mmol, 0.9 eq.) slowly at 0° C. under N2. Then the reaction mixture was stirred at room temperature for 2 h. The mixture was diluted with DCM (300 mL) and washed with 0.6 M HCl (300 mL). The organic phases were washed with brine, dried over Na₂SO₄ and concentrated in vacuum to afford 11' (6.5 g) which was used without further purification.

Example 2: Synthesis of Sodium ((1,2,3,5,6,7-hexahydro-s-indacen-4-yl)carbamoyl)((4,6,7,8-tetrahydro-5,8-ethanothieno[3,2-c]azepin-2-yl)sulfonyl)amide (26)

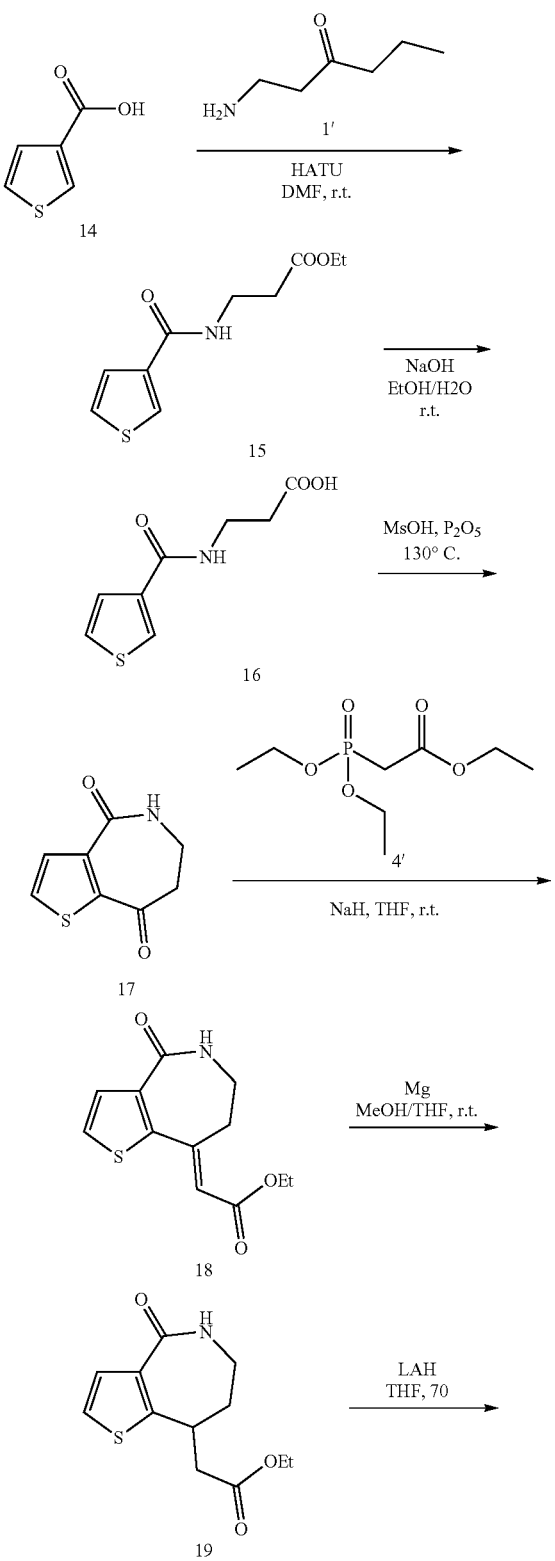

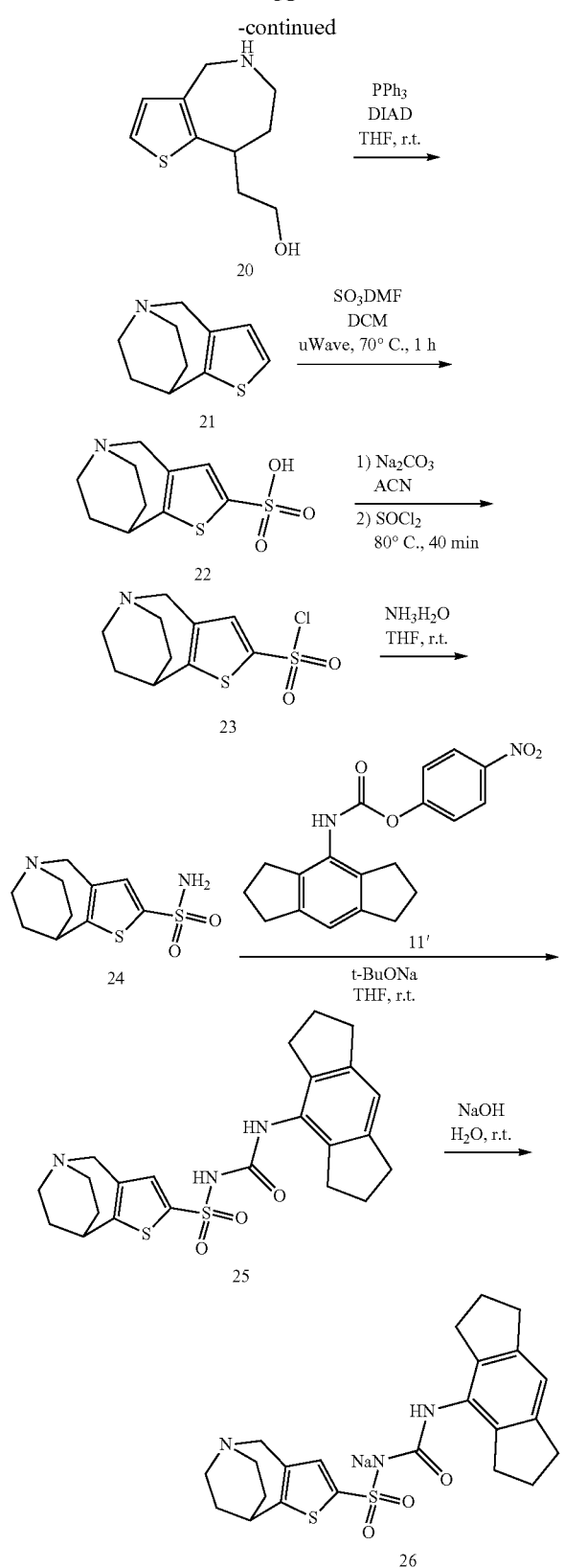

and the reaction mixture was stirred at rt overnight. The mixture was diluted with water (150 mL) and extracted with EtOAc (80 mL×3). The combined organic layer was washed with water (100 mL×3), brine (100 mL), dried over $Na_2SO_4$ and concentrated in vacuum. The residue was purified by silica gel chromatography to give 15 (3.06 g).

To a solution of 15 (3.06 g, 13.46 mmol, 1.0 eq.) in EtOH (30 mL) and $H_2O$ (10 mL) was added NaOH (1.62 g, 40.39 mmol, 3.0 eq.) slowly at 0° C. The reaction mixture was stirred at rt for 2 hours. The pH was adjusted to 2 with 3M HCl. The mixture extracted with EtOAc (50 mL×3). The combined organic layers were washed with water (80 mL×3), brine (50 mL), dried over $Na_2SO_4$ and concentrated in vacuum to give compound 16 (2.4 g) which was used to the next step without further purification.

To a solution of 16 (1.94 g, 9.7 mmol, 1.0 eq.) in MsOH (40 mL) was added a solution of $P_2O_5$ (6.9 g, 48.7 mmol, 5.0 eq.) at rt. The reaction mixture was stirred at 130° C. overnight. The reaction mixture was poured into ice water (200 mL) and extracted with DCM. The combined organic layer was concentrated in vacuum and purified by silica gel chromatography to afford compound 17 (1.24 g).

To a solution of 4' (1.56 g, 6.95 mmol, 1.2 eq.) at 0° C. was added NaH (1.26 g, 54 mmol, 1.5 eq.). After stirring at 0° C. for 30 min, 17 (1.05 g, 5.8 mmol, 1.0 eq.) was added. The mixture was stirred at rt overnight. Water (40 mL) was added dropwise at 0° C. The mixture was extracted with EtOAc (30 mL×3). The combined organic layers were washed with water (40 mL×3), brine (40 mL), dried over $Na_2SO_4$ and concentrated in vacuum to give compound 18 (1.2 g) which was used to the next step without further purification.

To a solution of 5 (1.2 g, 4.78 mmol, 1.0 eq.) in MeOH (40 mL) and THF (4 mL) was added Mg (470 mg, 19.10 mmol, 4.0 eq.). The reaction mixture was stirred at rt overnight. The mixture was adjusted pH to 1 with 3M HCl, and extracted with DCM (30 mL×3). The combined organic layer was washed with $NaHCO_3$ (45 mL), brine (45 mL), dried over $Na_2SO_4$ and concentrated in vacuum to give 19 (1.2 g).

To a solution of 19 (1.2 g, 50.14 mmol, 1.0 eq.) in THF (40 mL) was added LAH (3.8 g, 100.29 mmol, 20.0 eq.). The reaction mixture was stirred at 80° C. overnight. The mixture was cooled and quenched with ice-water (10 mL), NaOH (3N, 5 mL), and water (30 mL). The mixture was filtered and the filtrate was extracted with EtOAc (15 mL×3). The combined organic layer was washed with brine (20 mL), dried over $Na_2SO_4$ and concentrated in vacuum. The residue was purified by silica gel chromatography to give 20 (270 mg).

To a mixture of 7 (270 mg, 1.37 mmol, 1.0 eq.) and $PPh_3$ (1.26 g, 4.79 mmol, 3.5 eq.) in dry THF (50 mL) was added a DIAD (830 mg, 4.11 mmol, 3.0 eq.) slowly at 0° C. The reaction mixture was stirred at room temperature overnight. The mixture was concentrated in vacuum and the residue was purified by silica gel chromatography to give 21 (180 mg).

A mixture of 21 (156 mg, 0.87 mmol, 1.0 eq.) and $SO_3 \cdot DMF$ (400 mg, 2.61 mmol, 3.0 eq.) in DCM (5 mL) was stirred at 70° C. under microwave for 1 h. The mixture was concentrated in vacuum to give 22 (200 mg) which was used directly without further purification.

A solution of 22 (90 mg, 0.35 mmol, 1.0 eq.) in $SOCl_2$ (4 mL) was stirred at 80° C. for 1 h. The reaction mixture was concentrated in vacuum to give 23, which was used to the next step without further purification.

A mixture of 14 (2.0 g, 15.6 mmol, 1.0 eq.), DIEA (8.1 g, 62.4 mmol, 4.0 eq.) and HATU (9.0 g, 23.4 mmol, 1.5 eq.) in DMF (30 mL) was stirred at room temperature for 30 mins. Then 1' (3.6 g, 23.4 mmol, 1.5 eq.) was added at 0° C.

To a solution of 23 in THF (10 mL) was added NH₄OH (3 mL) slowly at 0° C. The reaction mixture was stirred at rt overnight. The reaction mixture was concentrated in vacuum. The residue was purified by silica gel chromatography to give 24 (45 mg).

To a solution of 11 (25 mg, 0.1 mmol, 1.0 eq.) in dry THF (3 mL) was added a solution of t-BuONa (47 mg, 0.48 mmol, 5.0 eq.) at 0° C. under N2. The mixture was stirred at rt for 15 mins. Then a solution of 11' (50 mg, 0.15 mmol, 1.5 eq.) was added to the reaction mixture at 0° C. and stirred at rt for 3 h. The reaction mixture was concentrated in vacuum. The residue was purified by silica gel chromatography to give 25 (36 mg). LCMS: [M+1]⁺=458.

To an aqueous NaOH solution (7.8 mL, 0.01 N NaOH) at 0° C. was added 25 (36 mg, 0.078 mmol, 1.0 eq.). The reaction was stirred at rt for 30 mins. The mixture was then lyophilized to afford the compound 26 (36 mg) as a light yellow solid. LCMS: 2.75 min, [M-Na+1]⁺=458.1. ¹HNMR (400 MHz, D₂O) δ 7.32 (s, 1H), 7.09 (s, 1H), 4.08 (s, 2H), 3.16~3.09 (m, 3H), 3.20~2.95 (m, 2H), 2.88 (t, J=7.2 Hz, 4H), 2.66 (t, J=7.2 Hz, 4H), 2.07-2.01 (m, 8H).

Compounds 27-44 were prepared by similar procedures as described in the preceding examples.

| Compound | Structure | Name | LCMS: [M + 1]⁺ |
|---|---|---|---|
| 27 | | N-((5-(2-methoxypyridin-4-yl)-2,3-dihydro-1H-inden-4-yl)carbamoyl)-4,6,7,8-tetrahydro-5,8-ethanofuro[3,2-c]azepine-2-sulfonamide | 509 |
| 28 | | N-((5-(2-methoxypyridin-4-yl)-2,3-dihydro-1H-inden-4-yl)carbamoyl)-4,6,7,8-tetrahydro-5,8-ethanothieno[3,2-c]azepine-2-sulfonamide | 525 |
| 29 | | N-((5-isopropyl-2,3-dihydro-1H-inden-4-yl)carbamoyl)-4,6,7,8-tetrahydro-5,8-ethanofuro[3,2-c]azepine-2-sulfonamide | 444 |
| 30 | | N-((7-fluoro-5-isopropyl-2,3-dihydro-1H-inden-4-yl)carbamoyl)-4,6,7,8-tetrahydro-5,8-ethanofuro[3,2-c]azepine-2-sulfonamide | 462 |

-continued

| Compound | Structure | Name | LCMS: [M + 1]+ |
|---|---|---|---|
| 31 | | N-((3-fluoro-2,6-diisopropylphenyl)carbamoyl)-4,6,7,8-tetrahydro-5,8-ethanofuro[3,2-c]azepine-2-sulfonamide | 464 |
| 32 | | N-((8-fluoro-1,2,3,5,6,7-hexahydro-s-indacen-4-yl)carbamoyl)-4,6,7,8-tetrahydro-5,8-ethanofuro[3,2-c]azepine-2-sulfonamide | 460 |
| 33 | | N-((8-cyano-1,2,3,5,6,7-hexahydro-s-indacen-4-yl)carbamoyl)-4,6,7,8-tetrahydro-5,8-ethanofuro[3,2-c]azepine-2-sulfonamide | 467 |
| 34 | | N-((4-fluoro-2,6-diisopropylphenyl)carbamoyl)-4,6,7,8-tetrahydro-5,8-ethanofuro[3,2-c]azepine-2-sulfonamide | 464 |
| 35 | | N-((4-chloro-3,5-difluoro-2,6-diisopropylphenyl)carbamoyl)-4,6,7,8-tetrahydro-5,8-ethanofuro[3,2-c]azepine-2-sulfonamide | 516 |
| 36 | | N-((3,5-difluoro-2,6-diisopropylphenyl)carbamoyl)-4,6,7,8-tetrahydro-5,8-ethanofuro[3,2-c]azepine-2-sulfonamide | 482 |

| Compound | Structure | Name | LCMS: [M + 1]+ |
|---|---|---|---|
| 37 | 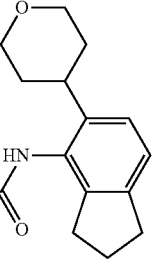 | N-((5-(tetrahydro-2H-pyran-4-yl)-2,3-dihydro-1H-inden-4-yl)carbamoyl)-4,6,7,8-tetrahydro-5,8-ethanofuro[3,2-c]azepine-2-sulfonamide | 486 |
| 38 | 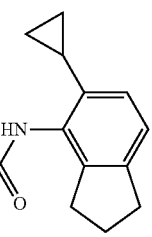 | N-((5-cyclopropyl-2,3-dihydro-1H-inden-4-yl)carbamoyl)-4,6,7,8-tetrahydro-5,8-ethanofuro[3,2-c]azepine-2-sulfonamide | 442 |
| 39 | 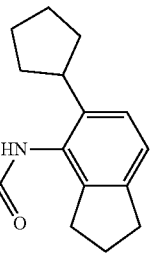 | N-((5-cyclopentyl-2,3-dihydro-1H-inden-4-yl)carbamoyl)-4,6,7,8-tetrahydro-5,8-ethanofuro[3,2-c]azepine-2-sulfonamide | 470 |
| 40 | 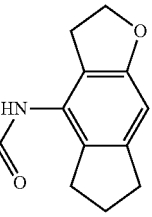 | N-((3,5,6,7-tetrahydro-2H-indeno[5,6-b]furan-4-yl)carbamoyl)-4,6,7,8-tetrahydro-5,8-ethanofuro[3,2-c]azepine-2-sulfonamide | 444 |
| 41 | 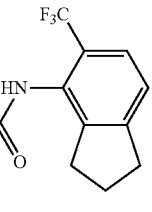 | N-((5-(trifluoromethyl)-2,3-dihydro-1H-inden-4-yl)carbamoyl)-4,6,7,8-tetrahydro-5,8-ethanofuro[3,2-c]azepine-2-sulfonamide | 470 |
| 42 | 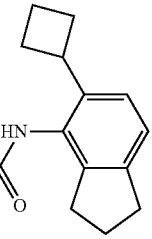 | N-((5-cyclobutyl-2,3-dihydro-1H-inden-4-yl)carbamoyl)-4,6,7,8-tetrahydro-5,8-ethanofuro[3,2-c]azepine-2-sulfonamide | 456 |

| Compound | Structure | Name | LCMS: [M + 1]+ |
|---|---|---|---|
| 43 | | N-((5-(cyclobut-1-en-1-yl)-2,3-dihydro-1H-inden-4-yl)carbamoyl)-4,6,7,8-tetrahydro-5,8-ethanofuro[3,2-c]azepine-2-sulfonamide | 454 |
| 44 | | N-((5-(prop-1-yn-1-yl)-2,3-dihydro-1H-inden-4-yl)carbamoyl)-4,6,7,8-tetrahydro-5,8-ethanofuro[3,2-c]azepine-2-sulfonamide | 440 |

Compounds 45-54 are prepared by similar procedures as described in the preceding examples.

| Compound | Structure | Name |
|---|---|---|
| 45 | | N-((1,2,3,5,6,7-hexahydro-s-indacen-4-yl)carbamoyl)-7,8-dihydro-4H,6H-5,8-ethanopyrazolo[1,5-a][1,4]diazepine-2-sulfonamide |
| 46 | | N-((1,2,3,5,6,7-hexahydro-s-indacen-4-yl)carbamoyl)-4,6,7,8-tetrahydro-1H-5,8-ethanopyrrolo[3,2-c]azepine-2-sulfonamide |
| 47 | | N-((1,2,3,5,6,7-hexahydro-s-indacen-4-yl)carbamoyl)-4,6,7,8-tetrahydro-5,8-ethanothiazolo[4,5-c]azepine-2-sulfonamide |
| 48 | | N-((1,2,3,5,6,7-hexahydro-s-indacen-4-yl)carbamoyl)-6,7-dihydro-5H,9H-5,8-ethanoimidazo[1,2-a][1,4]diazepine-2-sulfonamide |

-continued

| Compound | Structure | Name |
|---|---|---|
| 49 | 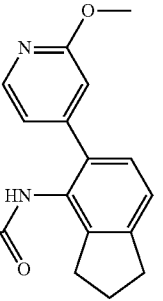 | N-((5-(2-methoxypyridin-4-yl)-2,3-dihydro-1H-inden-4-yl)carbamoyl)-7,8-dihydro-4H,6H-5,8-ethanopyrazolo[1,5-a][1,4]diazepine-2-sulfonamide |
| 50 | 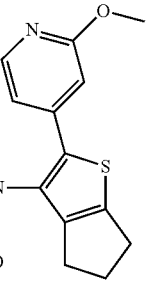 | N-((2-(2-methoxypyridin-4-yl)-5,6-dihydro-4H-cyclopenta[b]thiophen-3-yl)carbamoyl)-4,6,7,8-tetrahydro-5,8-ethanofuro[3,2-c]azepine-2-sulfonamide |
| 51 | 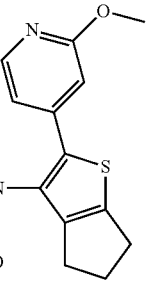 | N-((2-(2-methoxypyridin-4-yl)-5,6-dihydro-4H-cyclopenta[b]thiophen-3-yl)carbamoyl)-4,6,7,8-tetrahydro-5,8-ethanothieno[3,2-c]azepine-2-sulfonamide |
| 52 | 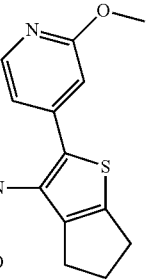 | N-((2-(2-methoxypyridin-4-yl)-5,6-dihydro-4H-cyclopenta[b]thiophen-3-yl)carbamoyl)-7,8-dihydro-4H,6H-5,8-ethanopyrazolo[1,5-a][1,4] diazepine-2-sulfonamide |
| 53 | 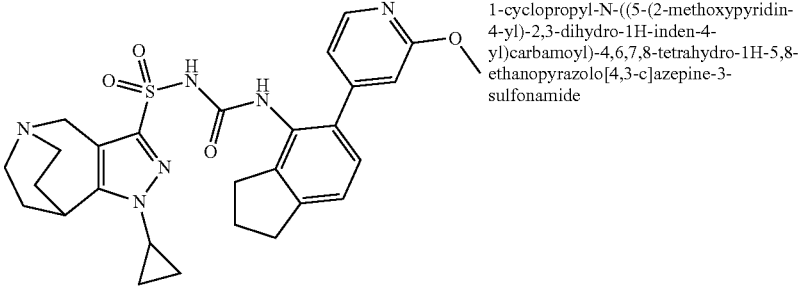 | 1-cyclopropyl-N-((5-(2-methoxypyridin-4-yl)-2,3-dihydro-1H-inden-4-yl)carbamoyl)-4,6,7,8-tetrahydro-1H-5,8-ethanopyrazolo[4,3-c]azepine-3-sulfonamide |

| Compound | Structure | Name |
|---|---|---|
| 54 | | 1-cyclopropyl-N-((1,2,3,5,6,7-hexahydro-s-indacen-4-yl)carbamoyl)-4,6,7,8-tetrahydro-1H-5,8-ethanopyrazolo[4,3-c]azepine-3-sulfonamide |

Example 3: Mouse BMDM IL-1b Assay

Mouse bone marrow cells from C57BL6 tibia and femur were culture in complete Isocov's Media supplemented with 20 ng/mL MCSF (BMDM media) at a density of 50 million cells/15 cm Petri dish. Fresh media was changed every 3 days, and bone marrow derived macrophages were collected, washed, and counted on day 7. Cells were seeded into 96 well plates at a density of $5 \times 10^4$ cells per well in 100 uL of BMDM media and cultured overnight. The cells were stimulated at 37° C. with 200 ng/mL Ultrapure LPS-B5 for 3 hours before pre-diluted compounds were added. 30 minutes after compound addition, 5 mM ATP was added for the secondary stimulation for 45 minutes. After stimulation, the plates were briefly spun down, and 50 uL of supernatant was harvested from each well. ELISA for mouse IL-1b was performed with 1:10 and 1:100 diluted supernatant using pre-coated kits. IL-1b concentrations were calculated based on pre-titrated standards, and compound inhibition IC50 is generated using the Levenberg Marquardt damped lease-square method.

$IC_{50}$ values are shown in the table below.

| Compound | IL-1b ($IC_{50}$) | Compound | IL-1b ($IC_{50}$) |
|---|---|---|---|
| 13 | A | 26 | A |

A: $IC_{50}$ < 100 nM

Example 4: Human Whole Blood (HWB) IL-1b Assay

Assay run as in Tran et al. "Whole blood assay as a model for in vitro evaluation of inflammasome activation and subsequent caspase-mediated interleukin-1 beta release" PLoSONE 14(4): e0214999.https://doi.org/10.1371/journal.pone.0214999. Namely, freshly drawn human whole blood with anti-coagulant was incubated with test compounds at various titration points for 0.5 hrs at 37° C. in 5% $CO_2$. The cells were subsequently primed with 100 ng/mL LPS for 3.5 hours at 37° C. followed by stimulation with 5 mM ATP for an additional 45 minutes. The supernatant was harvested and analyzed for human IL-1b concentration using commercially available ELISA kits.

$IC_{50}$ values are shown in the table below.

| Compound | HWB IL-1b ($IC_{50}$) |
|---|---|
| 12 | A |
| 13 | A |
| 25 | A |
| 26 | A |
| 27 | A |
| 28 | A |
| 29 | A |
| 30 | A |
| 31 | A |
| 32 | A |
| 33 | B |
| 34 | B |
| 35 | A |
| 36 | B |
| 37 | B |
| 38 | A |
| 39 | B |
| 40 | A |
| 41 | A |
| 42 | B |
| 43 | B |
| 44 | B |

A: $IC_{50}$ <1 µM; 1 µM ≤ B: $IC_{50}$ ≤ 10 µM.

Example 5: Human Monocyte IL-1b Assay

Human PBMC was harvested from fresh donor blood using Ficoll gradient. 50 million PBMC cells in 10 mL RPMI were plated onto 15 cm non-tissue culture treated petri dish and incubated at 37° C. for 1 h. At the end of the incubation, media was gently rocked and non-adherent cells were removed. The adherent cells were harvested with gentle scraping and counted. The enriched adherent cells were plated at $2 \times 10^4$ cells per well into 96 well plates and stimulated with 200 ng/mL Ultrapure LPS-B5 for 3 hours before pre-diluted compounds were added. 30 minutes after compound addition, 5 mM ATP was added for the secondary stimulation for 45 minutes. After stimulation, the plates were briefly spun down, and 50 uL of supernatant was harvested from each well. ELISA for human IL-1b was performed with 1:10 and 1:100 diluted supernatant using pre-coated kits. IL-1b concentrations were calculated based on pre-titrated standards, and compound inhibition IC50 is generated using the Levenberg Marquardt damped lease-square method.

The examples and embodiments described herein are for illustrative purposes only and in some embodiments, various modifications or changes are to be included within the purview of disclosure and scope of the appended claims.

What is claimed is:

1. A compound of Formula (I'), or a pharmaceutically acceptable salt or solvate thereof:

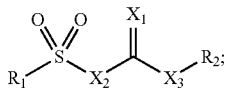

Formula (I')

wherein:

$X_1$ is O, S, or $N(R_3)$;
$X_2$ is —$N(R_4)$— or —$C(R_4)_2$—;
$X_3$ is —$N(R_5)$— or —$C(R_5)_2$—;
$Y_1$ is O, S, or $N(R_8)$;
$Y_2$ is N or $C(R_9)$;
$Z_1$ is O, S, $N(R_3)$, or —$C(R_{17})$=$C(R_{17})$—;
$Z_2$ is N or $C(R_{19})$;
$R_1$ is

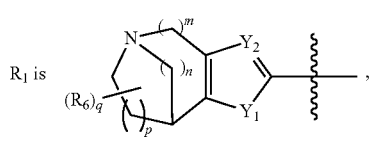,

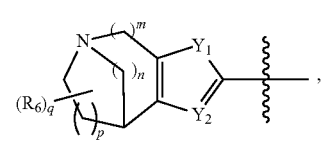,

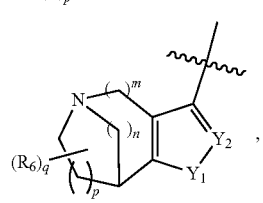,

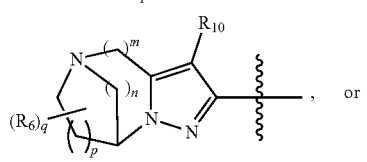, or

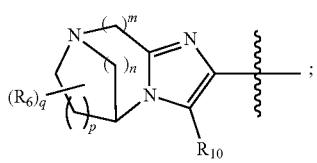;

$R_2$ is 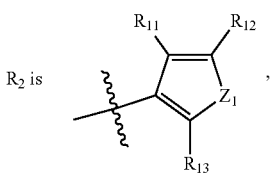, 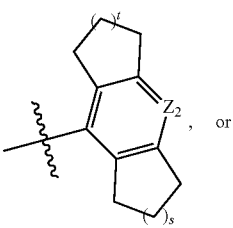, or

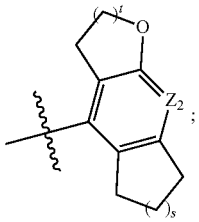;

$R_3$ is hydrogen, —$OR_{14}$, —CN, —$NO_2$, or —$S(=O)_2R_{15}$;
each $R_4$ is independently selected from hydrogen, $C_1$-$C_6$alkyl, —$C_1$-$C_6$alkyl-$OR_7$, and —$C_1$-$C_6$alkyl-N$(R_7)_2$;
each $R_5$ is independently selected from hydrogen, $C_1$-$C_6$alkyl, —$C_1$-$C_6$alkyl-$OR_7$, and —$C_1$-$C_6$alkyl-N$(R_7)_2$;
each $R_6$ is independently selected from $C_1$-$C_6$alkyl, —$C_1$-$C_6$alkyl-$CO_2R_{18}$, $C_1$-$C_6$haloalkyl, —$C_1$-$C_6$alkyl-$OR_7$, and —$C_1$-$C_6$alkyl-N$(R_7)_2$;
each $R_7$ is independently selected from hydrogen and $C_1$-$C_6$alkyl;
$R_8$ is hydrogen, $C_1$-$C_6$alkyl, —$C_1$-$C_6$alkyl-$OR_7$, —$C_1$-$C_6$alkyl-N$(R_7)_2$, or $C_3$-$C_6$cycloalkyl;
$R_9$ is hydrogen, halogen, $C_1$-$C_6$alkyl, $C_1$-$C_6$haloalkyl, or $C_3$-$C_6$cycloalkyl;
$R_{10}$ is hydrogen, halogen, $C_1$-$C_6$alkyl, $C_1$-$C_6$haloalkyl, —$C_1$-$C_6$alkyl-$OR_7$, or —$C_1$-$C_6$alkyl-N$(R_7)_2$;
$R_{11}$ and $R_{12}$ are independently selected from hydrogen, halogen, $C_1$-$C_6$alkyl, $C_1$-$C_6$haloalkyl, —$C_1$-$C_6$alkyl-$OR_7$, and —$C_1$-$C_6$alkyl-N$(R_7)_2$; or RH and $R_{12}$ are combined to form a 5- or 6-membered cycloalkyl ring;
$R_{13}$ is hydrogen, $C_1$-$C_6$alkyl, $C_1$-$C_6$haloalkyl, $C_2$-$C_6$alkenyl, $C_2$-$C_6$alkynyl, $C_3$-$C_5$cycloalkyl, $C_2$-$C_9$heterocycloalkyl, phenyl, or $C_2$-$C_9$heteroaryl, wherein $C_3$-$C_5$cycloalkyl, $C_2$-$C_9$heterocycloalkyl, phenyl, and $C_2$-$C_9$heteroaryl are optionally substituted by 1, 2, 3, or 4 $R_{16}$;
$R_{14}$ is hydrogen or $C_1$-$C_6$alkyl;
$R_{15}$ is $C_1$-$C_6$alkyl;
each $R_{16}$ is independently selected from halogen, $C_1$-$C_6$alkyl, $C_1$-$C_6$haloalkyl, $C_1$-$C_6$alkoxy, $C_1$-$C_6$haloalkoxy, $C_3$-$C_6$cycloalkyl, $C_2$-$C_9$heterocycloalkyl, $C_6$-$C_{10}$aryl, and $C_2$-$C_9$heteroaryl, wherein $C_3$-$C_6$cycloalkyl, $C_2$-$C_9$heterocycloalkyl, $C_6$-$C_{10}$aryl, and $C_2$-$C_9$heteroaryl are optionally substituted with 1, 2, or 3 groups selected from halogen, $C_1$-$C_6$alkyl, $C_1$-$C_6$haloalkyl, $C_1$-$C_6$alkoxy, and $C_1$-$C_6$haloalkoxy;
each $R_{17}$ is independently selected from hydrogen, halogen, $C_1$-$C_6$alkyl, $C_1$-$C_6$haloalkyl, —$C_1$-$C_6$alkyl-$OR_7$, and —$C_1$-$C_6$alkyl-N$(R_7)_2$;
$R_{18}$ is hydrogen or $C_1$-$C_6$alkyl;
$R_{19}$ is hydrogen, halogen, —CN, $C_1$-$C_6$alkyl, $C_1$-$C_6$haloalkyl, —$C_1$-$C_6$alkyl-$OR_7$, or —$C_1$-$C_6$alkyl-N$(R_7)_2$;
m is 0, 1, or 2;
n is 1, 2, or 3;
p is 0, 1, or 2;
q is 0, 1, 2, 3, or 4;
s is 1, 2, or 3; and
t is 1, 2, or 3.

2. The compound of claim 1, or a pharmaceutically acceptable salt or solvate thereof, wherein $R_1$ is

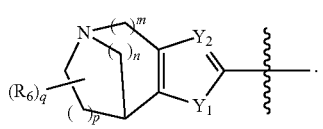

3. The compound of claim 2, or a pharmaceutically acceptable salt or solvate thereof, wherein $Y_2$ is $C(R_9)$, $R_9$ is hydrogen, and $Y_1$ is O.

4. The compound of claim 3, or a pharmaceutically acceptable salt or solvate thereof, wherein q is 0, n is 2, m is 1, and p is 1.

5. The compound of claim 1, or a pharmaceutically acceptable salt or solvate thereof, wherein $R_1$ is

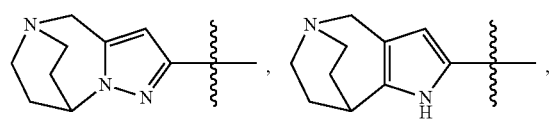

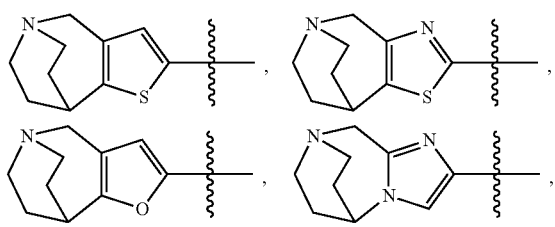

or

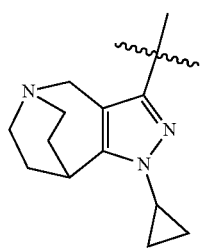

6. The compound of claim 1, or a pharmaceutically acceptable salt or solvate thereof, wherein $R_2$ is

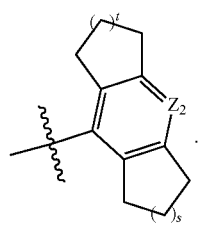

7. The compound of claim 6, or a pharmaceutically acceptable salt or solvate thereof, wherein s is 1, t is 1, $Z_2$ is $C(R_{19})$ and $R_{19}$ is hydrogen or halogen.

8. The compound of claim 1, or a pharmaceutically acceptable salt or solvate thereof, wherein $R_2$ is

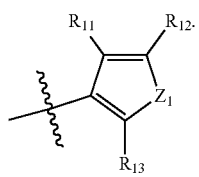

9. The compound of claim 8, or a pharmaceutically acceptable salt or solvate thereof, wherein $Z_1$ is S, —$C(R_{17})$=$C(R_{17})$—, and each $R_{17}$ is independently selected from hydrogen and halogen.

10. The compound of claim 9, or a pharmaceutically acceptable salt or solvate thereof, wherein $R_{11}$ and $R_{12}$ are independently selected from hydrogen, halogen, and $C_1$-$C_6$alkyl, or $R_{11}$ and $R_{12}$ are combined to form a 5-membered cycloalkyl ring.

11. The compound of claim 9, or a pharmaceutically acceptable salt or solvate thereof, wherein $R_{13}$ is $C_2$-$C_9$heteroaryl optionally substituted by 1, 2, 3, or 4 $R_{16}$.

12. The compound of claim 11, or a pharmaceutically acceptable salt or solvate thereof, wherein $R_{13}$ is pyridyl optionally substituted by 1, 2, 3, or 4 $R_{16}$.

13. The compound of claim 12, or a pharmaceutically acceptable salt or solvate thereof, wherein each $R_{16}$ is independently selected from halogen, $C_1$-$C_6$alkyl, $C_1$-$C_6$haloalkyl, and $C_1$-$C_6$alkoxy.

14. The compound of claim 9, or a pharmaceutically acceptable salt or solvate thereof, wherein $R_{13}$ is $C_1$-$C_6$alkyl or $C_3$-$C_5$cycloalkyl.

15. The compound of claim 1, or a pharmaceutically acceptable salt or solvate thereof, wherein $R_2$ is

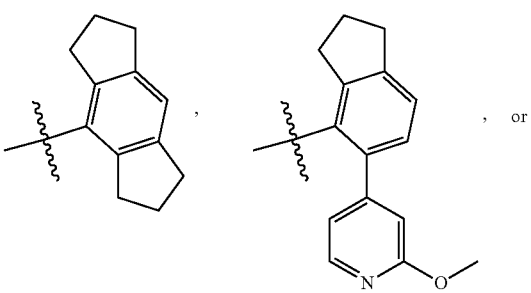, or

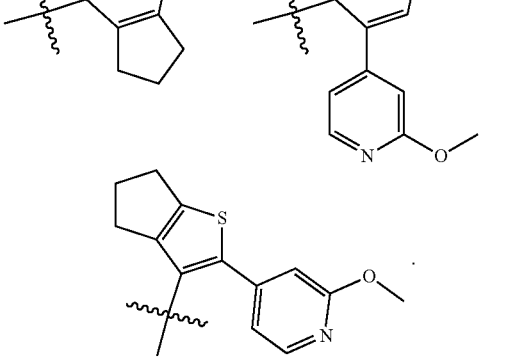

16. The compound of claim 1, or a pharmaceutically acceptable salt or solvate thereof, wherein $X_2$ is —$N(R_4)$—, $X_3$ is —$N(R_5)$—, and $X_1$ is O.

17. The compound of claim 16, or a pharmaceutically acceptable salt or solvate thereof, wherein $R_4$ is hydrogen and $R_5$ is hydrogen.

18. A compound selected from:
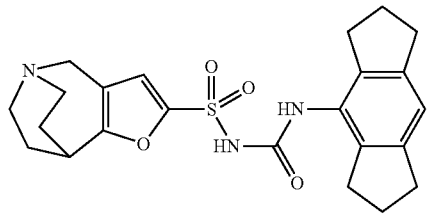 [SMILES: O=C(Nc1c2c(cc3c1CCO3)CCC2)NS(=O)(=O)c1cc2c(o1)C1CCN(CC1)C2]
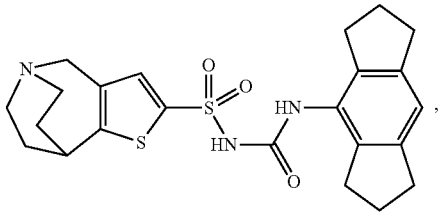 [SMILES: O=C(Nc1c2c(cc3c1CCC3)CCC2)NS(=O)(=O)c1cc2n(n1)C1CCN(CC1)C2],
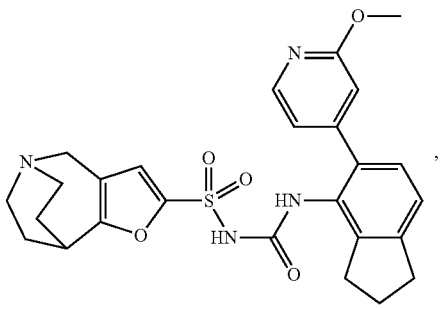,
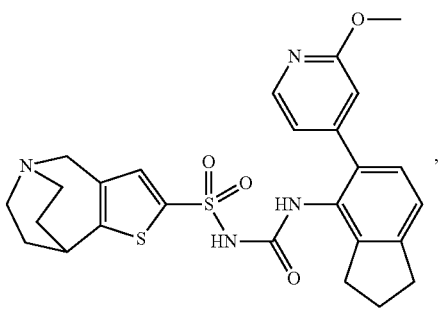,
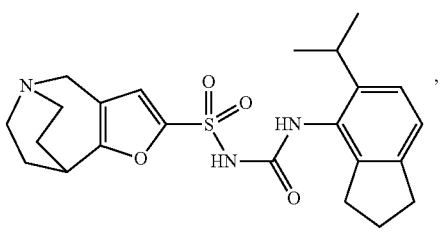,
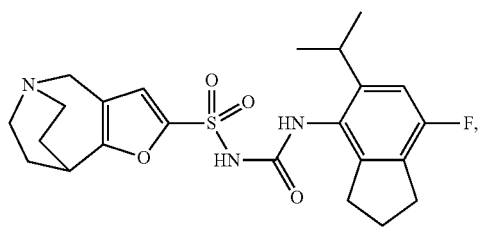,
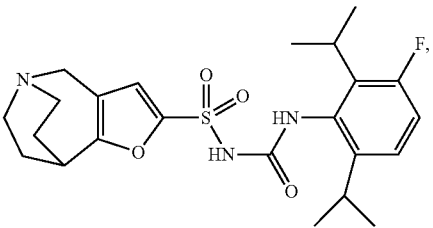
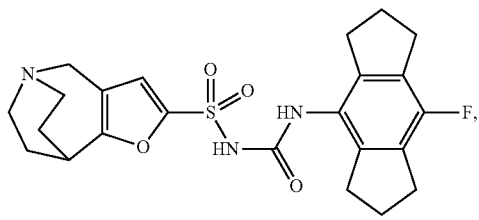,
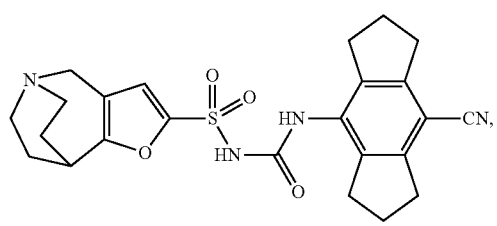,
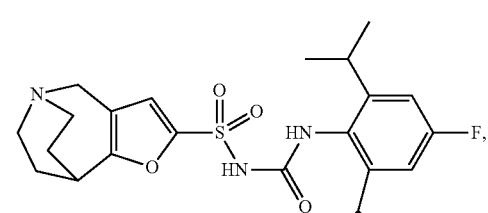,
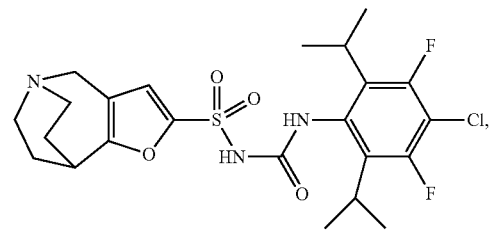,
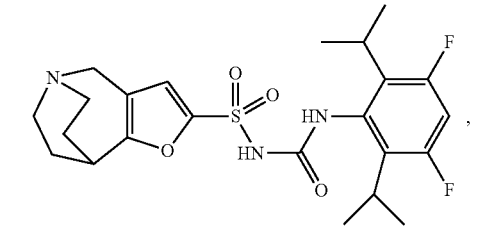,
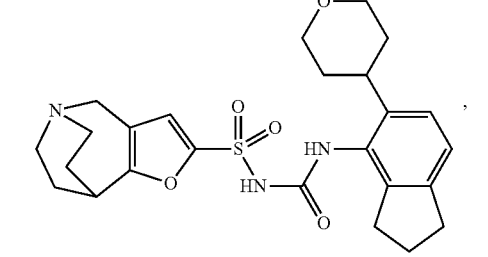, 103
-continued
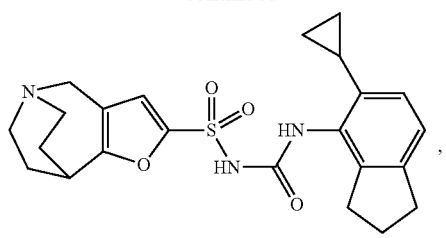,
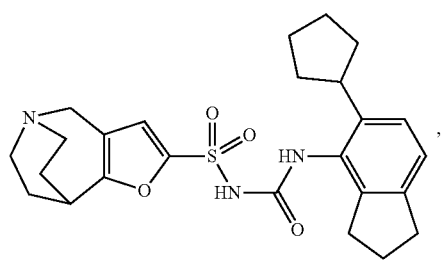,
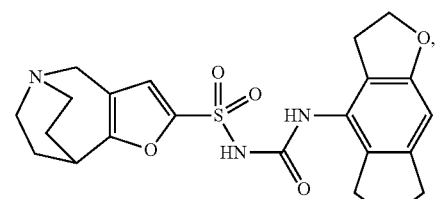,
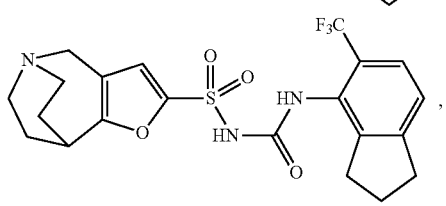,
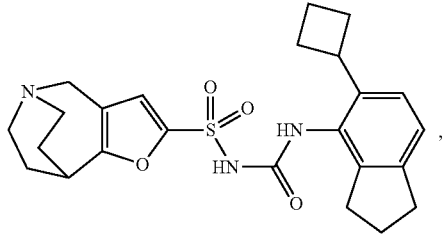,
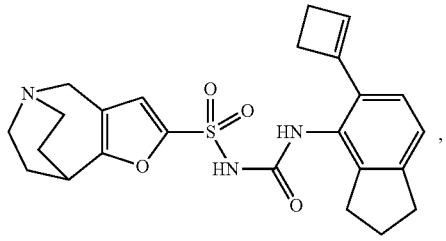,
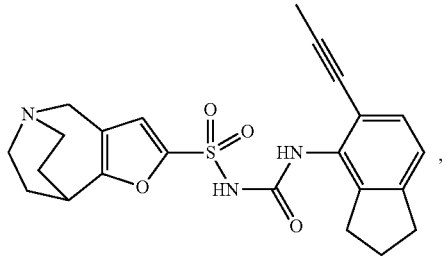,
104
-continued
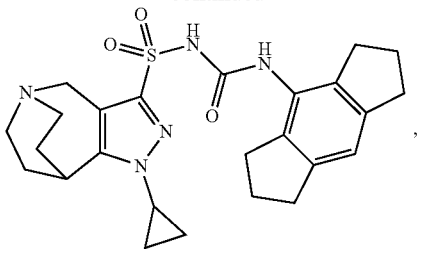,
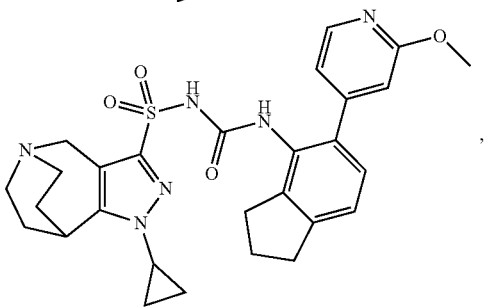,
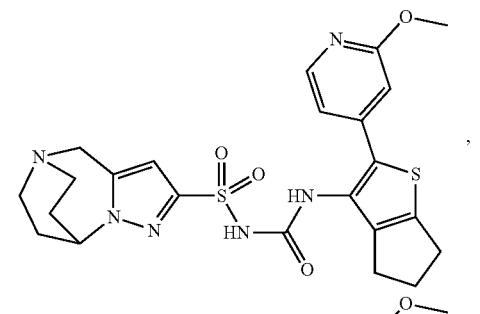,
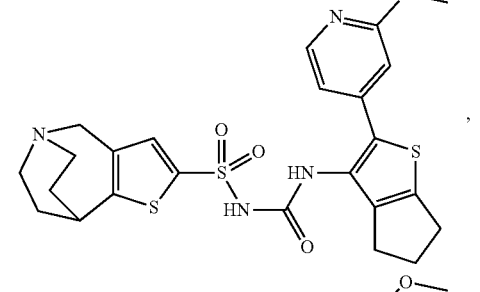,
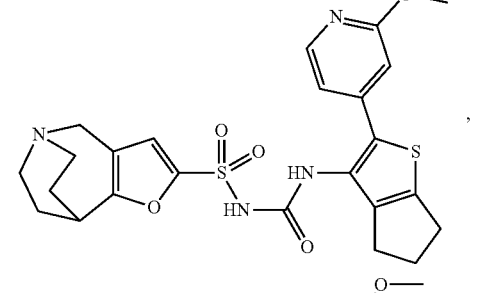,
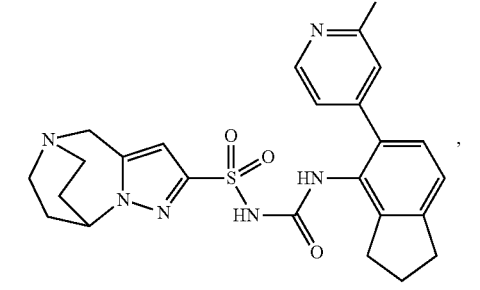,

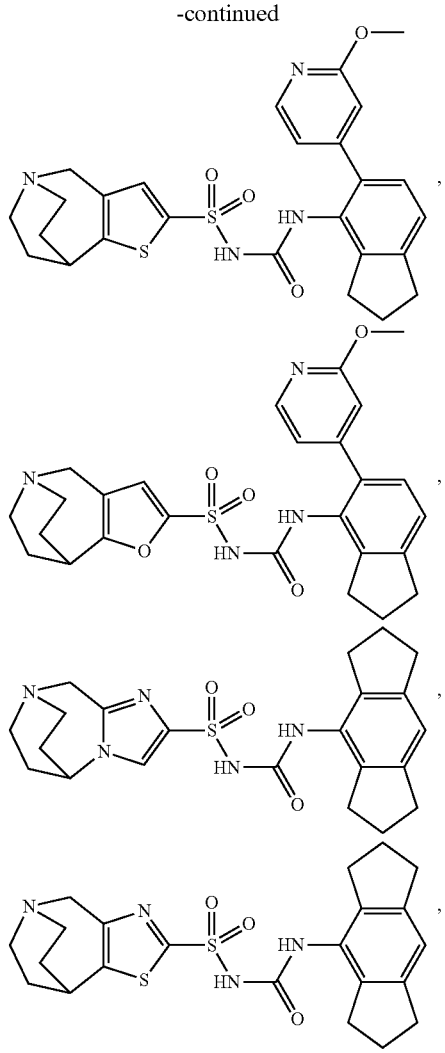

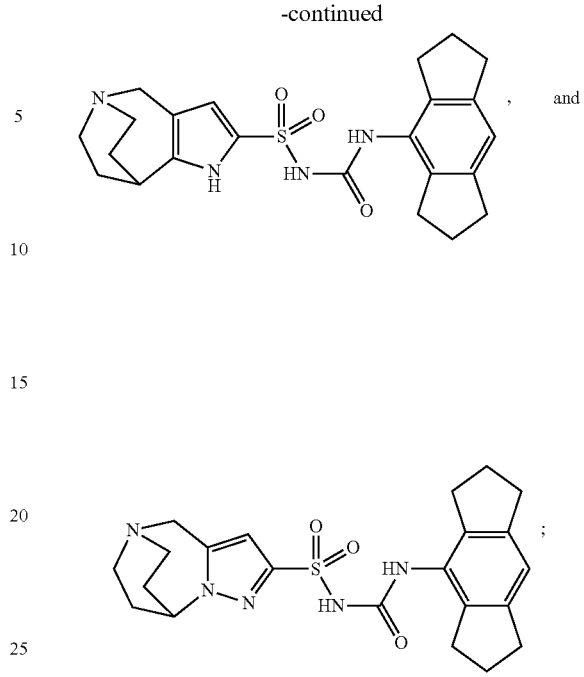

or a pharmaceutically acceptable salt or solvate thereof.

19. A pharmaceutical composition comprising a compound of claim 1, or a pharmaceutically acceptable salt or solvate thereof, and a pharmaceutically acceptable excipient.

20. A method of treating cryopyrin-associated periodic syndromes (CAPS) in a patient in need thereof, comprising administering to the patient a therapeutically effective amount of a compound of claim 1, or a pharmaceutically acceptable salt or solvate thereof, wherein said treating is for therapeutic benefit.

* * * * *